(12) United States Patent
Acton

(10) Patent No.: US 6,436,685 B1
(45) Date of Patent: Aug. 20, 2002

(54) CSAPTP PROTEIN MOLECULES AND USES THEREFOR

(75) Inventor: Susan L. Acton, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/221,448

(22) Filed: Dec. 28, 1998

Related U.S. Application Data

(62) Division of application No. 09/164,193, filed on Sep. 30, 1998, now Pat. No. 6,258,582.

(51) Int. Cl.[7] .................... C12N 9/16; C12N 1/20; C12N 15/00; C12Q 1/68; C07H 21/04

(52) U.S. Cl. ............... 435/196; 435/6; 435/252.3; 435/320.1; 435/254.11; 536/23.2

(58) Field of Search ............... 435/196, 252.3, 435/320.1, 6; 536/23.5

(56) References Cited

U.S. PATENT DOCUMENTS 6,020,179 A * 2/2000 Goli .................... 435/196
6,312,964 B1 * 10/2000 Bandman et al. ......... 435/6

FOREIGN PATENT DOCUMENTS

WO  WO 94/03611  2/1994
WO  WO 98/14596  4/1998

OTHER PUBLICATIONS

EMBL Sequence Database, Accession No. AC 070275, "Protein Tyrosine Phosphatase 4A3 (MPRL–3)".
EMBL Sequence Database, Accession No. AC 075365, "Hprl–3".
Cates, C.A. et. al. (1996) "Prenylation of oncogenic human PTPcaax protein tyrosine phosphatases" *Cancer Letters* 110 (1–2): 49–55.
Denu J.M. et al. (1995) "A catalytic mechanism for the dual–specific phosphatases" *Proc. Natl. Acad. Sci. USA* 92: 5910–5914.
GenBank Accession No. 1401301 for BIIIA3.
GenBank Accession No. AA040215 for Soares fetal heart NbHH19W Homo sapiens cDNA clone IMAGE: 375827 5'.
GenBank Accession No. AA063192 for Soares pineal gland N3HPG Homo sapiens cDNA clone IMAGE: 382152 5'.
GenBank Accession No. AA250856 for Homo sapiens cDNA clone IMAGE:684365 5'.
GenBank Accession No. AA454501 for Soares ovary tumor NbHOT Homo sapiens cDNA clone IMAGE:770725 5'.
GenBank Accession No. AF035645 for Mus musculus potentially prenylated protein tyrosine phosphatase mPRL–3 (Prl3) mRNA.
GenBank Accession No. AF041434 for Homo sapiens potentially prenylated protein tyrosine phosphatase hPRL–3 mRNA.
GenBank Accession No. N40386 for Soares melanocyte 2NbHM Homo sapiens cDNA clone IMAGE:270015 5'.
GenBank Accession No. T61047 Stratagene ovary (#937217) Homo sapiens cDNA clone IMAGE:76967 5'.
GenBank Accession No. U48296 for Human protein tyrosine phosphatase PTPCAAX1 (hPTPCAAX1) mRNA.
GenBank Accession No. U60024 for Ovis aries high sulphur keratin associated protein BIIIA3 (KRTAP2.3) gene.
GenBank Accession No. W37914 for Soares paratyroid tumor NbHPA Homo sapiens cDNA clone IMAGE:322163 5'.
GenBank Accession No. W44902 for Soares fetal lung NbHL19W Homo sapiens cDNA clone IMAGE:308346 5'.
Gerondakis S. et al., (1994) "'Structure of the gene encoding the murine dual specificity tyrosine–threonine phosphatase PAC1" *Genomics* 24(1):182–4.
Hillier, L. et al. (1996) "Generation and Analysis of 280,000 Human Expressed Sequence Tags" *Genome Research* 6(9):807–828.
Ishibashi, T. et. al. (1992) "Expression cloning of a human dual–specificity phosphatase" *Proc. Natl. Acad. Sci. USA* 89(24):12170–12174.
Rohan, P.J. et al. (1993) "PAC–1: A mitogen–induced nuclear protein tyrosine phosphatase" *Science* 259(5102):1763–1766.
Yuvaniyama. J. et al. (1996) "Crystal structure of the dual specificity protein phosphatase VHR" *Science* 272(5266):1328–1331.
Zeng, Q. et al. (1998) "Mouse PRL–2 and PRL–3, Two Potentially Prenylated Protein Tyrosine Phosphatases Homologous to PRL–1" *Biochemical and Biophysical Research Communications* 244:421–427.

* cited by examiner

*Primary Examiner*—Tekchand Saidha
(74) *Attorney, Agent, or Firm*—Amy E. Mandragouras; Marcus C. Laccotripe; Lahive & Cockfield LLP

(57) ABSTRACT

The invention provides isolated nucleic acid molecules, designated CSAPTP nucleic acid molecules, which encode novel protein tyrosine phosphatases. The invention also provides antisense nucleic acid molecules, recombinant expression vectors containing CSAPTP nucleic acid molecules, host cells into which the expression vectors have been introduced, and methods for producing CSAPTP polypeptides.

15 Claims, 10 Drawing Sheets

DNA sequence

GTCGACCCACGGCGTCCGTGGGTTTCTTTTTAATTATCCAAACAGTGGGCAGCTTC
CTCCCCACACACCCAAGTATTTGCACAATATTGTGCGGGGTATGGGGGTGGGTTTT
AAATCTCGTTTCTCTTGGACAAGCACAGGGATCTCGTTCTCCTCATTTTTGGGGTG
TGTGGGGACTTCTCAGTCGTCGGGCGCCATGGCTCGGATGAACCGGCCCGCCCTGC
CGGGCCCGTCGGGAGGCGCCACCAACCCCACCAACGCCCGGTGGAG
GTGAGCTACAAACACATGCGCTTCCTCATCACCCACAACCCCACCAACGCCACGCT
CAGCACCTTCATTGAGGACCTGAAGAAGTACGGGGCTACCACTGTGGTGCGTGTGT
GTGAAGTGACCTATGACAAACGCGCTGGAGAAGGATGGCATCACGTTGTGGAC
TGGCCGTTTGACGATGGGCGGGCCCCCCGGCAAGGTAGTGGAAGACTGGCTG
AGCCTGGTGAAGGCCAAGTTCTGTGAGGCCCGGTCCGTGGCTGTGCACT
GCGTGGCGCTGGGCCGCGCCCTCCAGTCCGTCATCCGCCAGAAGCGCGGAGG
GCGGGATGAAGTACGAGGACGCCATCCAGTTCATCCGCCAGAAATACCGGCCCAAACAGAGGCTG
CCATCAACAGCAAGCAGCTCACCTACCTGGAGAAATACCGGCCCAAACAGAGGCTG
CGGTTCAAAGACCCACACACGAAGACCCGTGCTGTTATGTAGCTCAGGAC
CTTGGCTGGGCCTGTCGTCATGTAGGTCCCAGCCCAGCCTTGGCTGACCTGGAGCCC
TGCCCAGCCCTGCTCTGCCCCGACACTCCGTGCACTTGTCTCCTGTCCGCTGGCCCC
ACATCGCCTTTCCCCCAGCCAGCCTCTGGGCCCTTTCTCCTCTGAGGTGGGTCGCCACTCCCTCT
CCCTCGGCCCCTGGCCCTGGCCCCTGCTGCTCCAGCCCCCCTAGCCCTTTGTGTGGGGTGG
GCCCCTCCACACCAGCCAGGCTGTCCTCCTCCAGCCCTCTTTGACCCCTTGTCCTGA
GGGTATATTTGTAACCACTGCACCTTAAATTATTAGACCAGTCAGGTGCTCCGACAC
CCTGTTCTCGGCACCTTAAATTATTAGACCAGGAGCCAGTCAGGTCCGACAC
CCGAAGGCAATAAAAACAGGACCGTGAAAAAAAAAAAAAAAAAAAAAAAAAAA
AAAAAAAAAAAAAAAAAAAAAAAAAAAAAAAAAAGGGGCCGGN amino acid sequence MARMNRPAPVEVSYKHMRFLITHNPTNATLSTFIEDLKKYGATTVVRVCEVTYDKTPLE
KDGITVVDWPFDDGAPPPGKVVEDWLSLVKAKFCEAPGSCVAVHCVAGLGRAPVLVA
LALIESGMKYEDAIQFIRQKRRGAINSKQLTYLEKYRPKQRLRFKDPHTHKTRCCVM

FIGURE 1

DNA sequence

GTCGACCCACGCGTCCGGCGGCTCCTCTACACAGGCAAGACAGCCTGTAACCATGCCGAC
GAGGTCTGGCCAGGCCTCTATCGGAGACCAGACATGGCTAACAACCGCGGGAGCTT
CGCCGCCTGGGCATCACGCAGTCCTCAATGCCACACGCCGGTGGCGAGGCACGCCC
GAGGCCTATGAGGGCTGGCATCCGCCTACCTGGGTGTTGAGGCGCTGCCAGCC
TTTGACATGAGCATCCACTTCCAGACGGCTGCAGCTTCATCCACGGGCGCTGAGCCAG
CCAGGAGGGAAGATCCTGGTGCATGTGCTTGTGGGCGTGAGCCGATCCCACCCTGGTA
CTGGCCTACCTCATGCTGTACCACCACCTTACCCTCGTGGAGGCCATCAAGAAAGTCAAA
GACCACCGAGAGAGGCCAGTGTGTGGAATGGTCCTGGGATTCGAACACCGCTGGCCAGGTG
GTGAGGTTGGCAGTGTGTGGAAGATGTCCTGGGATTCGAACACCGCTGGCCAGGTG
CTAGGGCTGTAGAATGCAGTCCCATCTCTTGTGCCCAAGTGTTTCCCTCTCCTCA
CTCCCTGGATTCACAGTCCCATCTCTGCGCCACTTGTGCAGAAAGTCAGGATACGC
CAAAACAATGAATGGTGTAGAGCTTGCAGAACCAGAGAACCCCACAGACTTCCACTCCAAG
AAGCATGAATGGTGTAAAAGCTTGCAGAACCAGAGAACCCCACAGACTTCCACTCCAAG
GAGATGGTGTAAAAGCTTGCAGAACCAGAGAACCCCACAGACTTCCACTCCAAG
CACAGGAGAGGTAGCTAGCGTGTGAGGGTTGGCACTAGCCTGAGTCCTGTCTTGGGC
CAAAACATACAGAGGTGCATGCCGTGGCAGTCTTGAAATTGTCACTCGTTACTGATCC
AAGCGTCTCGAGGATAAATAAGATCATGAAAAAAAAAAAGGGCCGC amino acid sequence VDPRVRRLLYTGKTACNHADEVWPGLYLGDQDMANNRRELRRLGITHVLNASHSRWRGTP
EAYEGLGIRYLGVEAHDSPAFDMSIHFQTAADFIHRALSQPGGKILVHCAVGVSRSATLV
LAYLMLYHHLTLVEAIKKVKDHRGEAEPQATVTLCGRGRGVRLGSVVDGHPGRVDQGRRQ
LGCRWKMVLGFEHRWDLARVLPGIHSPFPSLCPSVSLSPSPKTKRAISAPALCAESQGYG
KHECNGVELCETPSIETDSEEMV

FIGURE 2 dna sequence

TNGGATCGAMCNSGCGTCCGGCGGCCCCGCGCTGCTGGAGGCCGGTGCTCTTCTACCCGACGCTGCTCT
ACACCCTGTTCCGCGGAAGGTGCCGGGTCGGGCCACCGGACTGGTACCGACCCCACCGTGCTGCTGGCG
CGCTGCCGGTTGCGGAAGCTTGACGCGCCAGCTGGTACAGGACGAGAACGTGCGCGGGTGATCACCATGAACGAGAGTAC
GAGACGAGGTTCCTGTGCAACTCTTCACAGAGTGGAAGAGACTAGGAGTCGAGCTGCGGCTCAGACAGTAGACATG
ACTGGGATCCCCACCTTGGACAACCTCCAGAGGAGTCCAATTTGCTCTCAAGTACCAGTCGCTGGGCCAGTGTGTTAC
GTGCATTGTAAGGCTGGGCGCTCCAGAGTAGTGCCACTATGTGGCAGCATACCTGATTCAGTTGCACAAATGGGAGTCCAG
AGGAGCTGTAAGAGCCATCGCCCAAGATCCGGGTCATACATCCACATCAGGCCTGGCCAGCTTGATGTTCTTAAAGAGT
TCCACAAAGCAGATTACTGCACSGGCMACAAAGGATGGACTTTTGKCATTTCAAAGACATGATGTATGGGATTAGAAAG
AACTCAAGACACTCCTGCTTGATACAGAACAAAAAGAGCTTAACAGGACCAACAGAGGCTTAAGCCCAGACTTGACGTAACA
GAAATGCCAATAGTAATAGGTAATTTTTCTTCTCGACTTGTTTGTTTTCTNAAATGGCACTGTTGAANNANTNTN
NCTC protein sequence XDRXXVRAAPRCWRPAWRGCSSTRRCSTPCSAGRCRVGRTGTGTTASTPPCCWARCRCGSLTRQLVQDENVRGVITMNEE
YETRFLCNSSQEWKRLGVEQLRLSTVDMTGIPTLDNLQKGVPFALKYQSLGQCVYVHCKAGRSRSATMVAAYLIQVAQMG
VQRRLNEPSPKIRVIHPHQAWPAWMFLKSSTKQITAXATKDGTFXISKT

FIGURE 3

```
ALIGN calculates a global alignment of two sequences
 version 2.0uPlease cite: Myers and Miller, CABIOS (1989)
> Achrb003g03cons - Vector Check                       1315 aa vs.
> Genbank U48296 - Human protein tyrosine phospha      2200 aa
scoring matrix: pam120.mat, gap penalties: -12/-4
38.7% identity;          Global alignment score: 49

10         20        30         40
inputs ------GTCGACC---CACG---CGTCCG-TGGGTTTTCTTTTTTAATTATCCAAACAGT
         .: .::  ;::.    ::.::  :. ' . .:..  :   ::  :.: :::::.
       CGGGATTACTGCCAGGCACAGCACGACCTCTATGCAGACAAGTG-AACTGTAGAAACTGA
            10        20        30        40        50

50              60                          70
inputs GGGCAGCT--TCCT-----CCCCCA-------------------CACCCAAGTATT----
        .:.:::   .::.     ::::::                    :::  ::::.::
       TTACTGCTCCACCAAGAAGCCCCCATAAGAGTGGTTATCCTGGACACAGAAGTGTTGAAT
         60        70        80        90       100       110

80         90       100        110
inputs TG-----CACAATA-TTTGTGC--GGGGTATGG---GGGTGGGTTTTT----AAATC---
        ::     :::::...  .::  :.:  :.:  : ::.   ::.::::  :...   :.. :
       TGAAATCCACAGAGCATTTTACAAGAGTTCTGACCTGGATGGGGTAAACCTCAGTGCACT
        120       130       140       150       160       170

120         130       140       150       160      170
inputs TCGTTTCTCTTGGACA----AGCACAGGGATCTCGTTCTCCT-CAT-TTTTTGGGGGTGT
        ::  :::::: ::::  :.     :    ::.::..:  .  :..  :  ::  :. :::.:.  :
       TCTTTTCTGTTGGCCTCAGTATTACTGGATTGAAGAATTGCTGCTTCTTGTTAGGAGGTT
        180       190       200       210       220       230

180       190        200
inputs GTGGGGACTTCTCAGGTCGTG-----TC---CCCA--GC-CT-------TCT--------
        .       ::::  :::   .:  :.    ::   : ::  :: ::         ::..
       CATTTCACTTATCATTACTTACAACTTCATACTCAAAGCACTGAGAATTTCAAGTGGAGT
        240       250       260       270       280       290

210       220
inputs -------------CTGCAGTCCCTT--CTGCC---CTG----------------------
                     ::  ::::  :::  :. :    :::
       ATATTGAAGTAGACTTCAGTTTCTTTGCATCATTTCTGTATTCAATTTTTTTAATTATTT
        300       310       320       330       340       350

230       240               250       260       270
inputs CCGGGCCC-GTCGGGAG------GC-----GCCATGGCTCGGATGAACCGCCCGGCCCCG
        :  ..::: .: :.:.:      .:       .  :::::::::.:::::::::::.:  ::
       CATAACCCTATTGAGTGTTTTTAACTAAATAACATGGCTCGAATGAACCGCCCAGCTCCT
        360       370       380       390       400       410

280        290       300       310       320       330
inputs GTGGAGGTGAGCTACAAACACATGCGCTTCCTCATCACCCACAACCCCACCAACGCCACG
        ::::::.::  :    :::::. ::::: :  :: ::  ::  ::  :: :::::   :: ::
       GTGGAAGTCACATACAAGAACATGAGATTTCTTATTACACACAATCCAACCAATGCGACC
        420       430       440       450       460       470

340       350       360       370       380       390
inputs CTCAGCACCTTCATTGAGGACCTGAAGAAGTACGGGGCTACCACTGTGGTGCGTGTGTGT
```

FIGURE 4

```
            : :..::    ::  ::.:::::  ::  :::::::::  ::..:  ::::::::..:..::.  :..::.:::
            TTAAACAAATTTATAGAGGAACTTAAGAAGTATGGAGTTACCACAATAGTAAGAGTATGT
         480       490       500       510       520       530

400       410       420       430       440       450
inputs   GAAGTGACCTATGACAAAACGCCGCTGGAGAAGGATGGCATCACCGTTGTGGACTGGCCG
            ::::  .::  :::::::::  .::  :      :::::::::..::..:::    :::   ::  ::  :::::
            GAAGCAACTTATGACACTACTCTTGTGGAGAAAGAAGGTATCCATGTTCTTGATTGGCCT
         540       550       560       570       580       590

460       470       480       490       500       510
inputs   TTTGACGATGGGGCGCCCCCGCCCGGCAAGGTAGTGGAAGACTGGCTGAGCCTGGTGAAG
            :::::  :::::  ::..::  ::.  ::..:  ::.:.::  ::..:::::  :.::  ::  :::::.
            TTTGATGATGGTGCACCACCATCCAACCAGATTGTTGATGACTGGTTAAGTCTTGTGAAA
         600       610       620       630       640       650

520       530       540       550       560       570
inputs   GCCAAGTTCTGTGAGGCCCCCGGCAGCTGCGTGGCTGTGCACTGCGTGGCGGGCCTGGGC
            .     :::::    :::::..:    ::  ::  .:  ::  .:  :::::  ::  :::::  ::..:::::  ::
            ATTAAGTTTCGTGAAGAACCTGGTTGTTGTATTGCTGTTCATTGCGTTGCAGGCCTTGGG
         660       670       680       690       700       710

580       590       600       610       620       630
inputs   CGGGCTCCAGTCCTTGTGGCGCTGGCCCTTATTGAGAGCGGGATGAAGTACGAGGACGCC
            :.::::::::  :::::  ::  ::.::  :.:::::..:  ::..:::::.:::::..::  ::
            AGAGCTCCAGTACTTGTTGCCCTAGCATTAATTGAAGGTGGAATGAAATACGAAGATGCA
         720       730       740       750       760       770

640       650       660       670       680       690
inputs   ATCCAGTTCATCCGCCAGAAGCGCCGCGGAGCCATCAACAGCAAGCAGCTCACCTACCTG
            .:  ::..:::::    :  ::..::::  ::  :::::  .:  ::::::::::::.::      ::    ::
            GTACAATTCATAAGACAAAAGCGGCGTGGAGCTTTTAACAGCAAGCAACTTCTGTATTTG
         780       790       800       810       820       830

700       710       720       730             740
inputs   GAGAAATACCGGCCCAAACAGAGGCTGCGGTTCAAAGA--CCCAC----------ACA-C
            :::::..::  ::  ::  :::  .:  :::::::  :::::::::    ::  ::          :::  :
            GAGAAGTATCGTCCTAAAATGCGGCTGCGTTTCAAAGATTCCAACGGTCATAGAAACAAC
         840       850       860       870       880       890

750              760       770
inputs   ----GCA--CAAGA----------CCCGGTGCTGCGTTATGTAGCTC-------AGGAC
            :::   :::  :              ::  ..:::::.:    :.::..  .:          :::.:
            TGTTGCATTCAATAAAATTGGGGTGCCTAATGCTACTGGAAGTGGAACTTGAGATAGGGC
         900       910       920       930       940       950

780                    790           800         810
inputs   CTTGGCTG----------GGCCTG---GTCGTCAT-GTAGGTCAGGA-------CCTTG
            :::..    ::              .::.         ::  :    :.:  :::.::::....              ::..:.
            CTAATTTGTTATACATATTAGCCAACATGTTGGCTTAGTAAGTCTAATGAAGCTTCCATA
         960       970       980       990      1000      1010

820       830                                    840
inputs   GCTGGACCTGGAGGC-------CCTG-CC------------------CAGCC-CTG---
            :  .:  :    ..:::::        :::.:  ::                              ::.:::  :::
            GGAGTATTGAAAGGCAGTTTTACCAGGCCTCAAGCTAGACAGATTTGGCAACCTCTGTAT
         1020      1030      1040      1050      1060      1070
```

FIGURE 4A

```
                      850              860        870
inputs  --------C--TCTGCCCA-------GCCCAGCAGGGGCTCCAGGC--------------
                :  ::..:: :          .:  .:::...: : :. ::
        TTGGGTTACAGTCAACCTATTTGGATACTTGGCAAAAGATTCTTGCTGTCAGCATATAAA
        1080      1090      1100      1110      1120      1130

880                      890
inputs  -----CTTGGC------------TGGCC-----CCACATC--GC----------------
             :::: :             ::.::     ::: ::: ::
        ATGTGCTTGTCATTTGTATCAATTGACCTTTCCCCAAATCATGCAGTATTGAGTTATGAC
        1140      1150      1160      1170      1180      1190

900
inputs  ---------CTTTTCC----------TC--------------------------------
                 ::.::::           ::
        TTGTTAAATCTATTCCCATGCCAGAATCTTATCAATACATAAGAAATTTAGGAAGATTAG
        1200      1210      1220      1230      1240      1250

910                          920       930
inputs  -----------CCCGACAC----CT---------------CCGTGCACTTGTG---TCCG
                   :::..:::    ::                ::.:.:: ..::.   :::
        GTGCCAAAATACCCAGCACAATACTTGTATATTTTTAGTACCATACAGAAGTAAAATCCC
        1260      1270      1280      1290      1300      1310

940                                 950
inputs  AGGAGCGAGGAGC---------------------CCCTCGGGC--------CCTGGGT-
        :::::.: : ::.:                     :: ::.. :         : : :..
        AGGAACTATGAACACTAGACCTTATGTGGTTTATTCCTTCAATCATTTCAAACATTGAAA
        1320      1330      1340      1350      1360      1370

960          970       980                   990
inputs  ----GGCCT-C-TGG------GCCCTTTCTCCT---------GTCTCCGCCACTC---CC
            ::::: : :::       :::   :::. :          .:::: :: ::    ::
        GTAGGGCCTACATGGTTATTTGCCTGCTCACTTTATGTTTACATCTCCCACATTCATACC
        1380      1390      1400      1410      1420      1430

1000        1010             1020      1030
inputs  TCTG-GCGGC------GCT-GGCCGTGG---------------CTCTGTCTCTCTGAGG
        . :. .:: :      ::: ..::.: :                : .:::: ..:.:..
        AATATACGTCAGGTTTGCTTAACCATTGATTTTTTTTTTTTACCAAGTCTTACAGTGA
        1440      1450      1460      1470      1480      1490

1040              1050
inputs  TGGGT---CGGGCG-CC------CTC------TGC------------CCGCCC------
        :  .:    :: :  ::       :::      :::              :: ::
        TTATTTTACGTGTTTCCATGTATCTCACTTTGTGCTGTATTAAAAAAACCTCCATTTTGA
        1500      1510      1520      1530      1540      1550

1060                                        1070
inputs  ----CCTC------C-----CACA---C-----------CAG---------CCAGGC---
            : .:      :     ::::     :             :::-         ::. .:
        AAATCTACGTTGTACAGAAGCACATGTCTTTAATGTCTTCAGACAAAAAAGCCTTACATT
        1560      1570      1580      1590      1600      1610

1080                                  1090      1100
inputs  -------TGGTCTC-CTCTA--------------------GCCTGTTTGTTGTG-GGGT
```

FIGURE 4A-1

```
               :: :   : :::,.                         :::::. ......:.. :::,
        AATTTAATGTTTGCACTCTGAGGTGCAACTTAACAGGGAGGGCCTGAGAAAAGAATGGGA
        1620      1630      1640      1650      1660      1670

1110                    1120          1130
inputs  GGGGG--------TATATTTT--------GTAACCA----CTGG-GCCCCCA--------
        :::::         :::.::::       ::..::.     :: : ::    ::
        GGGGGCTATTAATTATTTTTTAGCAAAATGTTGCCTTTGTCTTGTGCAAACATGTAGAAT
        1680      1690      1700      1710      1720      1730

1140
inputs  --GCCC------CT-------------------------------------------C
        :: :      ::                                              :
        ATGCTCTTTAATCTAGTAAAATATTTTTTTAAAAGGTAGAGATGCTTTGTTATTGTAATC
        1740      1750      1760      1770      1780      1790

1150              1160       1170
inputs  TTTTGCGACCC------CTTGTCCTGA---CCTGTTCT---CGG------------CACC
        .:...: .::       :::::  : .    :: .:.::    :.:           :: :
        ATAAACTTCCTGAAATTCTTGTAATTTTTTCCCATACTTATCAGAAGTGTGTTTACCAAC
        1800      1810      1820      1830      1840      1850

1180      1190
inputs  TTAAATTA-TTAGA-----------------CC--CC--------------------
        :::..::. ::.::                 :: ::
        TTATTTTGTTTGAAAGTGTGATTTTTTTTTTCCTTCCCAACCTCTCTTGCAAAAAAGA
        1860      1870      1880      1890      1900      1910

1200                                1210
inputs  ---GGG-----------------GCAG---TCAG-----------------GTGCT--
           :::                 ::::   ::..                 :.:::
        AATGGGTTTCTGCTAATGAATTGAGCAGAGATCTAATATTTTATATGCCTTTTGAGCTGT
        1920      1930      1940      1950      1960      1970 inputs  -------------------CCGGACA----------------------------------
                           :  ::::
        GTAAGTTAATATTTGATACTTGACAATTTGTTTTATTATGTAATTGATAAAATGGTGATG
        1980      1990      2000      2010      2020      2030

1220      1230      1240
inputs  ---------------C--CCGAAGGCAATAA--AACAGGAG---------------CC
                       :  ::..: . ....: ..:.::.:                :
        TGTATTAATGTTAGTTCAACCATATATTTATACTGTCTGGGGATGTGTGGTTATAGTTCT
        2040      2050      2060      2070      2080      2090

1250      1260                 1270      1280
inputs  GTGAAAAAAAAAAAAAAA-------------AAAAAAAAAAAAAAAAAAAAAAAAA
        :::..:.:::.:.:......            ....:::: ..:... .:.:. ...::
        GTGGGAGAAATAATTTTGTCAGTGTTCACCAGCTTGTAAAAACTTAGTGCGAGAGCTGAA
        2100      2110      2120      2130      2140      2150

1290      1300      1310
inputs  AAAAAAAAAAAAAAAAGGGCG-GC------CGN--------
        : :. .:::.:::.:: :::. ::       :..
        ACATCTAAATAAATAATGACATGCATTTATCATCATTGAAA
        2160      2170      2180      2190      2200
```

FIGURE 4A-2

ALIGN calculates a global alignment of two sequences
version 2.0uPlease cite: Myers and Miller, CABIOS (1989)
>PTPCAAX1                                                           173 aa
> fchrb003g03
scoring matrix: pam120.mat, gap penalties: -12/-4
78.6% identity;                 Global alignment score: 776

```
                  10        20        30        40        50        60
inputs   MARMNRPAPVEVTYKNMRFLITHNPTNATLNKFIEELKKYGVTTIVRVCEATYDTTLVEK
         :::::::::::::::: ::::::::::::::::: :::::::::  : .::: :  . ::
         MARMNRPAPVEVSYKHMRFLITHNPTNATLSTFIEDLKKYGATTVVRVCEVTYDKTPLEK
                  10        20        30        40        50        60

70        80        90       100       110       120
inputs   EGIHVLDWPFDDGAPPSNQIVDDWLSLVKIKFREEPGCCIAVHCVAGLGRAPVLVALALI
         .:  ::::::::::: ::  :  ::::::::::  ::: ::::::::::::::::::::
         DGITVVDWPFDDGAPPPGKVVEDWLSLVKAKFCEAPGSCVAVHCVAGLGRAPVLVALALI
                  70        80        90       100       110       120

130       140       150       160       170
inputs   EGGMKYEDAVQFIRQKRRGAFNSKQLLYLEKYRPKMRLRFKDSNGHRNNCCIQ
         :::::::::.:::::::::::. :::::.::::::::: :::::  ::. ..
         ESGMKYEDAIQFIRQKRRGAINSKQLTYLEKYRPKQRLRFKDPHTHKTRCCVM
                 130       140       150       160       170
```

FIGURE 5

```
ALIGN calculates a global alignment of two sequences
 version 2.0uPlease cite: Myers and Miller, CABIOS (1989)
> b037d02 prot                                           263 aa vs.
> SwissProt P51452 - DUAL SPECIFICITY PROTEIN PHO    185 aa
scoring matrix: pam120.mat, gap penalties: -12/-4
22.5% identity;           Global alignment score: 205

10           20          30          40
inputs    ----VDPRVRRL--LYTGKTAC----NHA-DEVWPGLYLGDQDMANNRRELRRLGITHVL
              . :. :   :  .. ..:     ... .::  : .:.:. ..:..   :..::::::::
          MSGSFELSVQDLNDLLSDGSGCYSLPSQPCNEVTPRIYVGNASVAQDIPKLQKLGITHVL
              10          20          30          40          50          60

50           60          70          80          90          100
inputs    NASHSRW----RGTPEAYEGLGIRYLGVEAHDSPAFDMSIHFQTAADFIHRALSQPGGKI
          ::. ..:         ... : . ::  :::.  :.:.....:..:  :.  :::::..::.:  .:..
          NAAEGRSFMHVNTNANFYKDSGITYLGIKANDTQEFNLSAYFERAADFIDQALAQKNGRV
              70          80          90         100         110         120

110          120         130         140         150         160
inputs    LVHCAVGVSRSATLVLAYLMLYHHLTLVEAIKKVKDHRGEAEPQATVT-LCG-RGRGVRL
          :::: :  : :::.:::::.::::.    . .    :.   :   .    ..  ::       .:  ..
          LVHCREGYSRSPTLVIAYLMMRQKMDVKSALSIVRQNREIGPNDGFLAQLCQLNDRLAKE
             130         140         150         160         170         180

170          180         190         200         210         220
inputs    GSVVDGHPGRVDQGRRQLGCRWKMVLGFEHRWDLARVLPGIHSPFPSLCPSVSLSPSPKT
          :  .
          GKLKP-------------------------------------------------------

230          240         250         260
inputs    KRAISAPALCAESQGYGKHECNGVELCETPSIETDSEEMV

```
ALIGN calculates a global alignment of two sequences
 version 2.0uPlease cite: Myers and Miller, CABIOS (1989)
> Genbank 1657672 | Z68315 Caenorhabditis elegans   150 aa vs.
> Achrb067c02.aa                                    202 aa
scoring matrix: pam120.mat, gap penalties: -12/-4
24.0% identity;      Global alignment score: -63

10
inputs    -----------------------------------------------MPFRSMKDEL
                                                     .:..::.  .:
          VRAATALLEAGLARVLFYPTLLYTLFRGKVPGRAHRDWYHRIDPTVLLGALPLRSLTRQL
               10        20        30        40        50        60

20        30        40        50        60        70
inputs    IQKENVGGVVCCTEEFELKAAMNAMREVDWKNEGVEFFAVPMKDFTGTAPRAEINEAVEF
          .:  :::  ::.   .::.: .    :..  .:   ::    :::  . ..  : ::..  .... .::
          VQDENVRGVITMNEEYETRFLCNSSQE--WKRLGVEQLRLSTVDMTGIPTLDNLQKGVQF
               70        80        90       100            110

80        90       100       110       120       130
inputs    IESVASKGKTVYVHCKAGRTRSATVATCYLMKSRNWMSNVAWEFLKDKRHQVLLRNAHWR
           :  :..  :::::::::::..::::...    :::.. ...  .. :    .   :   . .:  ..
          ALKYQSLGQCVYVHCKAGRSRSATMVAAYLIQVHKWSPEEAVRAIAKIRSYIHIRPGQLD
              120       130       140       150       160       170

140       150
inputs    TVNEYRRFLDSNSSSTG----SSN
          ...:...  .. :      :  .
          VLKEFHKQITARATKDGTFVISKT
             180       190       200
```

FIGURE 7

CSAPTP PROTEIN MOLECULES AND USES THEREFOR

This application is a division of U.S. Ser. No. 09/164,193, filed Sep. 30, 1998, now U.S. Pat. No. 6,258,582.

BACKGROUND OF THE INVENTION

Phosphate tightly associated with protein has been known since the late nineteenth century. Since then, a variety of covalent linkages of phosphate to proteins have been found. The most common involve esterification of phosphate to serine and threonine, with smaller amounts being covalently linked to lysine, arginine, histidine, aspartic acid, glutamic acid, and cysteine. The occurrence of phosphorylated proteins implies the existence of one or more protein kinases capable of phosphorylating amino acid residues on proteins, and also of protein phosphatases capable of hydrolyzing phosphorylated amino acid residues on proteins.

Protein kinases play critical roles in the regulation of biochemical and morphological changes associated with cellular growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721).

The overall level, in cells, of protein tyrosine phosphorylation, as well as the phosphorylated state of any given protein, arises from the balance of Protein Tyrosine Kinase (PTK) and Protein Tyrosine Phosphatase (PTPase) activities. Thus PTPases have been proposed as key regulatory elements of cell growth control (Hunter, 1989, Cell 58:1013–1016).

PTKs were discovered and characterized more than one decade earlier than PTPases and in the last few years a large number of studies has led to the identification of many new PTPases and some of them have been accurately characterized. In addition, findings on the biological role of some PTPases in cells have recently been reported (Pondaven, 1991, Adv Prot Phosphatases 6:35–57). Current work suggests that PTKs and PTPases are equally important in many biological processes ranging from cell growth control to cell differentiation and development. In particular, the ocogenic potential of PTKs and the ability of PTPases to counteract PTK oncogenic activation by antiproliferative action suggests that the genes coding for PTPases, in many instances, may be considered tumor-suppressing genes or even anti-oncogenes The existence of PTPases was first predicted to explain the rapid loss of phosphorylation of in vitro phosphorylated membrane proteins (Carpenter et al., 1979, J Biol Chem 254:4884–4891). The main PTPase in human placenta (PTP1B) was purified to homogeneity and sequenced (Tonks et al., 1988, J Biol Chem 263:6722–2730; Charbonneau et al., 1989, PNAS USA 86:5252–5256). Sequence homology between the catalytic domain of PTP1B and the leukocyte common antigen (LCA, or CD45) was demonstrated, indicating that PTPases can be considered a family of structurally related molecules.

The effects of many growth factors such as NGF, BDNF, NT3, FGF, insulin and IGF1 are known to be mediated by high-affinity receptors with tyrosine kinases activity (Fantl et al. *Annu. Rev. Biochem.*, 62 (1993) 453–481; Schlessinger and Ulrich *Neuron*, 9 (1992) 383–391; Ullrich and Schlessinger *Cell*, 61 (1990) 203–212). Expression of several tyrosine phosphatase genes has been detected in the brain (Jones et al. *J. Biol. Chem.*, 264 (1989) 7747–7753), including RPTPα(Kaplan et al. *Proc. Natl. Acad. Sci.* USA, 87 91990) 7000–7004; Sap et al. *Proc. Natl. Acad. Sci.* USA, 87 (1990) 6112–6116), RNPTPX (Guan et al. *Proc. Natl. Acad. Sci.* USA, 87 (19910) 1501–1505), STEP (Lombroso et al. *Proc. Natl. Acad. Sci.* USA, 88 (1991) 7242–7246), SH-PTP2 (Freeman et al. *Proc. Natl. Acad. Sci.* USA, 89 (1992) 11239–11243), MPTPδ (Mizuno et al. *Mol. Cell. Biol.*, 13 (1993) 5513–5523), DPTP99A and DPTP10D (Yang et al. *Cell*, 67 (1991) 661–673).

Intraventricular administration of either NGF, BDNF, insulin or IGF1 prevents delayed neuronal death in the CA1 subfield of the hippocampus (Beck et al. *J. Cereb Blood Flow Metab.*, 14 (1994) 689–692; Shigeno et al. *J. Neurosci.*, 11 (1991) 2914–2919; Zhu and Auer *J. Cereb. Blood Flow Metab.*, 14 (1994) 237–242).

Tyrosine kinase inhibitors block the tyrosine phosphorylation of MAP kinase (Blenis *Proc. Natl. Acad. Sci.* USA, 90 (1993) 5889–5892; Pelech and Sanghera *Science*, 257 (1992) 1335–1356) and prevent delayed neuronal death after forebrain ischemia (Kindy *J. Cereb. Blood Flow Metab*, 13 (1993) 372–377). During reperfusion after ischemia, tyrosine phosphorylation of proteins increases in the hippocampus but some proteins in the hippocampus are dephosphorylated (Campos-Gonzalez *J. Neurochem.*, 59 (1992) 1955–1958; Hu and Wieloch *J. Neurochem*, 62 (1994) 1357–1367; Takano et al. *J. Cereb. Blood Flow Metab.*, 15 (1995) 33–41). These observations suggest that tyrosine phosphorylation plays an important role in the delayed neuronal death which occurs as a result of ischemia-reperfusion injury.

A number of PTPases, in addition to the hydrolytic activity on phosphotyrosine, show some phosphoserine/phosphothreonine phosphatase activity. These enzymes, mostly localized in the nucleus and referred to as dual-specificity PTPases (dsPTPases), are emerging as a subclass of PTPases acting as important regulators of cell cycle control and mitogenic signal transduction possibly by controlling the activity of signal transduction proteins like ERK. In fact, they appear responsible for in vivo nuclear dephosphorylation and inactivation of nuclear dephosphorylation and inactivation of MAP kinases (Alessi et al., 1995, *Curr Biol* 5:195–283). These enzymes exhibit sequence identity to the vaccinia H-1 gene product, the first identified dsPTPase (Guan et al., 1991, *Nature* 350:359–362). Several dsPTPases differing from each other in length have been identified. These enzymes and the other PTPase subclasses share an active site sequence motif showing only a limited sequence homology beyond this region.

Given the importance of such protein tyrosine phosphatases in the regulation of the cell cycle, there exists a need to identify novel protein tyrosine phosphatases which function as modulators in the cell cycle such as the suppression of proliferation and whose aberrant function can result in disorders arising from improper cell cycle regulation such as cancer.

SUMMARY OF THE INVENTION

The present invention is based, at least in part, on the discovery of novel nucleic acid molecules and proteins encoded by such nucleic acid molecules, referred herein as "Cardiovascular System Associated Protein Tyrosine Phosphatase" ("CSAPTP") proteins. The CSAPTP nucleic acid and protein molecules of the present invention are useful as modulating agents in regulating a variety of cellular processes, e.g., cardiac cellular processes. Accordingly, in one aspect, this invention provides isolated nucleic acid molecules encoding CSAPTP proteins or biologically active portions thereof, as well as nucleic acid fragments suitable as primers or hybridization probes for the detection of CSAPTP-encoding nucleic acids.

In one embodiment, a CSAPTP nucleic acid molecule of the invention is at least 57% or more homologous to a nucleotide sequence (e.g., to the entire length of the nucleotide sequence) including SEQ ID NO:1, SEQ ID NO:3, or a complement thereof. In another embodiment, a CSAPTP nucleic acid molecule is at least 40%, 45%, 50%, 55%, 60%, 65%, 70%, 75%, 80%, 85%, 90%, 95%, 98%, 99% or more homologous to a nucleotide sequence including SEQ ID NO:4, SEQ ID NO:6, or a complement thereof. In yet another embodiment, a CSAPTP nucleic acid molecule is at least 40%, 45%, 50%, 55%, 60%, 65%, 70%, 75%, 80%, 85%, 90%, 95%, 98%, 99% or more homologous to a nucleotide sequence including SEQ ID NO:7, SEQ ID NO:9, or a complement thereof.

In a preferred embodiment, the isolated nucleic acid molecule includes the nucleotide sequence shown SEQ ID NO:1or 3, or a complement thereof. In another embodiment, the nucleic acid molecule includes SEQ ID NO:3 and nucleotides 1–248 of SEQ ID NO:1. In another preferred embodiment, the nucleic acid molecule has the nucleotide sequence shown in SEQ ID NO:1 or 3. In another preferred embodiment, the nucleic acid molecule comprises a fragment of at least 499 nucleotides of the nucleotide sequence of SEQ ID NO:1, SEQ ID NO:3, or a complement thereof.

In another preferred embodiment, the isolated nucleic acid molecule includes the nucleotide sequence shown SEQ ID NO:4 or 6, or a complement thereof. In another embodiment, the nucleic acid molecule includes SEQ ID NO:6 and nucleotides 1–342 of SEQ ID NO:4. In another embodiment, the nucleic acid molecule includes SEQ ID NO:6 and nucleotides 790–1016 of SEQ ID NO:4. In another preferred embodiment, the nucleic acid molecule has the nucleotide sequence shown in SEQ ID NO:4 or 6. In another preferred embodiment, the nucleic acid molecule comprises a fragment of at least 626 nucleotides of the nucleotide sequence of SEQ ID NO:4, SEQ ID NO:6, or a complement thereof.

In another preferred embodiment, the isolated nucleic acid molecule includes the nucleotide sequence shown SEQ ID NO:7 or 9, or a complement thereof. In another embodiment, the nucleic acid molecule includes SEQ ID NO:9 and nucleotides 628–814 of SEQ ID NO:7. In another preferred embodiment, the nucleic acid molecule has the nucleotide sequence shown in SEQ ID NO:7 or 9. In another preferred embodiment, the nucleic acid molecule comprises a fragment of at least 531 nucleotides of the nucleotide sequence of SEQ ID NO:7, SEQ ID NO:9, or a complement thereof.

In another embodiment, a CSAPTP nucleic acid molecule includes a nucleotide sequence encoding a protein having an amino acid sequence sufficiently homologous to the amino acid sequence of SEQ ID NO:2, SEQ ID NO:5, or SEQ ID NO:8. In a preferred embodiment, a CSAPTP nucleic acid molecule includes a nucleotide sequence encoding a protein having an amino acid sequence at least 50%, 55%, 60%, 65%, 70%, 75%, 79%, 80%, 85%, 90%, 95%, 99% or more homologous to an amino acid sequence including SEQ ID NO:2 (e.g., the entire amino acid sequence of SEQ ID NO:2). In another preferred embodiment, a CSAPTP nucleic acid molecule includes a nucleotide sequence encoding a protein having an amino acid sequence at least 10%, 15%, 20%, 23%, 25%, 30%, 35%, 40%, 45%, 50%, 55%, 60%, 65%, 70%, 75%, 80%, 85%, 90%, 95%, 98%, 99% or more homologous to an amino acid sequence including SEQ ID NO:5 (e.g., the entire amino acid sequence of SEQ ID NO:5). In yet another preferred embodiment, a CSAPTP nucleic acid molecule includes a nucleotide sequence encoding a protein having an amino acid sequence at least 10%, 15%, 20%, 24%, 25%, 30%, 35%, 40%, 45%, 50%, 55%, 60%, 65%, 70%, 75%, 80%, 85%, 90%, 95%, 98%, 99% or more homologous to an amino acid sequence including SEQ ID NO:8 (e.g., the entire amino acid sequence of SEQ ID NO:8).

In another preferred embodiment, an isolated nucleic acid molecule encodes the amino acid sequence of a human CSAPTP. In yet another preferred embodiment, the nucleic acid molecule includes a nucleotide sequence encoding a protein which includes the amino acid sequence of SEQ ID NO:2, SEQ ID NO:5, or SEQ ID NO:8. In yet another preferred embodiment, the nucleic acid molecule includes a nucleotide sequence encoding a protein having the amino acid sequence of SEQ ID NO:2, SEQ ID NO:5, or SEQ ID NO:8.

Another embodiment of the invention features nucleic acid molecules, preferably CSAPTP nucleic acid molecules, which specifically detect CSAPTP nucleic acid molecules relative to nucleic acid molecules encoding non-CSAPTP proteins. For example, in one embodiment, such a nucleic acid molecule is at least 350, 400, 450, 500, 550, 600, 650, 700, 750, 800, 850, 900, 950, 1000, 1050, 1100 nucleotides in length and hybridizes under stringent conditions to a nucleic acid molecule comprising the nucleotide sequence shown in SEQ ID NO:1, SEQ ID NO:4, SEQ ID NO:7, or a complement thereof. In a particularly preferred embodiment, the nucleic acid molecule comprises a fragment of at least 994 nucleotides of the nucleotide sequence of SEQ ID NO:1, SEQ ID NO:3, or a complement thereof. In preferred embodiments, the nucleic acid molecules are at least 15 (e.g., contiguous) nucleotides in length and hybridize under stringent conditions to nucleotides 1–17 and 1011–1315 of SEQ ID NO:1.

In another particularly preferred embodiment, the nucleic acid molecule comprises a fragment of at least 626 nucleotides of the nucleotide sequence of SEQ ID NO:4, SEQ ID NO:6, or a complement thereof. In preferred embodiments, the nucleic acid molecules are at least 15 (e.g., contiguous) nucleotides in length and hybridize under stringent conditions to nucleotides 1–342 of SEQ ID NO:4. In preferred embodiments, the nucleic acid molecules are at least 15 (e.g., contiguous) nucleotides in length and hybridize under stringent conditions to nucleotides 1002–1016 of SEQ ID NO:4.

In another particularly preferred embodiment, the nucleic acid molecule comprises a fragment of at least 531 nucleotides of the nucleotide sequence of SEQ ID NO:7, SEQ ID NO:9, or a complement thereof. In preferred embodiments, the nucleic acid molecules are at least 15 (e.g., contiguous) nucleotides in length and hybridize under stringent conditions to nucleotides 1–103 and 774–814 of SEQ ID NO:7.

In other preferred embodiments, the nucleic acid molecule encodes a naturally occurring allelic variant of a polypeptide which includes the amino acid sequence of SEQ ID NO:2, wherein the nucleic acid molecule hybridizes to a nucleic acid molecule which includes SEQ ID NO:1or SEQ ID NO:3 under stringent conditions. In other preferred embodiments, the nucleic acid molecule encodes a naturally occurring allelic variant of a polypeptide which includes the amino acid sequence of SEQ ID NO:5, wherein the nucleic acid molecule hybridizes to a nucleic acid molecule which includes SEQ ID NO:4 or SEQ ID NO:6 under stringent conditions. In other preferred embodiments, the nucleic acid molecule encodes a naturally occurring allelic variant of a polypeptide which includes the amino acid sequence of SEQ ID NO:8, wherein the nucleic acid molecule hybridizes to a nucleic acid molecule which includes SEQ ID NO:7 or SEQ ID NO:9 under stringent conditions.

Another embodiment of the invention provides an isolated nucleic acid molecule which is antisense to a CSAPTP nucleic acid molecule, e.g., the coding strand of a CSAPTP nucleic acid molecule.

Another aspect of the invention provides a vector comprising a CSAPTP nucleic acid molecule. In certain embodiments, the vector is a recombinant expression vector. In another embodiment, the invention provides a host cell containing a vector of the invention. The invention also provides a method for producing a protein, preferably a CSAPTP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant CSAPTP proteins and polypeptides. In one embodiment, the isolated protein, preferably a CSAPTP-1 protein, includes at least one CSAPTP-1 unique N-terminal domain and at least one phosphatase active domain. In another embodiment, the isolated protein, preferably a CSAPTP-1 protein, includes at least one CSAPTP-1 unique N-terminal domain and at least one phosphatase active domain and has an amino acid sequence which is at least 50%, 55%, 60%, 65%, 70%, 75%, 79%, 80%, 85%, 90%, 95%, 99% or more homologous to a amino acid sequence including SEQ ID NO:2. In yet another embodiment, the isolated protein, preferably a CSAPTP-1 protein, includes at least one CSAPTP-1 unique N-terminal domain and at least one phosphatase active domain and is expressed and/or functions in cells of the cardiovascular system. In an even further embodiment, the isolated protein, preferably a CSAPTP-1 protein, includes at least one CSAPTP-1 unique N-terminal domain and at least one phosphatase active domain and plays a role in signalling pathways associated with cellular growth, e.g., signalling pathways associated with cell cycle regulation. In another embodiment, the isolated protein, preferably a CSAPTP-1 protein, includes at least one CSAPTP unique N-terminal domain and at least one phosphatase active domain and is encoded by a nucleic acid molecule having a nucleotide sequence which hybridizes under stringent hybridization conditions to a nucleic acid molecule comprising the nucleotide sequence of SEQ ID NO:1 or SEQ ID NO:3.

In another embodiment, the isolated protein, preferably a CSAPTP-2 protein, includes at least one CSAPTP-2 unique N-terminal domain and at least one phosphatase active domain. In another embodiment, the isolated protein, preferably a CSAPTP-2 protein, includes at least one CSAPTP-2 unique N-terminal domain and at least one phosphatase active domain and has an amino acid sequence which is at least 10%, 15%, 20%, 23%, 25%, 30%, 35%, 40%,45%, 50%, 55%, 60%, 65%, 70%, 75%, 80%, 90%, 95%, 99% or more homologous to an amino acid sequence including SEQ ID NO:5.

In yet another embodiment, the isolated protein, preferably a CSAPTP-2 protein, includes at least one CSAPTP-2 unique N-terminal domain and at least one phosphatase active domain and is expressed and/or functions in cells of the cardiovascular system. In an even further embodiment, the isolated protein, preferably a CSAPTP-2 protein, includes at least one CSAPTP-2 unique N-terminal domain and at least one phosphatase active domain and plays a role in signalling pathways associated with cellular growth, e.g., signalling pathways associated with cell cycle regulation. In another embodiment, the isolated protein, preferably a CSAPTP-2 protein, includes at least one CSAPTP-2 unique N-terminal domain and at least one phosphatase active domain and is encoded by a nucleic acid molecule having a nucleotide sequence which hybridizes under stringent hybridization conditions to a nucleic acid molecule comprising the nucleotide sequence of SEQ ID NO:4 or SEQ ID NO:6.

In yet another embodiment, the isolated protein, preferably a CSAPTP-3 protein, includes at least one CSAPTP-3 unique N-terminal domain and at least one phosphatase active domain. In another embodiment, the isolated protein, preferably a CSAPTP-3 protein, includes at least one CSAPTP-3 unique N-terminal domain and at least one phosphatase active domain and has an amino acid sequence which is at least 10%, 15%, 20%,24%, 25%, 30%, 35%, 40%, 45%, 50%, 55%, 60%, 65%, 70%, 75%, 80%, 85%, 90%, 95%, 99% or more homologous to an amino acid sequence including SEQ ID NO:8.

In yet another embodiment, the isolated protein, preferably a CSAPTP-3 protein, includes at least one CSAPTP-3 unique N-terminal domain and at least one phosphatase active domain and is expressed and/or functions in cells of the cardiovascular system. In an even further embodiment, the isolated protein, preferably a CSAPTP-3 protein, includes at least one CSAPTP-3 unique N-terminal domain and at least one phosphatase active domain and plays a role in signalling pathways associated with cellular growth, e.g., signalling pathways associated with cell cycle regulation. In another embodiment, the isolated protein, preferably a CSAPTP-3 protein, includes at least one CSAPTP-3 unique N-terminal domain and at least one phosphatase active domain and is encoded by a nucleic acid molecule having a nucleotide sequence which hybridizes under stringent hybridization conditions to a nucleic acid molecule comprising the nucleotide sequence of SEQ ID NO:7 or SEQ ID NO:9.

In another embodiment, the isolated protein, preferably a CSAPTP protein, has an amino acid sequence sufficiently homologous to the amino acid sequence of SEQ ID NO:2, SEQ ID NO:5, or SEQ ID NO:8. In a preferred embodiment, the protein, preferably a CSAPTP protein, has an amino acid sequence at least 79%, 23%, 24% or more homologous to an amino acid sequence including SEQ ID NO:2, SEQ ID NO:5, or SEQ ID NO:8, respectively (e.g., the entire amino acid sequence of SEQ ID NO:2, SEQ ID NO:5, or SEQ ID NO:8). In another embodiment, the invention features fragments of the proteins having the amino acid sequence of SEQ ID NO:2, SEQ ID NO:5, or SEQ ID NO:8, wherein the fragment comprises at least 15 amino acids (e.g., contiguous amino acids) of the amino acid sequence of SEQ ID NO:2, SEQ ID NO:5, or SEQ ID NO:8, respectively. In another embodiment, the protein, preferably a CSAPTP protein, has the amino acid sequence of SEQ ID NO:2, SEQ ID NO:5, or SEQ ID NO:8.

Another embodiment of the invention features an isolated protein, preferably a CSAPTP protein, which is encoded by a nucleic acid molecule having a nucleotide sequence at least 40%, 45%, 50%, 55%, 60%, 65%, 70%, 75%, 80%, 85%, 90%, 95%, 99% or more homologous to a nucleotide sequence (e.g., to the entire length of the nucleotide sequence) including SEQ ID NO:1, SEQ ID NO:3, SEQ ID NO:4, SEQ ID NO:6, SEQ ID NO:7, or SEQ ID NO:9, respectively, or a complement thereof. This invention further features an isolated protein, preferably a CSAPTP protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, or SEQ ID NO:9, or a complement thereof.

The proteins of the present invention or biologically active portions thereof, can be operatively linked to a non-CSAPTP polypeptide (e.g., heterologous amino acid sequences) to form fusion proteins. The invention further features antibodies, such as monoclonal or polyclonal antibodies, that specifically bind proteins of the invention, preferably CSAPTP proteins. In addition, the CSAPTP proteins or biologically active portions thereof can be incorporated into pharmaceutical compositions, which optionally include pharmaceutically acceptable carriers.

In another aspect, the present invention provides a method for detecting the presence of a CSAPTP nucleic acid molecule, protein or polypeptide in a biological sample by contacting the biological sample with an agent capable of detecting a CSAPTP nucleic acid molecule, protein or polypeptide such that the presence of a CSAPTP nucleic acid molecule, protein or polypeptide is detected in the biological sample.

In another aspect, the present invention provides a method for detecting the presence of CSAPTP activity in a biological sample by contacting the biological sample with an agent capable of detecting an indicator of CSAPTP activity such that the presence of CSAPTP activity is detected in the biological sample.

In another aspect, the invention provides a method for modulating CSAPTP activity comprising contacting a cell capable of expressing CSAPTP with an agent that modulates CSAPTP activity such that CSAPTP activity in the cell is modulated. In one embodiment, the agent inhibits CSAPTP activity. In another embodiment, the agent stimulates CSAPTP activity. In one embodiment, the agent is an antibody that specifically binds to a CSAPTP protein. In another embodiment, the agent modulates expression of CSAPTP by modulating transcription of a CSAPTP gene or translation of a CSAPTP mRNA. In yet another embodiment, the agent is a nucleic acid molecule having a nucleotide sequence that is antisense to the coding strand of a CSAPTP mRNA or a CSAPTP gene.

In one embodiment, the methods of the present invention are used to treat a subject having a disorder characterized by aberrant CSAPTP protein or nucleic acid expression or activity by administering an agent which is a CSAPTP modulator to the subject. In one embodiment, the CSAPTP modulator is a CSAPTP protein. In another embodiment the CSAPTP modulator is a CSAPTP nucleic acid molecule. In yet another embodiment, the CSAPTP modulator is a peptide, peptidomimetic, or other small molecule. In a preferred embodiment, the disorder characterized by aberrant CSAPTP protein or nucleic acid expression is an immune disorder, an anti-proliferative disorder, a proliferative disorder, e.g., cancer, for example sporadic cancers e.g., brain, breast and prostate; inherited autosomal-dominant cancer, e.g., Cowden's syndrome; renal and lung carcinomas; metabolic disorder, e.g., diabetes, for example, impaired dephosphorylation of both the insulin receptor and insulin receptor substrate 1; viral pathogenesis, e.g., cancer, for example, adenovirus E1A-mediated cell proliferation; e.g., Boubonic Plague, for example, pathogenic *Yersinia pestis* viral PTPase dephosphorylation of host phosphoproteins; a neural disorder, a cardiovascular disorder, e.g., congestive heart failure, or a disorder arising from improper dephosphorylation of phosphorylated protein.

The present invention also provides a diagnostic assay for identifying the presence or absence of a genetic alteration characterized by at least one of (i) aberrant modification or mutation of a gene encoding a CSAPTP protein; (ii) misregulation of the gene; and (iii) aberrant post-translational modification of a CSAPTP protein, wherein a wild-type form of the gene encodes a protein with a CSAPTP activity.

In another aspect the invention provides a method for identifying a compound that binds to or modulates the activity of a CSAPTP protein, by providing an indicator composition comprising a CSAPTP protein having CSAPTP activity, contacting the indicator composition with a test compound, and determining the effect of the test compound on CSAPTP activity in the indicator composition to identify a compound that modulates the activity of a CSAPTP protein.

Other features and advantages of the invention will be apparent from the following detailed description and claims.

BRIEF DESCRIPTION OF THE DRAWINGS

FIG. 1 depicts the cDNA sequence and predicted amino acid sequence of human CSAPTP-1. The nucleotide sequence corresponds to nucleic acids I to 1315 of SEQ ID NO:1. The amino acid sequence corresponds to amino acids 1 to 173 of SEQ ID NO:2. The coding region without the 5' and 3' untranslated regions of the human CSAPTP-1 gene is shown in SEQ ID NO:3.

FIG. 2 depicts the cDNA sequence and predicted amino acid sequence of human CSAPTP-2. The nucleotide sequence corresponds to nucleic acids 1 to 1016 of SEQ ID NO:4. The amino acid sequence corresponds to amino acids 1 to 263 of SEQ ID NO:5. The coding region without the 3' untranslated region of the human CSAPTP-2 gene is shown in SEQ ID NO:6.

FIG. 3 depicts the cDNA sequence and predicted amino acid sequence of human CSAPTP-3. The nucleotide sequence corresponds to nucleic acids 1 to 814 of SEQ ID NO:7. The amino acid sequence corresponds to amino acids 1 to 209 of SEQ ID NO:8. The coding region without the 3' untranslated region of the human CSAPTP-3 gene is shown in SEQ ID NO:9.

FIG. 4 depicts a global alignment between the CSAPTP-1 DNA sequence and the human protein tyrosine phosphatase DNA sequence (Accession No. AAB40597) DNA sequence. This alignment were generated utilizing the ALIGN program with the following parameter setting: PAM120, gap penalties: −121/−4 (Myers, E. and Miller, W. (1988) "Optimal Alignments in Linear Space" CABIOS 4:11–17). The results showed a 38.7% identity between the two sequences.

FIG. 5 depicts a global alignment between the CSAPTP-1 protein sequence and the human protein tyrosine phosphatase DNA sequence (Accession No. AAB40597) protein sequence. This alignment was generated utilizing the ALIGN program with the following parameter setting: PAM120, gap penalties: −12/−4 (Myers, E. and Miller, W. (1988) "Optimal Alignments in Linear Space" CABIOS 4:11–17). The results showed a 78.6% idenitiy between the two sequences.

FIG. 6 depicts a global alignment between the CSAPTP-2 protein sequence and the human dual specificity phosphatase (SwissProt: P51452) protein sequence. This alignment was generated utilizing the ALIGN program with the following parameter setting: PAM120, gap penalties: −12/−4 (Myers, E. and Miller, W. (1988) "Optimal Alignments in Linear Space" CABIOS 4:11–17). The results showed a 22.5% identity between the two sequences.

FIG. 7 depicts a global alignment between the CSAPTP-3 protein sequence and the SwissProt: Z68315 protein sequence. This alignment was generated utilizing the ALIGN program with the following parameter setting: PAM120, gap penalties: −12/−4 (Myers, E. and Miller, W. (1988) "Optimal Alignments in Linear Space" CABIOS 4:11–17). The results showed a 24% identity between the two sequences.

DETAILED DESCRIPTION OF THE INVENTION

The present invention is based, at least in part, on the discovery of novel molecules, referred to herein as "Cardiovascular System Associated Protein Tyrosine Phosphatase" or "CSAPTP" nucleic acid and polypeptide molecules, which play a role in or function in a variety of cellular processes, e.g., proliferation, anti-proliferative mechanisms, immune responses, viral replication in a host, viral pathogenicity, neuroprotective responses, insulin responses, and cardiac cellular processes. In one embodiment, the CSAPTP molecules of the present invention modulate the activity of one or more proteins involved in a proliferative disorder, e.g., cancer. In another embodiment, the CSAPTP molecules of the present invention modulate the activity of one or more proteins involved in an immune cell disorder. In another embodiment, the CSAPTP molecules of the present invention modulate the activity of one or more proteins involved in viral replication and/or viral pathogenesis in a host. In another embodiment, the CSAPTP molecules of the present invention modulate the activity of one or more proteins involved in a neuroprotective response, e.g., neuronal response to ischemic injury. In another embodiment, the CSAPTP molecules of the present invention modulate the activity of one or more proteins involved in a metabolic disorder, e.g., diabetes. In one embodiment, the CSAPTP molecules of the present invention modulate the activity of one or more proteins involved in a cardiovascular disorder, e.g., congestive heart failure. In another embodiment, the CSAPTP molecules of the present invention are capable of modulating the phosphorylation state of a CSAPTP molecule or one or more proteins involved in cellular growth or differentiation, e.g., cardiac cell growth or differentiation.

As used herein, the term "protein tyrosine phosphatase" or "PTPase" includes a protein or polypeptide (e.g., an enzyme) which is capable of facilitating (e.g., catalyzing) the removal of a phosphate group attached to a tyrosine, serine or threonine residue of a protein or polypeptides (e.g., a phosphoprotein). As referred to herein, a protein tyrosine phosphatase includes at least one catalytic domain having a specificity for (i.e. a specificity to dephosphorylating tyrosine residues or both serine/threonine residues and tyrosine residues (e.g., the dual specificity PTPases) and including at least about 200–400 amino acid residues in length, preferably about 200–300 amino acid residues in length, and more preferably about 250–300 amino acid residues in length. Phosphatases of the present invention preferably include a catalytic domain which includes at least one conserved motif or subdomain having at least about 30–50 amino acid residues, more preferably 40 amino acid residues which are conserved among PTPases. PTPases can be either soluble or membrane bound (see e.g., Brautigan Biochem. biophys. Acta, 1114 (1992) 63–77; Charbonneau Ann. Rev. Cell Biol., 8 (1992) 463–493; Fisher et al. Science, 253 (1991) 401–406; Hunter Cell, 58 (1989) 1013–1016).

Membrane bound PTPases typically contain receptor-like extracellular regions connected to the intracellular (catalytic) domains by a short transmembrane segment (Streuli and Saito, 1993, Adv Prot Phosphatases 7:67–94). The non-transmembrane (cytoplasmic) PTPases typically include at least one catalytic domain (Koch et al., 1991, Science 252:668–674).

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases.

As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) American Family Physician 57:1901–04, the contents of which are incorporated herein by reference.

As used herein, the term "cardiac cellular processes" includes intra-cellular or inter-cellular processes involved in the functioning of the heart. Cellular processes involved in the nutrition and maintenance of the heart, the development of the heart, or the ability of the heart to pump blood to the rest of the body are intended to be covered by this term. Such processes include, for example, cardiac muscle contraction, distribution and transmission of electrical impulses, and cellular processes involved in the opening and closing of the cardiac valves. The term "cardiac cellular processes" further includes processes such as the transcription, translation and post-translational modification of proteins involved in the functioning of the heart, e.g., myofilament specific proteins, such as troponin I, troponin T, myosin light chain 1 (MLC1), and α-actinin.

The present invention is based, at least in part, on the discovery of novel molecules, referred to herein as CSAPTP protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features CSAPTP nucleic acid molecules, preferably human CSAPTP molecules, e.g., CSAPTP-1, CSAPTP-2, and CSAPTP-3, which were identified from cDNA libraries made from hearts of patients with congestive heart failure (CHF) of ischemic and idiopathic origin. The CSAPTP nucleic acid and protein molecules of the invention are described in further detail in the following subsections.

A. The CSAPTP-1 Nucleic Acid and Protein Molecules

One embodiment of the invention features CSAPTP-1 proteins and nucleic acid molecules which have sequence similarity with protein-tyrosine phosphatases. Accordingly, CSAPTP-1 polypeptides of the invention may interact with (e.g., bind to) at least one ligand which is a phosphorylated tyrosine of a protein and, thus, may be involved in the regulation of proliferation, anti-proliferative mechanisms, immune responses, viral replication in a host, viral pathogenicity, neuroprotective responses, insulin responses, and cardiac cellular processes.

In one embodiment, the isolated proteins of the present invention, preferably CSAPTP-1 proteins, are identified based on the presence of a CSAPTP-1 unique N-terminal domain and at least one phosphatase active domain. As used herein, a "CSAPTP-1 unique N-terminal domain" includes a protein domain which is at least about 60–110 amino acid residues in length, preferably at least 70–100 amino acid residues in length, more preferably at least 75–95, or at least 80–90, or preferably 86 amino acid residues in length. In another embodiment, a CSAPTP-1 unique N-terminal domain has at least 65–95%, preferably at least 70–90%, and more preferably at least 75–85% homology with the amino acid sequence of a CSAPTP-1 unique N-terminal domain of a human CSAPTP-1 sequence set forth in SEQ ID NO:2 (e.g., amino acid residues 83–169 of the amino acid sequence as set forth in SEQ ID NO:2). As further defined herein, a CSAPTP-1 unique N-terminal domain of a CSAPTP-1 protein family member, however, is not sufficiently homologous to the amino acid sequence of a member of another protein family, such as a non-CSAPTP-1 protein family. In a preferred embodiment, a CSAPTP-1 unique N-terminal domain has amino acid residues 83–169 of SEQ ID NO:2.

In another embodiment of the invention, a CSAPTP-1 family member is identified based on the presence of a phosphatase active domain. As used herein, a "phosphatase active domain" includes a protein domain which is at least 60–110 amino acid residues in length, preferably at least 70–100 amino acid residues in length, and more preferably at least 75–95, or at least 80–90, or preferably 86 amino acid residues in length, which is conserved in phosphatases which dephosphorylate tyrosine, serine, or threonine residues and is found in the catalytic domain of PTPases. A phosphatase active domain is capable of facilitating (e.g., catalyzing) the removal of a phosphate group attached to a tyrosine, serine or threonine residue of a protein (e.g., a phosphoprotein)

In one embodiment, a phosphatase active domain has at least 65–95%, preferably at least 70–90%, and more preferably at least 75–85% homology with the amino acid sequence of a phosphatase active domain of a human CSAPTP-1 sequence set forth in SEQ ID NO:2. In another embodiment, a phosphatase active domain has amino acid residues 68–173 of the amino acid sequence as set forth in SEQ ID NO:2. Phosphatase active domains are described in, for example, Charbonneau, H. and Tonks, N. K. (1992) *Ann. Rev. Cell Biol.* 8:463–493, and Zhang, Z (1998) *Crit. Rev. Biochem. Mol. Biol.* 33(1):1–52, the contents of which are incorporated herein by reference. As further defined herein, a phosphatase active domain of a CSAPTP-1 protein family member, however, is not sufficiently homologous to the amino acid sequence of a member of another protein family, such as a non-CSAPTP-1 protein family.

In another embodiment of the invention, a CSAPTP-1 family member is identified based on the presence of at least one phosphatase extended catalytic active domain within a phosphatase active domain. As used herein, a "phosphatase extended catalytic active domain" includes a protein domain which is at least 5–50 amino acid residues in length, preferably at least 10–40 amino acid residues in length, more preferably at least 15–25, or at least 20–22, or preferably 21 amino acid residues in length which is conserved in phosphatases which dephosphorylate tyrosine, serine, or threonine residues and found in the catalytic domain of PTPases. A phosphatase extended catalytic active domain is capable of facilitating (e.g., catalyzing) the removal of a phosphate group attached to a tyrosine, serine or threonine residue of a protein (e.g., a phosphoprotein). Preferably, the phosphatase extended catalytic active domain includes the following amino acid consensus sequence (VXVHCXAGXSRSXTX (3) AYLM, X=any amino acid) (SEQ ID NO:10). In another embodiment, a phosphatase extended catalytic active domain has at least 65–95%, preferably at least 70–90%, and more preferably at least 75–85% homology with the amino acid sequence of a phosphatase extended catalytic active domain of a human CSAPTP-1 sequence set forth in SEQ ID NO:2 (e.g., amino acid residues 100–120). In another embodiment, a phosphatase extended catalytic active domain has amino acid residues 100–120 of the amino acid sequence as set forth in SEQ ID NO:2. Phosphatase extended catalytic active domains are described in, for example, Ramponi G. and Stefani, M (1997) *Int. J. Biochem. Cell Biol.* 29(2):279–292, the contents of which are incorporated herein by reference. As further defined herein, a phosphatase extended catalytic active domain of a CSAPTP-1 protein family member, however, is not sufficiently homologous to the amino acid sequence of a member of another protein family, such as a non-CSAPTP-1 protein family.

In another embodiment of the invention, a CSAPTP-1 family member is identified based on the presence of at least one phosphatase catalytic active domain within a phosphatase active domain. As used herein, a "phosphatase catalytic active domain" includes a protein domain which is at least 5–20 amino acid residues in length, preferably at least 7–15 amino acid residues in length, and more preferably at least 8–12, or at least 9–11, or preferably 10 amino acid residues in length which is conserved in phosphatases which dephosphorylate tyrosine, serine, or threonine residues and found in the catalytic domain of PTPases. A phosphatase catalytic active domain is capable of facilitating (e.g., catalyzing) the removal of a phosphate group attached to a tyrosine, serine or threonine residue of a protein (e.g., a phosphoprotein). Preferably, the phosphatase catalytic active domain includes the following amino acid consensus sequence ([I/V] HCXAGXXR [S/T] X=any amino acid) (SEQ ID NO:11). In another embodiment, a phosphatase catalytic active domain has at least 65–95%, preferably at least 70–90%, and more preferably at least 75–85% homology with the amino acid sequence of a phosphatase catalytic active domain of a human CSAPTP-1 sequence set forth in SEQ ID NO:2 (e.g., amino acid residues 102–111). Preferably, a phosphatase catalytic active domain has amino acid residues 102–111 of the amino acid sequence as set forth in SEQ ID NO:2. Phosphatase catalytic active domains are described in, for example, Keyse, S. M. (1995) *Biochimica et Biophysica Acta* 1265:152–160, the contents of which are incorporated herein by reference. As further defined herein, a phosphatase catalytic active domain of a CSAPTP-1 protein family member, however, is not sufficiently homologous to the amino acid sequence of a member of another protein family, such as a non-CSAPTP-1 protein family.

In another embodiment of the invention, a CSAPTP-1 family member is identified based on the presence of at least one phosphatase catalytic core active domain within a phosphatase active domain. As used herein, a "phosphatase catalytic core active domain" includes a protein domain which is at least 5–15 amino acid residues in length, preferably at least 7–11, or at least 8–10, or preferably 9 amino acid residues in length which is conserved in phosphatases which dephosphorylate tyrosine, serine, or threonine residues and found in the catalytic domain of PTPases. A phosphatase catalytic core active domain is capable of facilitating (e.g., catalyzing) the removal of a phosphate group attached to a tyrosine, serine or threonine residue of a protein (e.g., a phosphoprotein). Preferably, the phosphatase catalytic core active domain includes the following amino acid consensus sequence (H/V)C(X)$_5$R(S/T), X=any amino acid) (SEQ ID NO:12). In another embodiment, a phosphatase catalytic core active domain has at least 65–95%, preferably at least 70–90%, and more preferably at least 75–85% homology with the amino acid sequence of a phosphatase catalytic core active domain of a human CSAPTP-1 sequence set forth in SEQ ID NO:2 (e.g., amino acid residues 103–111). Preferably, a phosphatase catalytic core active domain has amino acid residues 103–111 of the amino acid sequence as set forth in SEQ ID NO:2. Phosphatase catalytic core active domains are described in, for example, Misra-Press, A et al (1995) *J Biol. Chem.* 270(24):14587–14596, the contents of which are incorporated herein by reference. As further defined herein, a phosphatase catalytic core active domain of a CSAPTP-1 protein family member, however, is not sufficiently homologous to the amino acid sequence of a member of another protein family, such as a non-CSAPTP-1 protein family.

In another embodiment of the invention, a CSAPTP-1 family member is identified based on the presence of at least one phosphatase catalytic invariant core active domain within the phosphatase active domain. As used herein, a "phosphatase catalytic invariant core active domain" includes a protein domain which is at least 4–15 amino acid residues in length, preferably at least 5–11 amino acid residues in length, and more preferably at least 6–10, or at least 8–9, or preferably 7 amino acid residues in length which is conserved in phosphatases which dephosphorylate tyrosine, serine, or threonine residues and found in the catalytic domain of PTPases. A phosphatase catalytic invariant core active domain is capable of facilitating (e.g., catalyzing) the removal of a phosphate group attached to a tyrosine, serine or threonine residue of a protein (e.g., a phosphoprotein). Preferably, the phosphatase catalytic invariant core active domain includes the following amino acid consensus sequence (C(X)$_5$R, X=any amino acid) (SEQ ID NO:13). In another embodiment, a phosphatase catalytic invariant core active domain has at least 65–95%, preferably at least 70–90%, and more preferably at least 75–85% homology with the amino acid sequence of a phosphatase catalytic invariant core active domain of a human CSAPTP-1 sequence set forth in SEQ ID NO:2 (e.g., amino acid residues 104–110). In another embodiment, a phosphatase catalytic invariant core active domain has amino acid residues 104–110 of the amino acid sequence as set forth in SEQ ID NO:2. Phosphatase catalytic invariant core active domains are described in, for example, Misra-Press, A et al (1995) *J Biol. Chem.* 270(24): 14587–14596, the contents of which are incorporated herein by reference. As further defined herein, a phosphatase catalytic invariant core active domain of a CSAPTP-1 protein family member, however, is not sufficiently homologous to the amino acid sequence of a member of another protein family, such as a non-CSAPTP-1 protein family.

In another embodiment of the invention, a CSAPTP-1 family member is identified based on the presence of an intradomain disulfide bond consensus sequence. As used herein, an "intradomain disulfide bond consensus sequence" includes a protein domain which is at least 3–20 amino acid residues in length, preferably at least 3–15 amino acid residues in length, and more preferably at least 5–9, or at least 6–8, or preferably 7 amino acid residues in length, and is the site of cysteine-cysteine bonding within a single protein molecule. In one embodiment, an intradomain disulfide bond consensus sequence has at least 65–95%, preferably at least 70–90%, and more preferably at least 75–85% homology with the amino acid sequence of an intradomain disulfide bond consensus sequence of a human CSAPTP-1 sequence set forth in SEQ ID NO:2 (e.g., amino acid residues 97–103). In another embodiment, an intradomain disulfide bond consensus sequence has amino acid residues 97–103 of the amino acid sequence as set forth in SEQ ID NO:2. Intradomain disulfide bond consensus sequence domains are described in, for example, Beck, S. and Barrel, B. G. (1988) *Nature* 331:269–272, the contents of which are incorporated herein by reference. As further defined herein, an intradomain disulfide bond consensus sequence of a CSAPTP-1 protein family member, however, is not sufficiently homologous to the amino acid sequence of a member of another protein family, such as a non-CSAPTP-1 protein family.

In another embodiment, CSAPTP-1 family members include at least 1, 2, or more Protein kinase C (PKC) phosphorylation sites. PKC phosphorylation sites can be found at least within the amino acid sequence 1 to 173 of SEQ ID NO:2. CSAPTP-1 family members can further include at least 1, 2, 3, 4 or more Casein kinase II phosphorylation sites. Casein kinase II phosphorylation sites can be found at least within the amino acid sequence 83–255 of SEQ ID NO:2. CSAPTP-1 family members can further include at least one Tyrosine kinase phosphorylation site. Tyrosine kinase phosphorylation sites can be found at least within the amino acid sequence 83–255 of SEQ ID NO:2. CSAPTP-1 family members can further include at least 1, 2 or more N-glycosylation sites. N-glycosylation sites can be found at least within the amino acid sequence 83–255 of SEQ ID NO:2. CSAPTP-1 family members can further include at least 1, 2 or more N-myristoylation sites. N-myristoylation sites can be found at least within the amino acid sequence 83–255 of SEQ ID NO:2. CSAPTP-1 family members can further include at least 1, 2 or more homeobox domains. Homeobox domains can be found at least within the amino acid sequence 83–255 of SEQ ID NO:2. Wherein the site(s) have a consensus sequence selected from: [ST]-X-[RK], where S or T is a phosphorylation site (SEQ ID NO:15); [RK]-X (2)-[DE]-X (3)-Y (SEQ ID NO:16) (see PROSITE document for alternative consensus sequences); N-{P}-[ST]-{P}, where N is a glycosylation site (SEQ ID NO:17); G-{EDRKHPFYW}-X (2)-[STAGCN]-{P}, where G is an N-myristoylation site (SEQ ID NO:18); and [ST]-X (2)-[DE], where S or T is a phosphorylation site, respectively (SEQ ID NO:19). X designates any amino acid; (n) designates an alphanumeric number of "n" amino acids. These sites are further described in PROSITE Documents, Accession No. PDOC00005, PDOC00007, PDOC00001, PDOC00008, PDOC00006, respectively (http://expasy.hcuge.ch/cgi-bin/get-prodoc-entry?PDOC00005, PDOC00007, PDOC00001, PDOC00008, PDOC00006, respectively) and as PROSITE Accession No. PS00005, PS00007, PS00001, PS00008, PS00006, respectively.

Isolated proteins of the present invention, preferably CSAPTP-1 proteins, have an amino acid sequence sufficiently homologous to the amino acid sequence of SEQ ID NO:2 or are encoded by a nucleotide sequence which includes a nucleotide sequence sufficiently homologous to SEQ ID NO:1, SEQ ID NO:3. As used herein, the term "sufficiently homologous" includes a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30–40% homology, preferably 40–50% homology, more preferably 50–60%, and even more preferably 60–70%, 70–80%, or 80–90% homology across the amino acid sequences of the domains and contain at least one and preferably two structural domains or motifs, are defined herein as sufficiently homologous. Furthermore, amino acid or nucleotide sequences which share at least 30–40%, preferably 40–50%, more preferably 50–60%, 60–70%, 70–80%, or 80–90% homology and share a common functional activity are defined herein as sufficiently homologous.

Accordingly, another embodiment of the invention features isolated CSAPTP-1 proteins and polypeptides having a CSAPTP-1 activity. Preferred proteins are CSAPTP-1 proteins having at least one CSAPTP-1 unique N-terminal domain and at least one PTPase active domain. Additional preferred proteins are CSAPTP-1 proteins having at least a CSAPTP-1 unique N-terminal domain, at least one phosphatase active domain, at least one phosphatase extended catalytic active domain, and at least one phosphatase catalytic active domain. Yet other preferred proteins are CSAPTP-1 proteins having at least a CSAPTP-1 unique N-terminal domain, at least one phosphatase active domain, at least one phosphatase extended catalytic active domain, at least one phosphatase catalytic active domain, and at least one phosphatase catalytic core active domain. Other preferred proteins are CSAPTP-1 proteins having at least a CSAPTP-1 unique N-terminal domain, at least one phosphatase active domain, at least one phosphatase extended catalytic active domain, and at least one phosphatase catalytic active domain, at least one phosphatase catalytic core active domain, at least one phosphatase catalytic invariant core active domain. Further preferred proteins are CSAPTP-1 proteins having at least a CSAPTP-1 unique N-terminal domain, at least one phosphatase active domain, and at least one intradomain disulfide bond consensus sequence. Other preferred proteins are CSAPTP-1 proteins having at least a CSAPTP-1 unique N-terminal domain, at least one phosphatase active domain, and a CAAX consensus sequence.

The nucleotide sequence of the isolated human CSAPTP-1 cDNA and the predicted amino acid sequence of the human CSPATP-1 polypeptide are shown in FIG. 1 and in SEQ ID NOs:1, 3 and 2, respectively. The CSAPTP-1 gene, which is approximately 1311 nucleotides in length, encodes a protein having a molecular weight of approximately 19 kD and which is approximately 173 amino acid residues in length. CSAPTP-1 message was detected in human heart and skeletal, in all rat tissues but predominantly in rat skeletal, heart, placenta, lung and brain.

In a preferred embodiment, CSAPTP-1 proteins of the invention have an amino acid sequence of about 50–100, more preferably about 100–150, and even more preferably about 150–200 or 173 amino acid residues in length.

B. The CSAPTP-2 Nucleic Acid and Protein Molecules

In another embodiment, isolated proteins of the present invention, preferably CSAPTP-2 proteins, are identified based on the presence of a CSAPTP-2 unique N-terminal domain and at least one phosphatase active domain as defined herein. As used herein, a "CSAPTP-2 unique N-terminal domain" includes a protein domain which is at least 110–130 amino acid residues in length, preferably at least 115–145 amino acid residues in length, more preferably at least 120–140, or at least 125–135, or preferably 131 amino acid residues in length. In another embodiment, a CSAPTP-2 unique N-terminal domain has at least 65–95%, preferably at least 70–90%, and more preferably at least 75–85% homology with the amino acid sequence of a CSAPTP-2 unique N-terminal domain of a human CSAPTP-2 sequence set forth in SEQ ID NO:5 (e.g., amino acid residues 1–131 of the amino acid sequence as set forth in SEQ ID NO:5). As further defined herein, a CSAPTP-2 unique N-terminal domain of a CSAPTP-2 protein family member, however, is not sufficiently homologous to the amino acid sequence of a member of another protein family, such as a non-CSAPTP-2 protein family. Preferably, a "CSAPTP-2 unique N-terminal domain" has amino acid residues 1-131 of SEQ ID NO:5.

In yet another embodiment, the isolated CSAPTP-2 proteins are identified based on the presence of a CSAPTP-2 unique N-terminal domain, at least one phosphatase active domain, and at least one phosphatase extended catalytic active domain. In yet another embodiment, the isolated CSAPTP-2 proteins are identified based on the presence of a CSAPTP-2 unique N-terminal domain, at least one phosphatase active domain, at least one phosphatase extended catalytic active domain and at least one phosphatase catalytic active domain. In yet another embodiment, the isolated CSAPTP-2 proteins are identified based on the presence of a CSAPTP-2 unique N-terminal domain, at least one phosphatase active domain, at least one phosphatase extended catalytic active domain, at least one phosphatase catalytic active domain and at least one phosphatase catalytic core active domain. In yet another embodiment, the isolated CSAPTP-2 proteins are identified based on the presence of a CSAPTP-2 unique N-terminal domain and at least one phosphatase active domain, at least one phosphatase extended catalytic active domain, at least one phosphatase catalytic active domain, at least one phosphatase catalytic core active domain, at least one phosphatase catalytic invariant core active domain, each of the above domains are described herein.

In a preferred embodiment, a CSAPTP-2 unique N-terminal domain includes amino acids 1–131. In another embodiment, a CSAPTP-2 phosphatase active domain includes amino acid residues 132–263. In another embodiment, a CSAPTP-2 phosphatase extended catalytic active domain includes amino acid residues 105–125. In another embodiment, a CSAPTP-2 phosphatase catalytic active domain includes amino acid residues 107–116. In another embodiment, a CSAPTP-2 phosphatase catalytic core active domain includes amino acid residues 108–116. In another embodiment, a CSAPTP-2 phosphatase catalytic invariant core active domain includes amino acid residues 109–115.

In another embodiment, CSAPTP-2 family members include at least 1, 2, 3 or more Protein kinase C (PKC) phosphorylation sites. PKC phosphorylation sites can be found at least within the amino acid sequence 1–263 of SEQ ID NO:5. CSAPTP-2 family members can further include at least 1, 2, 3, 4 or more Casein kinase II phosphorylation sites. Casein kinase II phosphorylation sites can be found at least within the amino acid sequence 1–263 of SEQ ID NO:8. CSAPTP-2 family members can further include at least one amidation site. Amidation sites can be found at least within the amino acid sequence 1–263 of SEQ ID NO:8. CSAPTP-2 family members can further include at least 1 or more N-glycosylation sites. N-glycosylation sites can be found at least within the amino acid sequence 1–263 of SEQ ID NO:5. CSAPTP-2 family members can further include at least 1, 2, 3, 4, 5 or more N-myristoylation sites. N-myristoylation sites can be found at least within the amino acid sequence 1–263 of SEQ ID NO:5. CSAPTP-2 family members can further include at least 1, 2 or more helix-loop-helix DNA-binding domains. Helix-loop-helix DNA-binding domains can be found at least within the amino acid sequence 1–263 of SEQ ID NO:5.

Isolated proteins of the present invention, preferably CSAPTP-2 proteins, have an amino acid sequence sufficiently homologous to the amino acid sequence of SEQ ID NO:5 or are encoded by a nucleotide sequence which includes a nucleotide sequence sufficiently homologous to SEQ ID NO:4, SEQ ID NO:6. As used herein, the term "sufficiently homologous" includes a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30–40% homology, preferably 40–50% homology, more preferably 50–60%, and even more preferably 60–70%, 70–80%, or 80–90% homology across the amino acid sequences of the domains and contain at least one and preferably two structural domains or motifs, are defined herein as sufficiently homologous. Furthermore, amino acid or nucleotide sequences which share at least 30–40%, preferably 40–50%, more preferably 50–60%, 60–70%, 70–80%, or 80–90% homology and share a common functional activity are defined herein as sufficiently homologous.

Accordingly, another embodiment of the invention features isolated CSAPTP-2 proteins and polypeptides having a CSAPTP-2 activity as defined herein.

The nucleotide sequence of the isolated human CSAPTP-2 cDNA and the predicted amino acid sequence of the human CSPATP-2 polypeptide are shown in FIG. 2 and in SEQ ID NOs:4,6 and 5, respectively.

The CSAPTP-2 gene, which is approximately 1016 nucleotides in length, encodes a protein having a molecular weight of approximately 29 kD and which is approximately 263 amino acid residues in length. CSAPTP-2 message was detected in human with highest expression in skeletal muscle with some expression in heart and brain muscle, while in the rat expression was mainly found in skeletal muscle.

In a preferred embodiment, CSAPTP-2 proteins of the invention have an amino acid sequence of about 50–100, more preferably about 100–200, more preferably about 200–250, and even more preferably about 250–300 or 263 amino acid residues in length.

C. The CSAPTP-3 Nucleic Acid and Protein Molecules

In another embodiment, the isolated proteins of present invention, preferably CSAPTP-3 proteins, are identified based on the presence of a CSAPTP-3 unique N-terminal domain and at least one phosphatase active domain. As used herein, a "CSAPTP-3 unique N-terminal domain" includes a protein domain which is at least 100–110 amino acid residues in length, preferably at least 95–115 amino acid residues in length, more preferably at least 90–120, or at least 85–125, or preferably 104 amino acid residues in length. In another embodiment, a CSAPTP-3 unique N-terminal domain has at least 65–95%, preferably at least 70–90%, and more preferably at least 75–85% homology with the amino acid sequence of a CSAPTP-3 unique N-terminal domain of a human CSAPTP-3 sequence set forth in SEQ ID NO:5 (e.g., amino acid residues 1–104 of the amino acid sequence as set forth in SEQ ID NO:5). As further defined herein, a CSAPTP-3 unique N-terminal domain of a CSAPTP-3 protein family member, however, is not sufficiently homologous to the amino acid sequence of a member of another protein family, such as a non-CSAPTP-3 protein family. Preferably, a "CSAPTP-3 unique N-terminal domain" has amino acid residues 1–104 of SEQ ID NO:8.

Accordingly, another embodiment of the invention features isolated CSAPTP-3 proteins and polypeptides having a CSAPTP-3 activity. Preferred proteins are CSAPTP-3 proteins having at least a CSAPTP-3 unique N-terminal domain and at least one phosphatase active domain and, optionally, at least one intradomain disulfide bond consensus sequence. Other preferred proteins are CSAPTP-3 proteins having at least a CSAPTP-3 unique N-terminal domain and at least one phosphatase active domain, and at least one phosphatase extended catalytic active domain. Yet other preferred proteins are CSAPTP-3 proteins having at least a CSAPTP-3 unique N-terminal domain, at least one phosphatase active domain, at least one phosphatase extended catalytic active domain, and at least one phosphatase catalytic active domain. Additionally, preferred proteins are CSAPTP-3 proteins having at least a CSAPTP-3 unique N-terminal domain, at least one phosphatase active domain, at least one phosphatase extended catalytic active domain, at least one phosphatase catalytic active domain, and at least one phosphatase catalytic core active domain. Yet other preferred proteins are CSAPTP-3 proteins having at least a CSAPTP-3 unique N-terminal domain, at least one phosphatase extended catalytic active domain, at least one phosphatase catalytic active domain, at least one phosphatase catalytic core active domain, and at least one phosphatase catalytic invariant core active domain.

The CSAPTP-3 unique N-terminal domain, the intradomain disulfide bond consensus sequence, the phosphatase active domain, the phosphatase extended catalytic active domain, the phosphatase catalytic active domain, the phosphatase catalytic core active domain, and the phosphatase catalytic invariant core active domain are described herein. In a preferred embodiment, a CSAPTP-3 unique N-terminal domain includes amino acid residues 1–104. In another embodiment, a CSAPTP-3 disulfide bond consensus sequence includes amino acid residues 131–137. In another embodiment, a CSAPTP-3 phosphatase active domain includes amino acid residues 105–209. In another embodiment, a CSAPTP-3 phosphatase extended catalytic active domain includes amino acid residues 134–154. In another embodiment, a CSAPTP-3 phosphatase catalytic active domain includes amino acid residues 136–145. In another embodiment, a CSAPTP-3 phosphatase catalytic core active domain includes amino acid residues 137–145. In another embodiment, a CSAPTP-3 phosphatase catalytic invariant core active domain includes amino acid residues 138–144.

In another embodiment, CSAPTP-3 family members include at least 1, 2, 3 or more Protein kinase C (PKC) phosphorylation sites. PKC phosphorylation sites can be found at least within the amino acid sequence 1–209 of SEQ ID NO:8. CSAPTP-3 family members can further include at least 1, 2, 3 or more Casein kinase II phosphorylation sites. Casein kinase II phosphorylation sites can be found at least within the amino acid sequence 1–209 of SEQ ID NO:8. CSAPTP-3 family members can further include at least one cAMP and cGMP dependent protein kinase phosphorylation site. cAMP and cGMP dependent protein kinase phosphorylation sites can be found at least within the amino acid sequence 1–209 of SEQ ID NO:8. CSAPTP-3 family members can further include at least one or more N-glycosylation sites. N-glycosylation sites can be found at least within the amino acid sequence 1–209 of SEQ ID NO:8. CSAPTP-3 family members can further include at least 1, 2, 3, 4 or more N-myristoylation sites. N-myristoylation sites can be found at least within the amino acid sequence 1–209 of SEQ ID NO:8. CSAPTP-3 family members can further include at least 1, 2 or more transcription factor TFIIB repeats. Transcription factor TFIIB repeats can be found at least within the amino acid sequence 1–209 of SEQ ID NO:8.

Isolated proteins of the present invention, preferably CSAPTP-3 proteins, have an amino acid sequence sufficiently homologous to the amino acid sequence of SEQ ID NO:8 or are encoded by a nucleotide sequence which includes a nucleotide sequence sufficiently homologous to SEQ ID NO:7, SEQ ID NO:9. As used herein, the term "sufficiently homologous" includes a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30–40% homology, preferably 40–50% homology, more preferably 50–60%, and even more preferably 60–70%, 70–80%, or 80–90% homology across the amino acid sequences of the domains and contain at least one and preferably two structural domains or motifs, are defined herein as sufficiently homologous. Furthermore, amino acid or nucleotide sequences which share at least 30–40%, preferably 40–50%, more preferably 50–60%, 60–70%, 70–80%, or 80–90% homology and share a common functional activity are defined herein as sufficiently homologous.

The nucleotide sequence of the isolated human CSAPTP-3 cDNA and the predicted amino acid sequence of the human CSPATP-2 polypeptide are shown in FIG. 3 and in SEQ ID NOs:7,9 and 8, respectively. The CSAPTP-3 gene, which is approximately 814 nucleotides in length, encodes a protein having a molecular weight of approximately 23 kD and which is approximately 209 amino acid residues in length. CSAPTP-3 message was detected in human in highest in heart and skeletal and also found in brain, placenta, kidney and pancreas.

In a preferred embodiment, CSAPTP-3 proteins of the invention have an amino acid sequence of about 50–100, more preferably about 100–200, and even more preferably about 200–250 or 209 amino acid residues in length.

D. CSAPTP Activities

As used interchangeably herein, a "CSAPTP activity", "biological activity of CSAPTP" or "functional activity of CSAPTP", includes an activity exerted by a CSAPTP protein, polypeptide or nucleic acid molecule as determined in vivo, in vitro, or in situ, according to standard techniques. In one embodiment, a CSAPTP activity is a direct activity, such as an association with a CSAPTP-target molecule. As used herein, a "target molecule" is a molecule with which a CSAPTP protein binds or interacts in nature, such that CSAPTP-mediated function is achieved. A CSAPTP target molecule can be a CSAPTP protein or polypeptide of the present invention or a non-CSAPTP molecule. For example, a CSAPTP target molecule can be a non-CSAPTP protein molecule. Alternatively, a CSAPTP activity is an indirect activity, such as an activity mediated by interaction of the CSAPTP protein with a CSAPTP target molecule such that the target molecule modulates a downstream cellular activity (e.g., interaction of an CSAPTP molecule with a CSAPTP target molecule can modulate the activity of that target molecule on an immune cell).

In a preferred embodiment, a CSAPTP activity is at least one or more of the following activities: (i) interaction of a CSAPTP protein with a CSAPTP target molecule; (ii) interaction of a CSAPTP protein with a CSAPTP target molecule, wherein the CSAPTP target is a ligand, e.g., phosphorylated amino acid residue of a phosphorylated protein (e.g., a phosphatase, for example, a cell cycle regulatory phosphatase, e.g., Cdc25A phosphatase, a cell cycle phosphatase which regulates the G1/S-phase transition, a CSAPTPase), a kinase (e.g., Mitogen Activating Protein (MAP) kinase, or a Cardiovascular associated Protein Tyrosine Kinase (CSAPTK)); (iii) interaction of a CSAPTP protein with a CSAPTP target molecule, wherein the CSAPTP target is a receptor, e.g., insulin receptor, insulin receptor substrate 1; (iv) interaction of a CSAPTP protein with a CSAPTP target molecule, wherein the CSAPTP target is a viral protein, e.g., vaccinia viral transcription-mediating proteins, Myxoma viral proteins, Shope Fibroma viral proteins, *Leishmania donovani, Trypanosoma brucei* and *Trypanosoma cruzi* viral proteins.

In yet another preferred embodiment, a CSAPTP activity is at least one or more of the following activities: (1) regulation of cell cycle, e.g., dephosphorylation of phosphorylated proteins involved in the cell cycle, e.g., dephosphorylation of phosphorylated proteins involved in the cell cycle, e.g., proliferation-mediating proteins, e.g., Cdc25A, a cell cycle phosphatase which regulates the G1/S-phase transition, e.g., anti-proliferative proteins, either in vitro, in vivo or in situ; (2) mediation of the viral pathogenicity, e.g., viral phosphatase mediated dephosphorylation of host phosphorylated proteins, for example, viral induced disease, e.g., Yersinia pathogenesis, for example, *Yersinia pestis* (Bubonic Plague), e.g., viral phosphatase mediated dephosphorylation of host anti-proliferative phosphorylated proteins, for example, viral induced proliferative diseases, e.g., viral induced cancers, either in vitro, in vivo or in situ; (3) regulation of the phosphorylation state of receptors, e.g., insulin receptor, e.g., insulin receptor substrate 1, either in vitro, in vivo or in situ.

Various aspects of the invention are described in further detail in the following subsections:

I. Isolated Nucleic Acid Molecules

One aspect of the invention pertains to isolated nucleic acid molecules that encode CSAPTP proteins or biologically active portions thereof, as well as nucleic acid fragments sufficient for use as hybridization probes to identify CSAPTP-encoding nucleic acids (e.g., CSAPTP mRNA) and fragments for use as PCR primers for the amplification or mutation of CSAPTP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CSAPTP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, or SEQ ID NO:7, or a portion thereof, can be isolated using standard molecular biology techniques and the sequence information provided herein. For Example, using all or portion of the nucleic acid sequence of SEQ ID NO:1, SEQ ID NO:3, SEQ ID NO:4, SEQ ID NO:6, SEQ ID NO:7, or SEQ ID NO:9, as a hybridization probe, CSAPTP nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, SEQ ID NO:6, SEQ ID NO:7, or SEQ ID NO:9can be isolated by the polymerase chain reaction (PCR) using synthetic oligonucleotide primers designed based upon the sequence of SEQ ID NO:1, SEQ ID NO:3, SEQ ID NO:4, SEQ ID NO:6, SEQ ID NO:7, or SEQ ID NO:9.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CSAPTP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:4, and SEQ ID NO:7. The sequence of SEQ ID NO:1, SEQ ID NO:4, and SEQ ID NO:7, corresponds to the human CSAPTP-1, CSAPTP-2 and CSAPTP-3 cDNA, respectively. These cDNAs comprise sequence encoding the human CSAPTP-1, CSAPTP-2 and CSAPTP-3 protein (i.e., "the coding region", from nucleotides 247–765, 1–789, and 1–627 respectively), 5' untranslated (from nucleotides 1–246) and 3' untranslated sequences (nucleotides 766–1315, 788–1016, and 628–817 respectively). Alternatively, the nucleic acid molecule can comprise only the coding region of SEQ ID NO:1, SEQ ID NO:4, and SEQ ID NO:7 (e.g., nucleotides 247–765, 1–789, and 1–627 respectively, corresponding to SEQ ID NO:3, SEQ ID NO:6, and SEQ ID NO:9, respectively).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, SEQ ID NO:7, or SEQ ID NO:9 or a portion of any of these nucleotide sequences. A nucleic acid molecule which is complementary to the nucleotide sequence shown in SEQ ID NO:1, SEQ ID NO:3, SEQ ID NO:4, SEQ ID NO:6, SEQ ID NO:7, or SEQ ID NO:9 is one which is sufficiently complementary to the nucleotide sequence shown in SEQ ID NO:1, SEQ ID NO:3, SEQ ID NO:4, SEQ ID NO:6, SEQ ID NO:7, or SEQ ID NO:9, respectively, such that it can hybridize to the nucleotide sequence shown in SEQ ID NO:1, SEQ ID NO:3, SEQ ID NO:4, SEQ ID NO:6, SEQ ID NO:7, or SEQ ID NO:9, respectively, thereby forming a stable duplex.

In still another preferred embodiment, an isolated nucleic acid molecule of the present invention comprises a nucleotide sequence which is at least 30, 31, 32–35%, preferably about 35–36%, 36–40%, more preferably at least 40–43%, 43–45%, more preferably at least 45–50%, and even more preferably at least 50–55%, 55–57%, 57–60%, 60–65%, 65–70%, 70–75%, 75–80%, 80–85%, 85–90%, or 90–95% or more homologous to the nucleotide sequences shown in SEQ ID NO:1, SEQ ID NO:3, SEQ ID NO:4, SEQ ID NO:6, SEQ ID NO:7, or SEQ ID NO:9 or a portion of any of these nucleotide sequences.

Moreover, the nucleic acid molecule of the invention can comprise only a portion of the nucleic acid sequence (e.g., to the entire length of the nucleotide sequence) of SEQ ID NO:1, SEQ ID NO:3, SEQ ID NO:4, SEQ ID NO:6, SEQ ID NO:7, or SEQ ID NO:9, for example a fragment which can be used as a probe or primer or a fragment encoding a biologically active portion of a CSAPTP protein. The nucleotide sequence determined from the cloning of the CSAPTP gene allows for the generation of probes and primers designed for use in identifying and/or cloning other CSAPTP family members, as well as CSAPTP homologues from other species. The probe/primer typically comprises substantially purified oligonucleotide. The oligonucleotide typically comprises a region of nucleotide sequence that hybridizes under stringent conditions to at least 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, SEQ ID NO:4, SEQ ID NO:6, SEQ ID NO:7, or SEQ ID NO:9 of an anti-sense sequence of SEQ ID NO:1, SEQ ID NO:3, SEQ ID NO:4, SEQ ID NO:6, SEQ ID NO:7, or SEQ ID NO:9 or of a naturally occurring mutant of SEQ ID NO:1, SEQ ID NO:3, SEQ ID NO:4, SEQ ID NO:6, SEQ ID NO:7, or SEQ ID NO:9.

In an exemplary embodiment, a nucleic acid molecule of the present invention comprises a nucleotide sequence which is about 100, preferably 100–200, preferably 200–300, more preferably 300–400, more preferably 400–500, and even more preferably 500–516 nucleotides in length and hybridizes under stringent hybridization conditions to a nucleic acid molecule of SEQ ID NO:1 or SEQ ID NO:3.

In an exemplary embodiment, a nucleic acid molecule of the present invention comprises a nucleotide sequence which is about 450, preferably 450–550, more preferably 550–650, more preferably 650–750, and even more preferably 750–789 nucleotides in length and hybridizes under stringent hybridization conditions to a nucleic acid molecule of SEQ ID NO:4 or SEQ ID NO:6.

In an exemplary embodiment, a nucleic acid molecule of the present invention comprises a nucleotide sequence which is about 300, preferably 300–400, more preferably 400–500, more preferably 500–600, and even more preferably 600–627 nucleotides in length and hybridizes under stringent hybridization conditions to a nucleic acid molecule of SEQ ID NO:7, or SEQ ID NO:9.

Probes based on the CSAPTP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a CSAPTP protein, such as by measuring a level of a CSAPTP-encoding nucleic acid in a sample of cells from a subject e.g., detecting CSAPTP mRNA levels or determining whether a genomic CSAPTP gene has been mutated or deleted.

A nucleic acid fragment encoding a "biologically active portion of a CSAPTP protein" can be prepared by isolating a portion of the nucleotide sequence of SEQ ID NO:1, SEQ ID NO:3, SEQ ID NO:4, SEQ ID NO:6, SEQ ID NO:7, or SEQ ID NO:9, which encodes a polypeptide having a CSAPTP biological activity (the biological activities of the CSAPTP proteins have previously been described), expressing the encoded portion of the CSAPTP protein (e.g., by recombinant expression in vitro) and assessing the activity of the encoded portion of the CSAPTP protein.

The invention further encompasses nucleic acid molecules that differ from the nucleotide sequence shown in SEQ ID NO:1, SEQ ID NO:3, SEQ ID NO:4, SEQ ID NO:6, SEQ ID NO:7, or SEQ ID NO:9, due to degeneracy of the genetic code and thus encode the same CSAPTP proteins as those encoded by the nucleotide sequence shown in SEQ ID NO:1, SEQ ID NO:3, SEQ ID NO:4, SEQ ID NO:6, SEQ ID NO:7, SEQ ID NO:9. In another embodiment, an isolated nucleic acid molecule of the invention has a nucleotide sequence encoding a protein having an amino acid sequence shown in SEQ ID NO:2, SEQ ID NO:5, or SEQ ID NO:8.

In addition to the CSAPTP nucleotide sequences shown in SEQ ID NO:1, SEQ ID NO:3, SEQ ID NO:4, SEQ ID NO:6, SEQ ID NO:7, or SEQ ID NO:9, it will be appreciated by those skilled in the art that DNA sequence polymorphisms that lead to changes in the amino acid sequences of the CSAPTP proteins may exist within a population (e.g., the human population). Such genetic polymorphism in the CSAPTP genes may exist among individuals within a population due to natural allelic variation. As used herein, the terms "gene" and "recombinant gene" refer to nucleic acid molecules comprising an open reading frame encoding a CSAPTP protein, preferably a mammalian CSAPTP protein. Such natural allelic variations can typically result in 1–5% variance in the nucleotide sequence of a CSAPTP gene. Any and all such nucleotide variations and resulting amino acid polymorphisms in CSAPTP genes that are the result of natural allelic variation and that do not alter the functional activity of a CSAPTP protein are intended to be within the scope of the invention.

Moreover, nucleic acid molecules encoding other CSAPTP family members, and thus which have a nucleotide sequence which differs from the CSAPTP sequences of SEQ ID NO:1, SEQ ID NO:3, SEQ ID NO:4, SEQ ID NO:6, SEQ ID NO:7, or SEQ ID NO:9 are intended to be within the scope of the invention. For example, a CSAPTP cDNA can be identified based on the nucleotide sequence of human CSAPTP. Moreover, nucleic acid molecules encoding CSAPTP proteins from different species, and thus which have a nucleotide sequence which differs from the CSAPTP sequences of SEQ ID NO:1, SEQ ID NO:3, SEQ ID NO:4, SEQ ID NO:6, SEQ ID NO:7, or SEQ ID NO:9 are intended to be within the scope of the invention. For example, an mouse CSAPTP cDNA can be identified based on the nucleotide sequence of a human CSAPTP.

Nucleic acid molecules corresponding to natural allelic variants and homologues of the CSAPTP cDNAs of the invention can be isolated based on their homology to the CSAPTP nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:3, SEQ ID NO:4, SEQ ID NO:6, SEQ ID NO:7, or SEQ ID NO:. In other embodiment, the nucleic acid is at least 30, 50, 100, 250, 500, 750, 1000, 1500 nucleotides in length. As used herein, the term "hybridizes under stringent conditions" is intended to describe conditions for hybridization and washing under which nucleotide sequences at least 25%, 30%, 35%, 40%, 45%, 50%, 55%, 60%, 65%, 70%, 75%, 80%, 85%, 90%, 95% or more homologous to each other typically remain hybridized to each other. Preferably, the conditions are such that sequences at least 70%, more preferably at least 80%, even more preferably at least 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, SEQ ID NO:4, SEQ ID NO:6, SEQ ID NO:7, SEQ ID NO:9 corresponds to a naturally-occurring nucleic acid molecule. As used herein, a "naturally-occurring" nucleic acid molecule includes an RNA or DNA molecule having a nucleotide sequence that occurs in nature (e.g., encodes a natural protein).

In addition to naturally-occurring allelic variants of the CSAPTP sequences that may exist in the population, the skilled artisan will further appreciate that changes can be introduced by mutation into the nucleotide sequences of SEQ ID NO:1, SEQ ID NO:3, SEQ ID NO:4, SEQ ID NO:6, SEQ ID NO:7, or SEQ ID NO:9, thereby leading to changes in the amino acid sequence of the encoded CSAPTP proteins, without altering the functional ability of the CSAPTP proteins. For example, nucleotide substitutions leading to amino acid substitutions at "non-essential" amino acid residues can be made in the sequence of SEQ ID NO:1, SEQ ID NO:3, SEQ ID NO:4, SEQ ID NO:6, SEQ ID NO:7, or SEQ ID NO:9. A "non-essential" amino acid residue is a residue that can be altered from the wild-type sequence of CSAPTP (e.g., the sequence of SEQ ID NO:2, SEQ ID NO:5, or SEQ ID NO:8) without altering the biological activity, whereas an "essential" amino acid residue is required for biological activity. For example, amino acid residues that are conserved among the CSAPTP proteins of the present invention, are predicted to be particularly unamenable to alteration (e.g., the ten conserved cysteines involved in forming disulfide linkages or the conserved histidine, aspartate, or serine of the active enzymatic site). Moreover, amino acid residues that are defined by the CSAPTP unique N-terminal domain, intradomain disulfide bond consensus sequence, phosphatase active domain, phosphatase extended catalytic active domain (VXVHCXAGXSRSXTX (3) AYLM), phosphatase catalytic active domain ([I/V] HCXAGXXR [S/T], phosphatase catalytic core active domain ((H/V)C(X)$_5$R(S/T), and the phosphatase catalytic invariant core active domain, are particularly unamenable to alteration. Furthermore, additional amino acid residues that are conserved between the CSAPTP proteins of the present invention and other members of the Protein Tyrosine Phosphatase superfamily or protein families containing tyrosine, serine or threonine phosphatase activity are not likely to be amenable to alteration.

Accordingly, another aspect of the invention pertains to nucleic acid molecules encoding CSAPTP proteins that contain changes in amino acid residues that are not essential for activity. Such CSAPTP proteins differ in amino acid sequence from SEQ ID NO:2, SEQ ID NO:5, or SEQ ID NO:8 yet retain biological activity. In one embodiment, the isolated nucleic acid molecule comprises a nucleotide sequence encoding a protein, wherein the protein comprises an amino acid sequence at least 10%, 15%, 20%, 23%, 24%, 25%, 30%, 35%, 40%, 45%, 50%, 55%, 57%, 60%, 65%, 70%, 75%, 80%, 85%, 95%, 99% or more homologous to the amino acid sequence of SEQ ID NO:2, SEQ ID NO:5, or SEQ ID NO:8. Preferably, the protein encoded by the nucleic acid molecule is at least 65–70% homologous to SEQ ID NO:2, SEQ ID NO:5, or SEQ ID NO:8, more preferably at least 75–80% homologous to SEQ ID NO:2, SEQ ID NO:5, or SEQ ID NO:8, even more preferably at least 85–90% homologous to SEQ ID NO:2, SEQ ID NO:5, or SEQ ID NO:8, and most preferably at least 95% homologous to SEQ ID NO:2, SEQ ID NO:5, or SEQ ID NO:8 (e.g., the entire amino acid sequence of SEQ ID NO:2, SEQ ID NO:5, or SEQ ID NO:8).

An isolated nucleic acid molecule encoding a CSAPTP protein homologous to the protein of SEQ ID NO:2, SEQ ID NO:5, or SEQ ID NO:8 can be created by introducing one or more nucleotide substitutions, additions or deletions into the nucleotide sequence of SEQ ID NO:1, SEQ ID NO:3, SEQ ID NO:4, SEQ ID NO:6, SEQ ID NO:7, or SEQ ID NO:9, such that one or more amino acid substitutions, additions or deletions are introduced into the encoded protein. Mutations can be introduced into SEQ ID NO:1, SEQ ID NO:3, SEQ ID NO:4, SEQ ID NO:6, SEQ ID NO:7, or SEQ ID NO:9 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a CSAPTP protein is preferably replaced with another amino acid residue from the same side chain family. Alternatively, in another embodiment, mutations can be introduced randomly along all or part of a CSAPTP coding sequence, such as by saturation mutagenesis, and the resultant mutants can be screened for CSAPTP biological activity to identify mutants that retain activity. Following mutagenesis of SEQ ID NO:1, SEQ ID NO:3, SEQ ID NO:4, SEQ ID NO:6, SEQ ID NO:7, or SEQ ID NO:9, the encoded protein can be expressed recombinantly and the activity of the protein can be determined.

In a preferred embodiment, a mutant CSAPTP protein can be assayed for the ability to (1) regulate the cell cycle, e.g., dephosphorylation of phosphorylated proteins involved in the cell cycle, e.g., dephosphorylation of phosphorylated proteins involved in the cell cycle, e.g., proliferation-mediating proteins, e.g., Cdc25A, a cell cycle phosphatase which regulates the G1/S-phase transition, e.g., anti-proliferative proteins, either in vitro, in vivo or in situ; (2) mediation of the viral pathogenicity, e.g., viral phosphatase mediated dephosphorlation of host phosphorylated proteins, for example, viral induced disease, e.g., Yersinia pathogenesis, for example, *Yersinia pestis* (Bubonic Plague), e.g., viral phosphatase mediated dephosphorlation of host anti-proliferative phosphorylated proteins, for example, viral induced proliferative diseases, e.g., viral induced cancers, either in vitro, in vivo or in situ; (3) regulation of the phosphorylation state of receptors, e.g., insulin receptor, e.g., insulin receptor substrate 1, either in vitro, in vivo or in situ.

In addition to the nucleic acid molecules encoding CSAPTP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CSAPTP coding strand, or to only a portion thereof. In one embodiment, an antisense nucleic acid molecule is antisense to a "coding region" of the coding strand of a nucleotide sequence encoding CSAPTP. The term "coding region" includes the region of the nucleotide sequence comprising codons which are translated into amino acid residues (e.g., the coding region of human CSAPTP corresponds to ). In another embodiment, the antisense nucleic acid molecule is antisense to a "noncoding region" of the coding strand of a nucleotide sequence encoding CSAPTP. The term "noncoding region" includes 5' and 3' sequences which flank the coding region that are not translated into amino acids (i.e., also referred to as 5' and 3' untranslated regions).

Given the coding strand sequences encoding CSAPTP disclosed herein (e.g., SEQ ID NO:3, SEQ ID NO:6, SEQ ID NO:9), antisense nucleic acids of the invention can be designed according to the rules of Watson and Crick base pairing. The antisense nucleic acid molecule can be complementary to the entire coding region of CSAPTP mRNA, but more preferably is an oligonucleotide which is antisense to only a portion of the coding or noncoding region of CSAPTP mRNA. For example, the antisense oligonucleotide can be complementary to the region surrounding the translation start site of CSAPTP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CSAPTP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS* Lett. 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave CSAPTP mRNA transcripts to thereby inhibit translation of CSAPTP mRNA. A ribozyme having specificity for a CSAPTP-encoding nucleic acid can be designed based upon the nucleotide sequence of a CSAPTP cDNA disclosed herein (i.e., SEQ ID NO:1, SEQ ID NO:3, SEQ ID NO:4, SEQ ID NO:6, SEQ ID NO:7, or SEQ ID NO:9. For example, a derivative of a *Tetrahymena* L-19 IVS RNA can be constructed in which the nucleotide sequence of the active site is complementary to the nucleotide sequence to be cleaved in a CSAPTP-encoding mRNA. See, e.g., Cech et al. U.S. Pat. No. 4,987,071; and Cech et al. U.S. Pat. No. 5,116,742. Alternatively, CSAPTP mRNA can be used to select a catalytic RNA having a specific ribonuclease activity from a pool of RNA molecules. See, e.g., Bartel, D. and Szostak, J. W. (1993) *Science* 261:1411–1418.

Alternatively, CSAPTP gene expression can be inhibited by targeting nucleotide sequences complementary to the regulatory region of the CSAPTP (e.g., the CSAPTP promoter and/or enhancers) to form triple helical structures that prevent transcription of the CSAPTP gene in target cells. See generally, Helene, C. (1991) *Anticancer Drug Des.* 6(6) :569–84; Helene, C. et al. (1992) *Ann. N. Y Acad. Sci.* 660:27–36; and Maher, L. J. (1992) *Bioassays* 14(12) :807–15.

In yet another embodiment, the CSAPTP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93: 14670–675.

PNAs of CSAPTP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of CSAPTP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of CSAPTP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of CSAPTP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad Sci. US.* 86:6553–6556; Lemaitre et al. (1987) *Proc. Natl. Acad. Sci. USA* 84:648–652; PCT Publication No. W088/09810, published Dec. 15, 1988) or the blood-brain barrier (see, e.g., PCT Publication No. W089/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated CSAPTP Proteins and Anti-CSAPTP Antibodies

One aspect of the invention pertains to isolated CSAPTP proteins, and biologically active portions thereof, as well as polypeptide fragments suitable for use as immunogens to raise anti-CSAPTP antibodies. In one embodiment, native CSAPTP proteins can be isolated from cells or tissue sources by an appropriate purification scheme using standard protein purification techniques. In another embodiment, CSAPTP proteins are produced by recombinant DNA techniques. Alternative to recombinant expression, a CSAPTP protein or polypeptide can be synthesized chemically using standard peptide synthesis techniques.

An "isolated" or "purified" protein or biologically active portion thereof is substantially free of cellular material or other contaminating proteins from the cell or tissue source from which the CSAPTP protein is derived, or substantially free from chemical precursors or other chemicals when chemically synthesized. The language "substantially free of cellular material" includes preparations of CSAPTP protein in which the protein is separated from cellular components of the cells from which it is isolated or recombinantly produced. In one embodiment, the language "substantially free of cellular material" includes preparations of CSAPTP protein having less than about 30% (by dry weight) of non-CSAPTP protein (also referred to herein as a "contaminating protein"), more preferably less than about 20% of non-CSAPTP protein, still more preferably less than about 10% of non-CSAPTP protein, and most preferably less than about 5% non-CSAPTP protein. When the CSAPTP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CSAPTP protein in which the protein is separated from chemical precursors or other chemicals which are involved in the synthesis of the protein. In one embodiment, the language "substantially free of chemical precursors or other chemicals" includes preparations of CSAPTP protein having less than about 30% (by dry weight) of chemical precursors or non-CSAPTP chemicals, more preferably less than about 20% chemical precursors or non-CSAPTP chemicals, still more preferably less than about 10% chemical precursors or non-CSAPTP chemicals, and most preferably less than about 5% chemical precursors or non-CSAPTP chemicals.

Biologically active portions of a CSAPTP protein include peptides comprising amino acid sequences sufficiently homologous to or derived from the amino acid sequence of the CSAPTP protein, e.g., the amino acid sequence shown in SEQ ID NO:2, SEQ ID NO:5, or SEQ ID NO:8, which include less amino acids than the full length CSAPTP proteins, and exhibit at least one activity of a CSAPTP protein. Typically, biologically active portions comprise a domain or motif with at least one activity of the CSAPTP protein. A biologically active portion of a CSAPTP protein can be a polypeptide which is, for example, 10, 25, 50, 100 or more amino acids in length.

It is to be understood that a preferred biologically active portion of a CSAPTP protein of the present invention may contain at least one of the above-identified structural domains. A more preferred biologically active portion of a CSAPTP protein may contain at least two of the above-identified structural domains. Moreover, other biologically active portions, in which other regions of the protein are deleted, can be prepared by recombinant techniques and evaluated for one or more of the functional activities of a native CSAPTP protein.

In a preferred embodiment, the CSAPTP protein has an amino acid sequence shown in SEQ ID NO:2, SEQ ID NO:5, or SEQ ID NO:8. In other embodiments, the CSAPTP protein is substantially homologous to SEQ ID NO:2, SEQ ID NO:5, or SEQ ID NO:8, and retains the functional activity of the protein of SEQ ID NO:2, SEQ ID NO:5, or SEQ ID NO:8, yet differs in amino acid sequence due to natural allelic variation or mutagenesis, as described in detail in subsection I above.

Accordingly, in another embodiment, the CSAPTP-1 protein is a protein which comprises an amino acid sequence at least 79% homologous to the amino acid sequence of SEQ ID NO:2, and retains the functional activity of the CSAPTP-1 proteins of SEQ ID NO:2. Preferably, the protein is at least 30–35% homologous to SEQ ID NO:2, more preferably at least 35–40% homologous to SEQ ID NO:2, even more preferably at least 40–45% homologous to SEQ ID NO:2, and even more preferably at least 45–50%, 50–55%, 55–60%, 60–65%, 65–70%, 70–75%, 75–79%, 79–80%, 80–85%, 85–90%, or 90–95% or more homologous to SEQ ID NO:2.

Accordingly, in another embodiment, the CSAPTP-2 protein is a protein which comprises an amino acid sequence at least 23% homologous to the amino acid sequence of SEQ ID NO:5 and retains the functional activity of the CSAPTP-2 proteins of SEQ ID NO:5. Preferably, the protein is at least 10%%–15% homologous to SEQ ID NO:5, more preferably at least 15–20%, more preferably at least 20–23%, more preferably at least 23–25%,more preferably at least 25–30%, more preferably at least 30–35%, more preferably at least 35–40% homologous to SEQ ID NO:5, even more preferably at least 40–45% homologous to SEQ ID NO:5, and even more preferably at least 45–50%, 50–55%, 55–60%, 60–65%, 65–70%, 70–75%, 75–80%, 80–85%, 85–90%, or 90–95% or more homologous to SEQ ID NO:5.

Accordingly, in another embodiment, the CSAPTP-3 protein is a protein which comprises an amino acid sequence at least 24% homologous to the amino acid sequence of SEQ ID NO:8 and retains the functional activity of the CSAPTP-3 proteins of SEQ ID NO:8. Preferably, the protein is at least 10–15%, 15–20%, 20–24%, 24–25%, 25–30–35% homologous to SEQ ID NO:8, more preferably at least 35–40% homologous to SEQ ID NO:8, even more preferably at least 40–45% homologous to SEQ ID NO:8, and even more preferably at least 45–50%, 50–55%, 55–60%, 60–65%, 65–70%, 70–75%, 75–80%, 80–85%, 85–90%, or 90–95% or more homologous to SEQ ID NO:8.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the CSAPTP amino acid sequence of SEQ ID NO:2 having 263 amino acid residues, at least 80, preferably at least 100, more preferably at least 150, even more preferably at least 200, and even more preferably at least 225, 250 or 270 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to CSAPTP nucleic acid molecules of the invention. BLAST protein searches can be performed with the XBLAST program, score=50, wordlength=3 to obtain amino acid sequences homologous to CSAPTP protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides CSAPTP chimeric or fusion proteins. As used herein, a CSAPTP "chimeric protein" or "fusion protein" comprises a CSAPTP polypeptide operatively linked to a non-CSAPTP polypeptide. A "CSAPTP polypeptide" includes a polypeptide having an amino acid sequence corresponding to CSAPTP, whereas a "non-CSAPTP polypeptide" includes a polypeptide having an amino acid sequence corresponding to a protein which is not substantially homologous to the CSAPTP protein, e.g., a protein which is different from the CSAPTP protein and which is derived from the same or a different organism. Within a CSAPTP fusion protein the CSAPTP polypeptide can correspond to all or a portion of a CSAPTP protein. In a preferred embodiment, a CSAPTP fusion protein comprises at least one biologically active portion of a CSAPTP protein. In another preferred embodiment, a CSAPTP fusion protein comprises at least two biologically active portions of a CSAPTP protein. Within the fusion protein, the term "operatively linked" is intended to indicate that the CSAPTP polypeptide and the non-CSAPTP polypeptide are fused in-frame to each other. The non-CSAPTP polypeptide can be fused to the N-terminus or C-terminus of the CSAPTP polypeptide.

For example, in one embodiment, the fusion protein is a GST-CSAPTP fusion protein in which the CSAPTP sequences are fused to the C-terminus of the GST sequences. Such fusion proteins can facilitate the purification of recombinant CSAPTP.

In another embodiment, the fusion protein is a CSAPTP protein containing a heterologous signal sequence at its N-terminus. For example, the native CSAPTP signal sequence can be removed and replaced with a signal sequence from another protein. In certain host cells (e.g., mammalian host cells), expression and/or secretion of CSAPTP can be increased through use of a heterologous signal sequence.

The CSAPTP fusion proteins of the invention can be incorporated into pharmaceutical compositions and administered to a subject in vivo. The CSAPTP fusion proteins can be used to affect the bioavailability of a CSAPTP target molecule. Use of CSAPTP fusion proteins may be useful therapeutically for the treatment of proliferative disorders (e.g., cancer). Moreover, the CSAPTP-fusion proteins of the invention can be used as immunogens to produce anti-CSAPTP antibodies in a subject, to purify CSAPTP ligands and in screening assays to identify molecules which inhibit the interaction of CSAPTP with a CSAPTP target molecule.

Preferably, a CSAPTP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A CSAPTP-encoding nucleic acid can be cloned into such an expression vector such that the fusion moiety is linked in-frame to the CSAPTP protein.

The present invention also pertains to variants of the CSAPTP proteins which function as either CSAPTP agonists (mimetics) or as CSAPTP antagonists. Variants of the CSAPTP proteins can be generated by mutagenesis, e.g., discrete point mutation or truncation of a CSAPTP protein. An agonist of the CSAPTP proteins can retain substantially the same, or a subset, of the biological activities of the naturally occurring form of a CSAPTP protein. An antagonist of a CSAPTP protein can inhibit one or more of the activities of the naturally occurring form of the CSAPTP protein by, for example, competitively inhibiting the phosphatase activity of a CSAPTP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the CSAPTP protein.

In one embodiment, variants of a CSAPTP protein which function as either CSAPTP agonists (mimetics) or as CSAPTP antagonists can be identified by screening combinatorial libraries of mutants, e.g., truncation mutants, of a CSAPTP protein for CSAPTP protein agonist or antagonist activity. In one embodiment, a variegated library of CSAPTP variants is generated by combinatorial mutagenesis at the nucleic acid level and is encoded by a variegated gene library. A variegated library of CSAPTP variants can be produced by, for example, enzymatically ligating a mixture of synthetic oligonucleotides into gene sequences such that a degenerate set of potential CSAPTP sequences is expressible as individual polypeptides, or alternatively, as a set of larger fusion proteins (e.g., for phage display) containing the set of CSAPTP sequences therein. There are a variety of methods which can be used to produce libraries of potential CSAPTP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CSAPTP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CSAPTP protein coding sequence can be used to generate a variegated population of CSAPTP fragments for screening and subsequent selection of variants of a CSAPTP protein. In one embodiment, a library of coding sequence fragments can be generated by treating a double stranded PCR fragment of a CSAPTP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, and internal fragments of various sizes of the CSAPTP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CSAPTP proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify CSAPTP variants (Arkin and Yourvan (1992) PNAS 89:7811–7815; Delgrave et al. (1993) *Protein Engineering* 6(3):327–331).

In one embodiment, cell based assays can be exploited to analyze a variegated CSAPTP library. For example, a library of expression vectors can be transfected into a cell line which ordinarily synthesizes and secretes CSAPTP. The transfected cells are then cultured such that CSAPTP and a particular mutant CSAPTP are secreted and the effect of expression of the mutant on CSAPTP activity in cell supernatants can be detected, e.g., by any of a number of enzymatic assays. Plasmid DNA can then be recovered from the cells which score for inhibition, or alternatively, potentiation of CSAPTP activity, and the individual clones further characterized.

An isolated CSAPTP protein, or a portion or fragment thereof, can be used as an immunogen to generate antibodies that bind CSAPTP using standard techniques for polyclonal and monoclonal antibody preparation. A full-length CSAPTP protein can be used or, alternatively, the invention provides antigenic peptide fragments of CSAPTP for use as immunogens. The antigenic peptide of a CSAPTP protein comprises at least 8 amino acid residues of the amino acid sequence shown in SEQ ID NO:2, SEQ ID NO:5, SEQ ID NO:8, or SEQ ID NO:8 and encompasses an epitope of CSAPTP such that an antibody raised against the peptide forms a specific immune complex with CSAPTP. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of CSAPTP that are located on the surface of the protein, e.g., hydrophilic regions.

A CSAPTP immunogen typically is used to prepare antibodies by immunizing a suitable subject, (e.g., rabbit, goat, mouse or other mammal) with the immunogen. An appropriate immunogenic preparation can contain, for example, recombinantly expressed CSAPTP protein or a chemically synthesized CSAPTP polypeptide. The preparation can further include an adjuvant, such as Freund's complete or incomplete adjuvant, or similar immunostimulatory agent. Immunization of a suitable subject with an immunogenic CSAPTP preparation induces a polyclonal anti-CSAPTP antibody response.

Accordingly, another aspect of the invention pertains to anti-CSAPTP antibodies. The term "antibody" as used herein includes immunoglobulin molecules and immunologically active portions of immunoglobulin molecules, i.e., molecules that contain an antigen binding site which specifically binds (immunoreacts with) an antigen, such as CSAPTP. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind CSAPTP. The term "monoclonal antibody" or "monoclonal antibody composition", as used herein, includes a population of antibody molecules that contain only one species of an antigen binding site capable of immunoreacting with a particular epitope of CSAPTP. A monoclonal antibody composition thus typically displays a single binding affinity for a particular CSAPTP protein with which it immunoreacts.

Polyclonal anti-CSAPTP antibodies can be prepared as described above by immunizing a suitable subject with a CSAPTP immunogen. The anti-CSAPTP antibody titer in the immunized subject can be monitored over time by standard techniques, such as with an enzyme linked immunosorbent assay (ELISA) using immobilized CSAPTP. If desired, the antibody molecules directed against CSAPTP can be isolated from the mammal (e.g., from the blood) and further purified by well known techniques, such as protein A chromatography to obtain the IgG fraction. At an appropriate time after immunization, e.g., when the anti-CSAPTP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1 976) *PNAS* 76:2927–3 1; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lemer (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a CSAPTP immunogen as described above, and the culture supernatants of the resulting hybridoma cells are screened to identify a hybridoma producing a monoclonal antibody that binds CSAPTP.

Any of the many well known protocols used for fusing lymphocytes and immortalized cell lines can be applied for the purpose of generating an anti-CSAPTP monoclonal antibody (see, e.g., G. Galfre et al. (1977) *Nature* 266:55052; Gefter et al. *Somatic Cell Genet.*, cited supra; Lerner, *Yale J. Biol. Med*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—

Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CSAPTP, e.g., using a standard ELISA assay.

Alternative to preparing monoclonal antibody-secreting hybridomas, a monoclonal anti-CSAPTP antibody can be identified and isolated by screening a recombinant combinatorial immunoglobulin library (e.g., an antibody phage display library) with CSAPTP to thereby isolate immunoglobulin library members that bind CSAPTP. Kits for generating and screening phage display libraries are commercially available (e.g., the Pharmacia *Recombinant Phage Antibody System*, Catalog No. 27-9400–01; and the Stratagene *SurfJZP™ Phage Display Kit*, Catalog No. 240612). Additionally, examples of methods and reagents particularly amenable for use in generating and screening antibody display library can be found in, for example, Ladner et al. U.S. Pat No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624– 628; Gram et al. (1992) *PNAS* 89:3576–3580; Garrad et al. (1991) Bio/Technology 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-CSAPTP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-CSAPTP antibody (e.g., monoclonal antibody) can be used to isolate CSAPTP by standard techniques, such as affinity chromatography or immunoprecipitation. An anti-CSAPTP antibody can facilitate the purification of natural CSAPTP from cells and of recombinantly produced CSAPTP expressed in host cells. Moreover, an anti-CSAPTP antibody can be used to detect CSAPTP protein (e.g., in a cellular lysate or cell supernatant) in order to evaluate the abundance and pattern of expression of the CSAPTP protein. Anti-CSAPTP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase$\beta$, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a CSAPTP protein (or a portion thereof). As used herein, the term "vector" includes a nucleic acid molecule capable of transporting another nucleic acid to which it has been linked. One type of vector is a "plasmid", which includes a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CSAPTP proteins, mutant forms of CSAPTP proteins, fusion proteins, etc.).

The recombinant expression vectors of the invention can be designed for expression of CSAPTP proteins in prokaryotic or eukaryotic cells. For example, CSAPTP proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in CSAPTP activity assays, (e.g., direct assays or competitive assays described in detail below), or to generate antibodies specific for CSAPTP proteins, for example. In a preferred embodiment, a CSAPTP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the CSAPTP expression vector is a yeast expression vector. Examples of vectors for expression in yeast *S. cerivisae* include pYepSec 1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, CSAPTP proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) Cell 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CSAPTP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CSAPTP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a CSAPTP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CSAPTP protein. Accordingly, the invention further provides methods for producing a CSAPTP protein using the host cells of the invention. In one embodiment, the method comprises culturing the host cell of invention (into which a recombinant expression vector encoding a CSAPTP protein has been introduced) in a suitable medium such that a CSAPTP protein is produced. In another embodiment, the method further comprises isolating a CSAPTP protein from the medium or the host cell.

The host cells of the invention can also be used to produce nonhuman transgenic animals. For example, in one embodiment, a host cell of the invention is a fertilized oocyte or an embryonic stem cell into which CSAPTP-coding sequences have been introduced. Such host cells can then be used to create non-human transgenic animals in which exogenous CSAPTP sequences have been introduced into their genome or homologous recombinant animals in which endogenous CSAPTP sequences have been altered. Such animals are useful for studying the function and/or activity of a CSAPTP and for identifying and/or evaluating modulators of CSAPTP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CSAPTP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a CSAPTP-encoding nucleic acid into the male pronuclei of a fertilized oocyte, e.g., by microinjection, retroviral infection, and allowing the oocyte to develop in a pseudopregnant female foster animal. The CSAPTP cDNA sequence of SEQ ID NO:1, SEQ ID NO:3, SEQ ID NO:4, SEQ ID NO:6, SEQ ID NO:7, SEQ ID NO:9 can be introduced as a transgene into the genome of a non-human animal. Alternatively, a nonhuman homologue of a human CSAPTP gene, such as a mouse or rat CSAPTP gene, can be used as a transgene. Alternatively, a CSAPTP gene homologue, such as a CSAPTP-2 gene can be isolated based on hybridization to the CSAPTP cDNA sequences of SEQ ID NO:1, SEQ ID NO:3, SEQ ID NO:4, SEQ ID NO:6, SEQ ID NO:7, or SEQ ID NO:9 (described further in subsection I above) and used as a transgene. Intronic sequences and polyadenylation signals can also be included in the transgene to increase the efficiency of expression of the transgene. A tissue-specific regulatory sequence(s) can be operably linked to a CSAPTP transgene to direct expression of a CSAPTP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a CSAPTP transgene in its genome and/or expression of CSAPTP mRNA in tissues or cells of the animals. A transgenic founder animal can then be used to breed additional animals carrying the transgene. Moreover, transgenic animals carrying a transgene encoding a CSAPTP protein can further be bred to other transgenic animals carrying other transgenes.

To create a homologous recombinant animal, a vector is prepared which contains at least a portion of a CSAPTP gene into which a deletion, addition or substitution has been introduced to thereby alter, e.g., functionally disrupt, the CSAPTP gene. The CSAPTP gene can be a human gene (e.g., the cDNA of ), but more preferably, is a non-human homologue of a human CSAPTP gene (e.g., a cDNA isolated by stringent hybridization with the nucleotide sequence of SEQ ID NO:1, SEQ ID NO:3, SEQ ID NO:4, SEQ ID NO:6, SEQ ID NO:7, SEQ ID NO:9). For example, a mouse CSAPTP gene can be used to construct a homologous recombination vector suitable for altering an endogenous CSAPTP gene in the mouse genome. In a preferred embodiment, the vector is designed such that, upon homologous recombination, the endogenous CSAPTP gene is functionally disrupted (i.e., no longer encodes a functional protein; also referred to as a "knock out" vector). Alternatively, the vector can be designed such that, upon homologous recombination, the endogenous CSAPTP gene is mutated or otherwise altered but still encodes functional protein (e.g., the upstream regulatory region can be altered to thereby alter the expression of the endogenous CSAPTP protein). In the homologous recombination vector, the altered portion of the CSAPTP gene is flanked at its 5' and 3' ends by additional nucleic acid sequence of the CSAPTP gene to allow for homologous recombination to occur between the exogenous CSAPTP gene carried by the vector and an endogenous CSAPTP gene in an embryonic stem cell. The additional flanking CSAPTP nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced CSAPTP gene has homologously recombined with the endogenous CSAPTP gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells*: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_o$ phase. Alternatively, a cell, e.g., an embryonic stem cell, from the inner cell mass of a developing embryo can be transformed with a preferred transgene. Alternatively, a cell, e.g., a somatic cell, from cell culture line can be transformed with a preferred transgene and induced to exit the growth cycle and enter $G_o$ phase. The cell can then be fused, e.g., through the use of electrical pulses, to an enucleated mammalian oocyte. The reconstructed oocyte is then cultured such that it develops to morula or blastocyte and then transferred to pseudopregnant female foster animal. The offspring borne of this female foster animal will be a clone of the animal from which the nuclear donor cell, e.g., the somatic cell, is isolated.

IV. Pharmaceutical Compositions

The CSAPTP nucleic acid molecules, CSAPTP proteins, and anti-CSAPTP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CSAPTP protein or anti-CSAPTP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

As described herein, a CSAPTP protein of the invention has one or more of the following activities: (i) interaction of a CSAPTP protein with a CSAPTP target molecule; (ii) interaction of a CSAPTP protein with a CSAPTP target molecule, wherein the CSAPTP target is a ligand, e.g., phosphorylated amino acid residue of a phosphorylated protein, e.g., a phosphatase, for example, a cell cycle regulatory phosphatase, e.g., Cdc25A phosphatase, a cell cycle phosphatase which regulates the G1/S-phase transition, a CSAPTPase, a kinase, e.g., Mitogen Activating Protein (MAP) kinase, or a Cardiovascular Associated Protein Tyrosine Kinase (CSAPTK); (iii) interaction of a CSAPTP protein with a CSAPTP target molecule, wherein the CSAPTP target is a receptor, e.g., insulin receptor, insulin receptor substrate 1; (iv) interaction of a CSAPTP protein with a CSAPTP target molecule, wherein the CSAPTP target is a viral protein, e.g., vaccinia viral transcription-mediating proteins, Myxoma viral proteins, Shope Fibroma viral proteins, *Leishmania donovani, Trypanosoma brucei* and *Trypanosoma cruzi* viral proteins.

Further, as described herein, a CSAPTP protein of the invention has one or more of the above activities and can thus be used in, for example, the: (1) regulation of cell cycle, e.g., dephosphorylation of phosphorylated proteins involved in the cell cycle, e.g., proliferation-mediating proteins, e.g., Cdc25A, a cell cycle phosphatase which regulates the G1/S-phase transition, e.g., anti-proliferative proteins, either in vitro, in vivo or in situ; (2) mediation of viral pathogenicity, e.g., viral phosphatase mediated dephosphorylation of host phosphorylated proteins, for example, viral induced disease, e.g., Yersinia pathogenesis, for example, *Yersinia pestis* (Bubonic Plague), e.g., viral phosphatase mediated dephosphorlation of host anti-proliferative phosphorylated proteins, for example, viral induced proliferative diseases, e.g., viral induced cancers, either in vitro, in vivo or in situ; (3) regulation of the phosphorylation state of receptors, e.g., insulin receptor, e.g., insulin receptor substrate 1, either in vitro, in vivo or in situ.

The isolated nucleic acid molecules of the invention can be used, for example, to express CSAPTP protein (e.g., via a recombinant expression vector in a host cell in gene therapy applications), to detect CSAPTP mRNA (e.g., in a biological sample) or a genetic alteration in a CSAPTP gene, and to modulate CSAPTP activity, as described further below. The CSAPTP proteins can be used to treat disorders characterized by insufficient or excessive production of a CSAPTP or CSAPTP target molecules. In addition, the CSAPTP proteins can be used to screen for naturally occurring CSAPTP target molecules, to screen for drugs or compounds which modulate CSAPTP activity, as well as to treat disorders characterized by insufficient or excessive production of CSAPTP protein or production of CSAPTP protein forms which have decreased or aberrant activity compared to CSAPTP wild type protein. Moreover, the anti-CSAPTP antibodies of the invention can be used to detect and isolate CSAPTP proteins, regulate the bioavailability of CSAPTP proteins, and modulate CSAPTP activity.

Accordingly one embodiment of the present invention involves a method of use (e.g., a diagnostic assay, prognostic assay, or a prophylactic/therapeutic method of treatment) wherein a molecule of the present invention (e.g., a CSAPTP protein, CSAPTP nucleic acid, or a CSAPTP modulator) is used, for example, to diagnose, prognose and/or treat a disease and/or condition in which any of the aforementioned activities (i.e., activities (i)–(iv) and (1)–(3) in the above paragraph) is indicated. In another embodiment, the present invention involves a method of use (e.g., a diagnostic assay, prognostic assay, or a prophylactic/therapeutic method of treatment) wherein a molecule of the present invention (e.g., a CSAPTP protein, CSAPTP nucleic acid, or a CSAPTP modulator) is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/therapeutic methods of treatment). involve administering to a subject, preferably a human subject, a molecule of the present invention (e.g., a CSAPTP protein, CSAPTP nucleic acid, or a CSAPTP modulator) for the diagnosis, prognosis, and/or therapeutic treatment. In another embodiment, the methods of use (e.g., diagnostic assays, prognostic assays, or prophylactic/therapeutic methods of treatment) involve administering to a human subject a molecule of the present invention (e.g., a CSAPTP protein, CSAPTP nucleic acid, or a CSAPTP modulator).

A. Screening Assay

The invention provides a method (also referred to herein as a "screening assay") for identifying modulators, i.e., candidate or test compounds or agents (e.g., peptides, peptidomimetics, small molecules or other drugs) which bind to CSAPTP proteins, have a stimulatory or inhibitory effect on, for example, CSAPTP expression or CSAPTP activity, or have a stimulatory or inhibitory effect on, for example, the activity of an CSAPTP target molecule.

In one embodiment, the invention provides assays for screening candidate or test compounds which are target molecules of a CSAPTP protein or polypeptide or biologically active portion thereof. In another embodiment, the invention provides assays for screening candidate or test compounds which bind to or modulate the activity of a CSAPTP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner USP 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a CSAPTP protein or biologically active portion thereof is contacted with a test compound and the ability of the test compound to modulate CSAPTP activity determined. Determining the ability of the test compound to modulate CSAPTP activity can be accomplished by monitoring the bioactivity of the CSAPTP protein or biologically active portion thereof. The cell, for example, can be of mammalian origin or a yeast cell. Determining the ability of the test compound to modulate CSAPTP activity can be accomplished, for example, by coupling the CSAPTP protein or biologically active portion thereof with a radioisotope or enzymatic label such that binding of the CSAPTP protein or biologically active portion thereof to its cognate target molecule can be determined by detecting the labeled CSAPTP protein or biologically active portion thereof in a complex. For example, compounds (e.g., CSAPTP protein or biologically active portion thereof) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., CSAPTP protein or biologically active portion thereof) to interact with its cognate target molecule without the labeling of any of the interactants. For example, a microphysiometer can be used to detect the interaction of a compound with its cognate target molecule without the labeling of either the compound or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which expresses a CSAPTP protein or biologically active portion thereof, with a target molecule to form an assay mixture, contacting the assay mixture with a test compound, and determining the ability of the test compound to modulate the activity of the CSAPTP protein or biologically active portion thereof, wherein determining the ability of the test compound to modulate the activity of the CSAPTP protein or biologically active portion thereof, comprises determining the ability of the test compound to modulate a biological activity of the CSAPTP expressing cell (e.g., determining the ability of the test compound to modulate cell proliferation, viral replication, and/or receptor regulation).

In another preferred embodiment, the assay comprises contacting a cell which is responsive to a CSAPTP protein or biologically active portion thereof, with a CSAPTP protein or biologically-active portion thereof, to form an assay mixture, contacting the assay mixture with a test compound, and determining the ability of the test compound to modulate the activity of the CSAPTP protein or biologically active portion thereof, wherein determining the ability of the test compound to modulate the activity of the CSAPTP protein or biologically active portion thereof comprises determining the ability of the test compound to modulate a biological activity of the CSAPTP-responsive cell (e.g., determining the ability of the test compound to modulate cell proliferation, viral replication, and/or receptor regulation).

In another embodiment, an assay is a cell-based assay comprising contacting a cell expressing a CSAPTP target molecule with a test compound and determining the ability of the test compound to modulate (e.g. stimulate or inhibit) the activity of the CSAPTP target molecule. Determining the ability of the test compound to modulate the activity of a CSAPTP target molecule can be accomplished, for example, by determining the ability of the CSAPTP protein to bind to or interact with the CSAPTP target molecule.

Determining the ability of the CSAPTP protein to bind to or interact with a CSAPTP target molecule can be accomplished by one of the methods described above for determining direct binding. In a preferred embodiment, determining the ability of the CSAPTP protein to bind to or interact with a CSAPTP target molecule can be accomplished by determining the activity of the target molecule. For example, the activity of the target molecule can be determined by detecting dephosphorylation of a phosphorylated protein. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response, for example, cell proliferation, viral replication, and/or receptor regulation In yet another embodiment, an assay of the present invention is a cell-free assay in which a CSAPTP protein or biologically active portion thereof is contacted with a test compound and the ability of the test compound to bind to the CSAPTP protein or biologically active portion thereof is determined. Binding of the test compound to the CSAPTP protein can be determined either directly or indirectly as described above. In a preferred embodiment, the assay includes contacting the CSAPTP protein or biologically active portion thereof with a known compound which binds CSAPTP (e.g., a CSAPTP target molecule) to form an assay mixture, contacting the assay mixture with a test compound, and determining the ability of the test compound to interact with a CSAPTP protein, wherein determining the ability of the test compound to interact with a CSAPTP protein comprises determining the ability of the test compound to preferentially bind to CSAPTP or biologically active portion thereof as compared to the known compound.

In another embodiment, the assay is a cell-free assay in which a CSAPTP protein or biologically active portion thereof is contacted with a test compound and the ability of the test compound to modulate (e.g., stimulate or inhibit) the activity of the CSAPTP protein or biologically active portion thereof is determined. Determining the ability of the test compound to modulate the activity of a CSAPTP protein can be accomplished, for example, by determining the ability of the CSAPTP protein to bind to a CSAPTP target molecule by one of the methods described above for determining direct binding. Determining the ability of the CSAPTP protein to bind to a CSAPTP target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a CSAPTP protein can be accomplished by determining the ability of the CSAPTP protein to further modulate the activity of a downstream effector (e.g., a transcriptionally activated immediate early response pathway component) of a CSAPTP target molecule. For example, the activity of the effector molecule on an appropriate target can be determined or the binding of the effector to an appropriate target can be determined as previously described.

In yet another embodiment, the cell-free assay involves contacting a CSAPTP protein or biologically active portion thereof with a known compound which binds the CSAPTP protein to form an assay mixture, contacting the assay mixture with a test compound, and determining the ability of the test compound to interact with the CSAPTP protein, wherein determining the ability of the test compound to interact with the CSAPTP protein comprises determining the ability of the CSAPTP protein to preferentially bind to or modulate the activity of a CSAPTP target molecule.

The cell-free assays of the present invention are amenable to use of both soluble and/or membrane-bound forms of isolated proteins (e.g. CSAPTP proteins or biologically active portions thereof or receptors to which CSAPTP targets bind). In the case of cell-free assays in which a membrane-bound form of an isolated protein is used (e.g., a cell surface receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylarnminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CSAPTP or its target molecule to facilitate separation of complexed from uncomplexed forms of one or both of the proteins, as well as to accommodate automation of the assay. Binding of a test compound to a CSAPTP protein, or interaction of a CSAPTP protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or CSAPTP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CSAPTP binding or activity determined using standard techniques.

Other techniques for immobilizing proteins on matrices can also be used in the screening assays of the invention. For example, either a CSAPTP protein or a CSAPTP target molecule can be immobilized utilizing conjugation of biotin and streptavidin. Biotinylated CSAPTP protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CSAPTP protein or target molecules but which do not interfere with binding of the CSAPTP protein to its target molecule can be derivatized to the wells of the plate, and unbound target or CSAPTP protein trapped in the wells by antibody conjugation. Methods for detecting such complexes, in addition to those described above for the GST-immobilized complexes, include immunodetection of complexes using antibodies reactive with the CSAPTP protein or target molecule, as well as enzyme-linked assays which rely on detecting an enzymatic activity associated with the CSAPTP protein or target molecule.

In another embodiment, modulators of CSAPTP expression are identified in a method wherein a cell is contacted with a candidate compound and the expression of CSAPTP mRNA or protein in the cell is determined. The level of expression of CSAPTP mRNA or protein in the presence of the candidate compound is compared to the level of expression of CSAPTP mRNA or protein in the absence of the candidate compound. The candidate compound can then be identified as a modulator of CSAPTP expression based on this comparison. For example, when expression of CSAPTP mRNA or protein is greater (statistically significantly greater) in the presence of the candidate compound than in its absence, the candidate compound is identified as a stimulator of CSAPTP mRNA or protein expression. Alternatively, when expression of CSAPTP mRNA or protein is less (statistically significantly less) in the presence of the candidate compound than in its absence, the candidate compound is identified as an inhibitor of CSAPTP mRNA or protein expression. The level of CSAPTP mRNA or protein expression in the cells can be determined by methods described herein for detecting CSAPTP mRNA or protein.

In yet another aspect of the invention, the CSAPTP proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with CSAPTP ("CSAPTP-binding proteins" or "CSAPTP-bp") and are involved in CSAPTP activity. Such CSAPTP-binding proteins are also likely to be involved in the propagation of signals by the CSAPTP proteins or CSAPTP targets as, for example, downstream elements of a CSAPTP-mediated signaling pathway. Alternatively, such CSAPTP-binding proteins are likely to be CSAPTP inhibitors.

The two-hybrid system is based on the modular nature of most transcription factors, which consist of separable DNA-binding and activation domains. Briefly, the assay utilizes two different DNA constructs. In one construct, the gene that codes for a CSAPTP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CSAPTP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the CSAPTP protein.

This invention further pertains to novel agents identified by the above-described screening assays and to processes for producing such agents by use of these assays. Accordingly, in one embodiment, the present invention includes a compound or agent obtainable by a method comprising the steps of any one of the aforementioned screening assays (e.g., cell-based assays or cell-free assays). For example, in one embodiment, the invention includes a compound or agent obtainable by a method comprising contacting a cell which expresses a CSAPTP target molecule with a test compound and the determining the ability of the test compound to bind to, or modulate the activity of, the CSAPTP target molecule.

In another embodiment, the invention includes a compound or agent obtainable by a method comprising contacting a cell which expresses a CSAPTP target molecule with a CSAPTP protein or biologically-active portion thereof, to form an assay mixture, contacting the assay mixture with a test compound, and determining the ability of the test compound to interact with, or modulate the activity of, the CSAPTP target molecule. In another embodiment, the invention includes a compound or agent obtainable by a method comprising contacting a CSAPTP protein or biologically active portion thereof with a test compound and determining the ability of the test compound to bind to, or modulate (e.g., stimulate or inhibit) the activity of, the CSAPTP protein or biologically active portion thereof. In yet another embodiment, the present invention included a compound or agent obtainable by a method comprising contacting a CSAPTP protein or biologically active portion thereof with a known compound which binds the CSAPTP protein to form an assay mixture, contacting the assay mixture with a test compound, and determining the ability of the test compound to interact with, or modulate the activity of the CSAPTP protein.

Accordingly, it is within the scope of this invention to further use an agent identified as described herein in an appropriate animal model. For example, an agent identified as described herein (e.g., a CSAPTP modulating agent, an antisense CSAPTP nucleic acid molecule, a CSAPTP-specific antibody, or a CSAPTP-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present invention also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses a CSAPTP target molecule is contacted with a test compound and the ability of the test compound to bind to, or modulate the activity of, the CSAPTP target molecule is determined. In another exemplary embodiment, the present invention includes a method of synthesizing or producing a drug or pharmaceutical composition based on the structure and/or properties of a compound obtainable by a method in which a CSAPTP protein or biologically active portion thereof is contacted with a test compound and the ability of the test compound to bind to, or modulate (e.g., stimulate or inhibit) the activity of, the CSAPTP protein or biologically active portion thereof is determined.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the CSAPTP nucleotide sequences, described herein, can be used to map the location of the CSAPTP genes on a chromosome. The mapping of the CSAPTP sequences to chromosomes is an important first step in correlating these sequences with genes associated with disease.

Briefly, CSAPTP genes can be mapped to chromosomes by preparing PCR primers (preferably 15–25 bp in length) from the CSAPTP nucleotide sequences. Computer analysis of the CSAPTP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the CSAPTP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CSAPTP nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, N.Y. 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the CSAPTP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CSAPTP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CSAPTP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CSAPTP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:3, SEQ ID NO:4, SEQ ID NO:6, SEQ ID NO:7, SEQ ID NO:9 can comfortably provide positive individual identification with a panel of perhaps 10 to 1,000 primers which each yield a noncoding amplified sequence of 100 bases. If predicted coding sequences, such as those in SEQ ID NO:1, SEQ ID NO:3, SEQ ID NO:4, SEQ ID NO:6, SEQ ID NO:7, SEQ ID NO:9 are used, a more appropriate number of primers for positive individual identification would be 500–2,000.

If a panel of reagents from CSAPTP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial CSAPTP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:3, SEQ ID NO:4, SEQ ID NO:6, SEQ ID NO:7, SEQ ID NO:9 are particularly appropriate for this use as greater numbers of polymorphisms occur in the noncoding regions, making it easier to differentiate individuals using this technique. Examples of polynucleotide reagents include the CSAPTP nucleotide sequences or portions thereof, e.g., fragments derived from the noncoding regions of SEQ ID NO:1, SEQ ID NO:3, SEQ ID NO:4, SEQ ID NO:6, SEQ ID NO:7, SEQ ID NO:9, having a length of at least 20 bases, preferably at least 30 bases.

The CSAPTP nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CSAPTP probes can be used to identify tissue by species and/or by organ type.

In a similar fashion, these reagents, e.g., CSAPTP primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining CSAPTP protein and/or nucleic acid expression as well as CSAPTP activity, in the context of a biological sample (e.g., blood, serum, cells, tissue) to thereby determine whether an individual is afflicted with a disease or disorder, or is at risk of developing a disorder, associated with aberrant CSAPTP expression or activity. The invention also provides for prognostic (or predictive) assays for determining whether an individual is at risk of developing a disorder associated with CSAPTP protein, nucleic acid expression or activity. For example, mutations in a CSAPTP gene can be assayed in a biological sample. Such assays can be used for prognostic or predictive purpose to thereby phophylactically treat an individual prior to the onset of a disorder characterized by or associated with CSAPTP protein, nucleic acid expression or activity.

Another aspect of the invention pertains to monitoring the influence of agents (e.g., drugs, compounds) on the expression or activity of CSAPTP in clinical trials.

These and other agents are described in further detail in the following sections.

1. Diagnostic Assays

An exemplary method for detecting the presence or absence of CSAPTP protein or nucleic acid in a biological sample involves obtaining a biological sample from a test subject and contacting the biological sample with a compound or an agent capable of detecting CSAPTP protein or nucleic acid (e.g., mRNA, genomic DNA) that encodes CSAPTP protein such that the presence of CSAPTP protein or nucleic acid is detected in the biological sample. A preferred agent for detecting CSAPTP mRNA or genomic DNA is a labeled nucleic acid probe capable of hybridizing to CSAPTP mRNA or genomic DNA. The nucleic acid probe can be, for example, a full-length CSAPTP nucleic acid, such as the nucleic acid of SEQ ID NO:1, SEQ ID NO:4, or SEQ ID NO:7 (or that of SEQ ID NO:3, SEQ ID NO:6, or SEQ ID NO:9, or a portion thereof), such as an oligonucleotide of at least 15, 30, 50, 100, 250 or 500 nucleotides in length and sufficient to specifically hybridize under stringent conditions to CSAPTP mRNA or genomic DNA. Other suitable probes for use in the diagnostic assays of the invention are described herein.

A preferred agent for detecting CSAPTP protein is an antibody capable of binding to CSAPTP protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CSAPTP mRNA, protein, or genomic DNA in a biological sample in vitro as well as in vivo. For example, in vitro techniques for detection of CSAPTP mRNA include Northern hybridizations and in situ hybridizations. In vitro techniques for detection of CSAPTP protein include enzyme linked immunosorbent assays (ELISAs), Western blots, immunoprecipitations and immunofluorescence. In vitro techniques for detection of CSAPTP genomic DNA include Southern hybridizations. Furthermore, in vivo techniques for detection of CSAPTP protein include introducing into a subject a labeled anti-CSAPTP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting CSAPTP protein, mRNA, or genomic DNA, such that the presence of CSAPTP protein, mRNA or genomic DNA is detected in the biological sample, and comparing the presence of CSAPTP protein, mRNA or genomic DNA in the control sample with the presence of CSAPTP protein, mRNA or genomic DNA in the test sample.

The invention also encompasses kits for detecting the presence of CSAPTP in a biological sample. For example, the kit can comprise a labeled compound or agent capable of detecting CSAPTP protein or mRNA in a biological sample; means for determining the amount of CSAPTP in the sample; and means for comparing the amount of CSAPTP in the sample with a standard. The compound or agent can be packaged in a suitable container. The kit can further comprise instructions for using the kit to detect CSAPTP protein or nucleic acid.

2. Prognostic Assays

The diagnostic methods described herein can furthermore be utilized to identify subjects having or at risk of developing a disease or disorder associated with aberrant CSAPTP expression or activity. For example, the assays described herein, such as the preceding diagnostic assays or the following assays, can be utilized to identify a subject having or at risk of developing a disorder associated with CSAPTP protein, nucleic acid expression or activity such a proliferative disorder (e.g., cancer). Alternatively, the prognostic assays can be utilized to identify a subject having or at risk for developing a metabolic disorder. Thus, the present invention provides a method for identifying a disease or disorder associated with aberrant CSAPTP expression or activity in which a test sample is obtained from a subject and CSAPTP protein or nucleic acid (e.g, mRNA, genomic DNA) is detected, wherein the presence of CSAPTP protein or nucleic acid is diagnostic for a subject having or at risk of developing a disease or disorder associated with aberrant CSAPTP expression or activity. As used herein, a "test sample" includes a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CSAPTP expression or activity. For example, such methods can be used to determine whether a subject can be effectively treated with an agent for a proliferative disorder (e.g., cancer). For example, such methods can be used to determine whether a subject can be effectively treated with an agent for a metabolic disorder. Thus, the present invention provides methods for determining whether a subject can be effectively treated with an agent for a disorder associated with aberrant CSAPTP expression or activity in which a test sample is obtained and CSAPTP protein or nucleic acid expression or activity is detected (e.g., wherein the abundance of CSAPTP protein or nucleic acid expression or activity is diagnostic for a subject that can be administered the agent to treat a disorder associated with aberrant CSAPTP expression or activity.)

The methods of the invention can also be used to detect genetic alterations in a CSAPTP gene, thereby determining if a subject with the altered gene is at risk for a disorder characterized by aberrant developmental progression. In preferred embodiments, the methods include detecting, in a sample of cells from the subject, the presence or absence of a genetic alteration characterized by at least one of an alteration affecting the integrity of a gene encoding a CSAPTP-protein, or the mis-expression of the CSAPTP gene. For example, such genetic alterations can be detected by ascertaining the existence of at least one of 1) a deletion of one or more nucleotides from a CSAPTP gene; 2) an addition of one or more nucleotides to a CSAPTP gene; 3) a substitution of one or more nucleotides of a CSAPTP gene, 4) a chromosomal rearrangement of a CSAPTP gene; 5) an alteration in the level of a messenger RNA transcript of a CSAPTP gene, 6) aberrant modification of a CSAPTP gene, such as of the methylation pattern of the genomic DNA, 7) the presence of a non-wild type splicing pattern of a messenger RNA transcript of a CSAPTP gene, 8) a non-wild type level of a CSAPTP-protein, 9) allelic loss of a CSAPTP gene, and 10) inappropriate post-translational modification of a CSAPTP-protein. As described herein, there are a large number of assay techniques known in the art which can be used for detecting alterations in a CSAPTP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the CSAPTP-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CSAPTP gene under conditions such that hybridization and amplification of the CSAPTP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CSAPTP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in CSAPTP can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in CSAPTP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CSAPTP gene and detect mutations by comparing the sequence of the sample CSAPTP with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the CSAPTP gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type CSAPTP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CSAPTP cDNAs obtained from samples of cells. For example, the mut Y enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a CSAPTP sequence, e.g., a wild-type CSAPTP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CSAPTP genes. For example, single strand conformation polymorphism (SSCP) may be used to detect differences in electrophoretic mobility between mutant and wild type nucleic acids (Orita et al. (1989) *Proc Natl. Acad Sci USA*: 86:2766, see also Cotton (1993) *Mutat Res* 285:125–144; and Hayashi (1992) *Genet Anal Tech Appl* 9:73–79). Single-stranded DNA fragments of sample and control CSAPTP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3'end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CSAPTP gene.

Furthermore, any cell type or tissue in which CSAPTP is expressed may be utilized in the prognostic assays described herein.

3. Monitoring of Effects During Clinical Trials

Monitoring the influence of agents (e.g., drugs, compounds) on the expression or activity of a CSAPTP protein (e.g., modulation of cell proliferation, e.g., dephosphorylation of phosphorylated cell cycle proteins) can be applied not only in basic drug screening, but also in clinical trials. For example, the effectiveness of an agent determined by a screening assay as described herein to increase CSAPTP gene expression, protein levels, or upregulate CSAPTP activity, can be monitored in clinical trials of subjects exhibiting decreased CSAPTP gene expression, protein levels, or downregulated CSAPTP activity. Alternatively, the effectiveness of an agent determined by a screening assay to decrease CSAPTP gene expression, protein levels, or downregulate CSAPTP activity, can be monitored in clinical trials of subjects exhibiting increased CSAPTP gene expression, protein levels, or upregulated CSAPTP activity. In such clinical trials, the expression or activity of a CSAPTP gene, and preferably, other genes that have been implicated in, for example, a developmental disorder can be used as a "read out" or markers of the phenotype of a particular cell.

For example, and not by way of limitation, genes, including CSAPTP, that are modulated in cells by treatment with an agent (e.g., compound, drug or small molecule) which modulates CSAPTP activity (e.g., identified in a screening assay as described herein) can be identified. Thus, to study the effect of agents on proliferative disorders, for example, in a clinical trial, cells can be isolated and RNA prepared and analyzed for the levels of expression of CSAPTP and other genes implicated in a proliferative or metabolic disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CSAPTP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CSAPTP protein, mRNA, or genomic DNA in the preadministration sample; (iii) obtaining one or more post-administration samples from the subject; (iv) detecting the level of expression or activity of the CSAPTP protein, mRNA, or genomic DNA in the post-administration samples; (v) comparing the level of expression or activity of the CSAPTP protein, mRNA, or genomic DNA in the pre-administration sample with the CSAPTP protein, mRNA, or genomic DNA in the post administration sample or samples; and (vi) altering the administration of the agent to the subject accordingly. For example, increased administration of the agent may be desirable to increase the expression or activity of CSAPTP to higher levels than detected, i.e., to increase the effectiveness of the agent. Alternatively, decreased administration of the agent may be desirable to decrease expression or activity of CSAPTP to lower levels than detected, i.e. to decrease the effectiveness of the agent. According to such an embodiment, CSAPTP expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant CSAPTP expression or activity. With regards to both prophylactic and therapeutic methods of treatment, such treatments may be specifically tailored or modified, based on knowledge obtained from the field of pharmacogenomics. "Pharmacogenomics", as used herein, includes the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the CSAPTP molecules of the present invention or CSAPTP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant CSAPTP expression or activity, by administering to the subject a CSAPTP or an agent which modulates CSAPTP expression or at least one CSAPTP activity. Subjects at risk for a disease which is caused or contributed to by aberrant CSAPTP expression or activity can be identified by, for example, any or a combination of diagnostic or prognostic assays as described herein. Administration of a prophylactic agent can occur prior to the manifestation of symptoms characteristic of the CSAPTP aberrancy, such that a disease or disorder is prevented or, alternatively, delayed in its progression. Depending on the type of CSAPTP aberrancy, for example, a CSAPTP, CSAPTP agonist or CSAPTP antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating CSAPTP expression or activity for therapeutic purposes. Accordingly, in an exemplary embodiment, the modulatory method of the invention involves contacting a cell with a CSAPTP or agent that modulates one or more of the activities of CSAPTP protein activity associated with the cell. An agent that modulates CSAPTP protein activity can be an agent as described herein, such as a nucleic acid or a protein, a naturally-occurring target molecule of a CSAPTP protein, a CSAPTP antibody, a CSAPTP agonist or antagonist, a peptidomimetic of a CSAPTP agonist or antagonist, or other small molecule. In one embodiment, the agent stimulates one or more CSAPTP activities. Examples of such stimulatory agents include active CSAPTP protein and a nucleic acid molecule encoding CSAPTP that has been introduced into the cell. In another embodiment, the agent inhibits one or more CSAPTP activities. Examples of such inhibitory agents include antisense CSAPTP nucleic acid molecules, anti-CSAPTP antibodies, and CSAPTP inhibitors. These modulatory methods can be performed in vitro (e.g., by culturing the cell with the agent), in vivo (e.g, by administering the agent to a subject), or alternatively in situ (e.g., at the site of lesion or injury, for example, in the hematopoietic system, e.g., bone marrow). As such, the present invention provides methods of treating an individual afflicted with a disease or disorder characterized by aberrant expression or activity of a CSAPTP protein or nucleic acid molecule. In one embodiment, the method involves administering an agent (e.g., an agent identified by a screening assay described herein), or combination of agents that modulates (e.g., upregulates or downregulates) CSAPTP expression or activity. In another embodiment, the method involves administering a CSAPTP protein or nucleic acid molecule as therapy to compensate for reduced or aberrant CSAPTP expression or activity.

Stimulation of CSAPTP activity is desirable in situations in which CSAPTP is abnormally downregulated and/or in which increased CSAPTP activity is likely to have a beneficial effect. For example, stimulation of CSAPTP activity is desirable in situations in which a CSAPTP is downregulated and/or in which increased CSAPTP activity is likely to have a beneficial effect. Likewise, inhibition of CSAPTP activity is desirable in situations in which CSAPTP is abnormally upregulated and/or in which decreased CSAPTP activity is likely to have a beneficial effect.

3. Pharmacogenomics

The CSAPTP molecules of the present invention, as well as agents, or modulators which have a stimulatory or inhibitory effect on CSAPTP activity (e.g., CSAPTP gene expression) as identified by a screening assay described herein can be administered to individuals to treat (prophylactically or therapeutically) disorders associated with aberrant CSAPTP activity (e.g., a proliferative disorder). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a CSAPTP molecule or CSAPTP modulator as well as tailoring the dosage and/or therapeutic regimen of treatment with a CSAPTP molecule or CSAPTP modulator.

Pharmacogenomics deals with clinically significant hereditary variations in the response to drugs due to altered drug disposition and abnormal action in affected persons. See e.g., Eichelbaum, M., *Clin Exp Pharmacol Physiol*, 1996, 23(10–11): 983–985 and Linder, M. W., *Clin Chem*, 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a CSAPTP protein or CSAPTP receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a CSAPTP molecule or CSAPTP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a CSAPTP molecule or CSAPTP modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of Human CSAPTP-1, CSAPTP-2, and CSAPTP-3 cDNAs In this example, the identification and characterization of the genes encoding human CSAPTP-1, CSAPTP-2, and CSAPTP-3 (also referred to as b003g03, b307d02, and b067c02, respectively) is described.

Isolation of the human CSAPTP cDNA

The invention is based, at least in part, on the discovery of four human genes encoding members of the CSAPTP family. The human CSAPTP family members were isolated from cDNA libraries which were prepared from tissue obtained from subjects suffering from congestive heart failure of ischemic and idiopathic origin. Briefly, a cardiac tissue sample was obtained from a biopsy of a patient suffering from congestive heart failure. mRNA was isolated from the cardiac tissue and a cDNA library was prepared therefrom using art known methods (described in, for example, *Molecular Cloning A Laboratory Manual*, 2nd Ed., ed. by Sambrook, Fritsch and Maniatis (Cold Spring Harbor Laboratory Press: 1989). Positive clones were isolated either by examining the top protein blast hit for each sequence, by blasting the libraries against known phosphatases, or by using a computer program that recognizes protein motifs of phosphatases.

The sequences of the positive clones were determined and found to contain open reading frames. The nucleotide sequences encoding the human CSAPTP-1, CSAPTP-2, and CSAPTP-3 protein respectively are shown in FIGS. 1–3 and are set forth as SEQ ID NO:1, SEQ ID NO:4, and SEQ ID NO:7. The full length proteins encoded by these nucleic acids comprise about 172, 263, and 209 amino acids respectively, and has the amino acid sequence shown in FIGS. 1, 2, and 3 respectively and set forth as SEQ ID NO:2, SEQ ID NO:5, and SEQ ID NO:8 respectively. The coding region (open reading frame) of SEQ ID NO:1, SEQ ID NO:4, and SEQ ID NO:7 is set forth as SEQ ID NO:3, SEQ ID NO:5, and SEQ ID NO:8 respectively.

Analysis of human CSAPTP

A BLAST search (Altschul et al. (1990) *J. Mol. Biol.* 215:403) of the nucleotide and protein sequences of human CSAPTP-1 revealed that CSAPTP-1 is similar to the following protein: human protein tyrosine phosphatase (Accession No. AAB4-597) (SEQ ID NO:20). The CSAPTP-1 nucleic acid sequence is approximately 38.7% identical to that of human protein tyrosine phosphatase, as is shown in FIG. 4. The CSAPTP-1 protein sequence is approximately 78.6% identical (over amino acids 1–173) to that of human protein tyrosine phosphatase, as is shown in FIG. 5.

CSAPTP-2 is similar to the following protein: dual specificity protein phosphatase VHR (Accession No. P51452) (SEQ ID NO:21). The CSAPTP-2 protein is approximately 22.5% identical (overmino acids 1–263) at the amino acid level to dual specificity protein phosphatase VHR as is shown in FIG. 6.

CSAPTP-3 is similar to the following proteins: dual specificity phosphatase 2 (Accession No. B57126, Q05922) (SEQ ID NO:22), and C. elegans protein F28C6.8 (Accession No. Z68315) (SEQ ID NO:23). The CSAPTP-3 protein is approximately 50% identical (over amino acids 118–155) and 29% identical over amino acids 54–97) to mouse dual specificity phosphatase 2. The CSAPTP-3 protein is approximately 46% identical (over amino acids 6–20 and 50–64) and 41% identical (over amino acids 20–36) to BIIIA3. The CSAPTP-3 protein is approximately 50% identical (over amino acids 183–194), 42% identical (over amino acids 92–155) and 39% identical (over amino acids 60–92) to F28C6.8, as is shown in FIG. 7.

Tissue Distribution of CSAPTP mRNA

This Example describes the tissue distribution of CSAPTP mRNA, as determined by Northern blot hybridizations.

Northern blot hybridizations with the various RNA samples were performed under standard conditions and washed under stringent conditions, i.e., 0.2×SSC at 65° C. A DNA probes corresponding to CSAPTP-1 (Achrb003g03), CSAPTP-2 (fchr037d02), CSAPTP-3 (fchr067c02) were used. The DNA was radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations.

CSAPTP-1 message was detected in human heart and skeletal, in all rat tissues but predominantly in rat skeletal muscle, heart, placenta, lung and brain. CSAPTP-2 message was detected in human with highest expression in skeletal muscle with some expression in heart and brain muscle, while in the rat expression was mainly found in skeletal muscle. CSAPTP-3 message was detected in human in highest in heart and skeletal and also found in brain, placenta, kidney and pancreas.

Example 2

Expression of Recombinant CSAPTP Protein in Bacterial Cells

In this example, CSAPTP is expressed as a recombinant glutathione-S-transferase (GST) fusion polypeptide in *E. coli* and the fusion polypeptide is isolated and characterized. Specifically, CSAPTP is fused to GST and this fusion polypeptide is expressed in *E. coli*, e.g., strain PEB 199. Expression of the GST-CSAPTP fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant CSAPTP Protein in COS Cells

To express the CSAPTP gene in COS cells, the pCDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire CSAPTP protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the CSAPTP DNA sequence is amplified by PCR using two primers. The 5' primer contains the restriction site of interest followed by approximately twenty nucleotides of the CSAPTP coding sequence starting from the initiation codon; the 3' end sequence contains complementary sequences to the other restriction site of interest, a translation stop codon, the HA tag or FLAG tag and the last 20 nucleotides of the CSAPTP coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the CSAPTP gene is inserted in the correct orientation. The ligation mixture is transformed into *E. coli* cells (strains HB 101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the CSAPTP-pCDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the CSAPTP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the CSAPTP coding sequence is cloned directly into the polylinker of the pCDNA/Amp vector using the appropriate restriction sites. The resulting plasmid is transfected into COS cells in the manner described above, and the expression of the CSAPTP polypeptide is detected by radiolabelling and immunoprecipitation using a CSAPTP specific monoclonal antibody.

Equivalents

SEQUENCE LISTING

<160> NUMBER OF SEQ ID NOS: 23

<210> SEQ ID NO 1
<211> LENGTH: 1315
<212> TYPE: DNA
<213> ORGANISM: Homo sapiens
<220> FEATURE:
<221> NAME/KEY: CDS
<222> LOCATION: (249)..(767)
<223> OTHER INFORMATION: 'n' at position 1315 may be any nucleotide -continued

```
<400> SEQUENCE: 1
gtcgacccac gcgtccgtgg gttttctttt ttaattatcc aaacagtggg cagcttcctc      60
ccccacaccc aagtatttgc acaatatttg tgcggggtat gggggtgggt ttttaaatct     120
cgtttctctt ggacaagcac aaggatctcg ttctcctcat tttttggggg tgtgtgggga     180
cttctcaggt cgtgtcccca gccttctctg cagtcccttc tgccctgccg ggcccgtcgg     240 gaggcgcc atg gct cgg atg aac cgc ccg gcc ccg gtg gag gtg agc tac     290
         Met Ala Arg Met Asn Arg Pro Ala Pro Val Glu Val Ser Tyr
           1               5                  10 aaa cac atg cgc ttc ctc atc acc cac aac ccc acc aac gcc acg ctc      338
Lys His Met Arg Phe Leu Ile Thr His Asn Pro Thr Asn Ala Thr Leu
 15              20                  25                  30 agc acc ttc att gag gac ctg aag aag tac ggg gct acc act gtg gtg      386
Ser Thr Phe Ile Glu Asp Leu Lys Lys Tyr Gly Ala Thr Thr Val Val
                 35                  40                  45 cgt gtg tgt gaa gtg acc tat gac aaa acg ccg ctg gag aag gat ggc      434
Arg Val Cys Glu Val Thr Tyr Asp Lys Thr Pro Leu Glu Lys Asp Gly
             50                  55                  60 atc acc gtt gtg gac tgg ccg ttt gac gat ggg gcg ccc ccg ccc ggc      482
Ile Thr Val Val Asp Trp Pro Phe Asp Asp Gly Ala Pro Pro Pro Gly
 65                  70                  75 aag gta gtg gaa gac tgg ctg agc ctg gtg aag gcc aag ttc tgt gag      530
Lys Val Val Glu Asp Trp Leu Ser Leu Val Lys Ala Lys Phe Cys Glu
 80                  85                  90 gcc ccc ggc agc tgc gtg gct gtg cac tgc gtg gcg ggc ctg ggc cgg      578
Ala Pro Gly Ser Cys Val Ala Val His Cys Val Ala Gly Leu Gly Arg
 95                 100                 105                 110 gct cca gtc ctt gtg gcg ctg gcc ctt att gag agc ggg atg aag tac      626
Ala Pro Val Leu Val Ala Leu Ala Leu Ile Glu Ser Gly Met Lys Tyr
                115                 120                 125 gag gac gcc atc cag ttc atc cgc cag aag cgc cgc gga gcc atc aac      674
Glu Asp Ala Ile Gln Phe Ile Arg Gln Lys Arg Arg Gly Ala Ile Asn
            130                 135                 140 agc aag cag ctc acc tac ctg gag aaa tac cgg ccc aaa cag agg ctg      722
Ser Lys Gln Leu Thr Tyr Leu Glu Lys Tyr Arg Pro Lys Gln Arg Leu
            145                 150                 155 cgg ttc aaa gac cca cac acg cac aag acc cgg tgc tgc gtt atg          767
Arg Phe Lys Asp Pro His Thr His Lys Thr Arg Cys Cys Val Met
            160                 165                 170 tagctcagga ccttggctgg gcctggtcgt catgtaggtc aggaccttgg ctggacctgg     827
aggccctgcc cagccctgct ctgcccagcc cagcaggggc tccaggcctt ggctggcccc     887
acatcgcctt ttcctccccg acacctccgt gcacttgtgt ccgaggagcg aggagcccct     947
cgggccctgg gtggcctctg ggccctttct cctgtctccg ccactccctc tggcggcgct    1007
ggccgtggct ctgtctctct gaggtgggtc gggcgccctc tgcccgcccc ctcccacacc    1067
agccaggctg gtctcctcta gcctgtttgt tgtggggtgg gggtatattt tgtaaccact    1127
gggcccccag cccctctttt gcgacccctt gtcctgacct gttctcggca ccttaaatta    1187
ttagaccccg gggcagtcag gtgctccgga cacccgaagg caataaaaca ggagccgtga    1247
aaaaaaaaaa aaaaaaaaaa aaaaaaaaaa aaaaaaaaaa aaaaaaaaaa aaaaaaaagg    1307 gcggccgn                                                             1315

<210> SEQ ID NO 2
<211> LENGTH: 173
<212> TYPE: PRT
```

<213> ORGANISM: Homo sapiens

<400> SEQUENCE: 2

```
Met Ala Arg Met Asn Arg Pro Ala Pro Val Glu Val Ser Tyr Lys His
 1               5                  10                  15

Met Arg Phe Leu Ile Thr His Asn Pro Thr Asn Ala Thr Leu Ser Thr
                20                  25                  30

Phe Ile Glu Asp Leu Lys Lys Tyr Gly Ala Thr Thr Val Val Arg Val
            35                  40                  45

Cys Glu Val Thr Tyr Asp Lys Thr Pro Leu Glu Lys Asp Gly Ile Thr
        50                  55                  60

Val Val Asp Trp Pro Phe Asp Asp Gly Ala Pro Pro Gly Lys Val
 65                  70                  75                  80

Val Glu Asp Trp Leu Ser Leu Val Lys Ala Lys Phe Cys Glu Ala Pro
                85                  90                  95

Gly Ser Cys Val Ala Val His Cys Val Ala Gly Leu Gly Arg Ala Pro
            100                 105                 110

Val Leu Val Ala Leu Ala Leu Ile Glu Ser Gly Met Lys Tyr Glu Asp
        115                 120                 125

Ala Ile Gln Phe Ile Arg Gln Lys Arg Arg Gly Ala Ile Asn Ser Lys
    130                 135                 140

Gln Leu Thr Tyr Leu Glu Lys Tyr Arg Pro Lys Gln Arg Leu Arg Phe
145                 150                 155                 160

Lys Asp Pro His Thr His Lys Thr Arg Cys Cys Val Met
                165                 170
```

<210> SEQ ID NO 3
<211> LENGTH: 510
<212> TYPE: DNA
<213> ORGANISM: Homo sapiens
<220> FEATURE:
<221> NAME/KEY: CDS
<222> LOCATION: (1)..(510)

<400> SEQUENCE: 3

```
atg aac cgc ccg gcc ccg gtg gag gtg agc tac aaa cac atg cgc ttc      48
Met Asn Arg Pro Ala Pro Val Glu Val Ser Tyr Lys His Met Arg Phe
 1               5                  10                  15 ctc atc acc cac aac ccc acc aac gcc acg ctc agc acc ttc att gag      96
Leu Ile Thr His Asn Pro Thr Asn Ala Thr Leu Ser Thr Phe Ile Glu
                20                  25                  30 gac ctg aag aag tac ggg gct acc act gtg gtg cgt gtg tgt gaa gtg     144
Asp Leu Lys Lys Tyr Gly Ala Thr Thr Val Val Arg Val Cys Glu Val
            35                  40                  45 acc tat gac aaa acg ccg ctg gag aag gat ggc atc acc gtt gtg gac     192
Thr Tyr Asp Lys Thr Pro Leu Glu Lys Asp Gly Ile Thr Val Val Asp
        50                  55                  60 tgg ccg ttt gac gat ggg gcg ccc ccg ccc ggc aag gta gtg gaa gac     240
Trp Pro Phe Asp Asp Gly Ala Pro Pro Pro Gly Lys Val Val Glu Asp
 65                  70                  75                  80 tgg ctg agc ctg gtg aag gcc aag ttc tgt gag gcc ccc ggc agc tgc     288
Trp Leu Ser Leu Val Lys Ala Lys Phe Cys Glu Ala Pro Gly Ser Cys
                85                  90                  95 gtg gct gtg cac tgc gtg gcg ggc ctg ggc cgg gct cca gtc ctt gtg     336
Val Ala Val His Cys Val Ala Gly Leu Gly Arg Ala Pro Val Leu Val
            100                 105                 110 gcg ctg gcc ctt att gag agc ggg atg aag tac gag gac gcc atc cag     384
Ala Leu Ala Leu Ile Glu Ser Gly Met Lys Tyr Glu Asp Ala Ile Gln
        115                 120                 125
```

```
ttc atc cgc cag aag cgc cgc gga gcc atc aac agc aag cag ctc acc      432
Phe Ile Arg Gln Lys Arg Arg Gly Ala Ile Asn Ser Lys Gln Leu Thr
    130                 135                 140 tac ctg gag aaa tac cgg ccc aaa cag agg ctg cgg ttc aaa gac cca      480
Tyr Leu Glu Lys Tyr Arg Pro Lys Gln Arg Leu Arg Phe Lys Asp Pro
145                 150                 155                 160 cac acg cac aag acc cgg tgc tgc gtt atg                              510
His Thr His Lys Thr Arg Cys Cys Val Met
                165                 170

<210> SEQ ID NO 4
<211> LENGTH: 1016
<212> TYPE: DNA
<213> ORGANISM: Homo sapiens
<220> FEATURE:
<221> NAME/KEY: CDS
<222> LOCATION: (1)..(789)

<400> SEQUENCE: 4 gtc gac cca cgc gtc cgg cgg ctc ctc tac aca ggc aag aca gcc tgt       48
Val Asp Pro Arg Val Arg Arg Leu Leu Tyr Thr Gly Lys Thr Ala Cys
  1               5                  10                  15 aac cat gcc gac gag gtc tgg cca ggc ctc tat ctc gga gac cag gac       96
Asn His Ala Asp Glu Val Trp Pro Gly Leu Tyr Leu Gly Asp Gln Asp
                 20                  25                  30 atg gct aac aac cgc cgg gag ctt cgc cgc ctg ggc atc acg cac gtc      144
Met Ala Asn Asn Arg Arg Glu Leu Arg Arg Leu Gly Ile Thr His Val
             35                  40                  45 ctc aat gcc tca cac agc cgg tgg cga ggc acg ccc gag gcc tat gag      192
Leu Asn Ala Ser His Ser Arg Trp Arg Gly Thr Pro Glu Ala Tyr Glu
         50                  55                  60 ggg ctg ggc atc cgc tac ctg ggt gtt gag gcc cac gac tcg cca gcc      240
Gly Leu Gly Ile Arg Tyr Leu Gly Val Glu Ala His Asp Ser Pro Ala
 65                  70                  75                  80 ttt gac atg agc atc cac ttc cag acg gct gcc gac ttc atc cac cgg      288
Phe Asp Met Ser Ile His Phe Gln Thr Ala Ala Asp Phe Ile His Arg
                 85                  90                  95 gcg ctg agc cag cca gga ggg aag atc ctg gtg cat tgt gct gtg ggc      336
Ala Leu Ser Gln Pro Gly Gly Lys Ile Leu Val His Cys Ala Val Gly
            100                 105                 110 gtg agc cga tcc gcc acc ctg gta ctg gcc tac ctc atg ctg tac cac      384
Val Ser Arg Ser Ala Thr Leu Val Leu Ala Tyr Leu Met Leu Tyr His
        115                 120                 125 cac ctt acc ctc gtg gag gcc atc aag aaa gtc aaa gac cac cga gga      432
His Leu Thr Leu Val Glu Ala Ile Lys Lys Val Lys Asp His Arg Gly
    130                 135                 140 gag gcc gag ccc cag gcc act gtc act ctt tgt ggg agg gga cgg gga      480
Glu Ala Glu Pro Gln Ala Thr Val Thr Leu Cys Gly Arg Gly Arg Gly
145                 150                 155                 160 gtg agg ttg ggc agt gtg gtg gat ggg cac cca gga agg gtt gac cag      528
Val Arg Leu Gly Ser Val Val Asp Gly His Pro Gly Arg Val Asp Gln
                165                 170                 175 gga agg agg cag cta ggc tgt aga tgg aag atg gtc ctg gga ttc gaa      576
Gly Arg Arg Gln Leu Gly Cys Arg Trp Lys Met Val Leu Gly Phe Glu
            180                 185                 190 cac cgc tgg gat ctg gcc agg gtg ctc cct ggg att cac agt ccc ttc      624
His Arg Trp Asp Leu Ala Arg Val Leu Pro Gly Ile His Ser Pro Phe
        195                 200                 205 ccc tct ttg tgc cca agt gtt tcc ctc tct ccc tca cca aaa aca aaa      672
Pro Ser Leu Cys Pro Ser Val Ser Leu Ser Pro Ser Pro Lys Thr Lys
    210                 215                 220
```

-continued

```
agg gcc atc tct gcc cct gca ctt tgt gca gaa agt cag gga tac ggc    720
Arg Ala Ile Ser Ala Pro Ala Leu Cys Ala Glu Ser Gln Gly Tyr Gly
225             230                 235                 240 aag cat gaa tgc aat ggt gta gag ttg tgt gaa acc cct agc ata gag    768
Lys His Glu Cys Asn Gly Val Glu Leu Cys Glu Thr Pro Ser Ile Glu
                245                 250                 255 aca gac agc gaa gag atg gtg tgaaaagctt gcagaaccag acagagaacc      819
Thr Asp Ser Glu Glu Met Val
                260 ccacagactt tccactccaa gcacaggagg aggtagctag cgtgtgaggg ttggcactag   879 gcccacggct gctgcttggg ccaaaaacat acagaggtgc atggctggca gtcttgaaat   939 tgtcactcgc ttactggatc caagcgtctc gaggataaat aaagatcatg aaaaaaaaaa   999 aaaaaaaggg cggccgc                                                1016
```

<210> SEQ ID NO 5
<211> LENGTH: 263
<212> TYPE: PRT
<213> ORGANISM: Homo sapiens

<400> SEQUENCE: 5

```
Val Asp Pro Arg Val Arg Arg Leu Leu Tyr Thr Gly Lys Thr Ala Cys
1               5                   10                  15

Asn His Ala Asp Glu Val Trp Pro Gly Leu Tyr Leu Gly Asp Gln Asp
            20                  25                  30

Met Ala Asn Asn Arg Arg Glu Leu Arg Arg Leu Gly Ile Thr His Val
        35                  40                  45

Leu Asn Ala Ser His Ser Arg Trp Arg Gly Thr Pro Glu Ala Tyr Glu
    50                  55                  60

Gly Leu Gly Ile Arg Tyr Leu Gly Val Glu Ala His Asp Ser Pro Ala
65                  70                  75                  80

Phe Asp Met Ser Ile His Phe Gln Thr Ala Ala Asp Phe Ile His Arg
                85                  90                  95

Ala Leu Ser Gln Pro Gly Gly Lys Ile Leu Val His Cys Ala Val Gly
            100                 105                 110

Val Ser Arg Ser Ala Thr Leu Val Leu Ala Tyr Leu Met Leu Tyr His
        115                 120                 125

His Leu Thr Leu Val Glu Ala Ile Lys Lys Val Lys Asp His Arg Gly
    130                 135                 140

Glu Ala Glu Pro Gln Ala Thr Val Thr Leu Cys Gly Arg Gly Arg Gly
145                 150                 155                 160

Val Arg Leu Gly Ser Val Val Asp Gly His Pro Gly Arg Val Asp Gln
                165                 170                 175

Gly Arg Arg Gln Leu Gly Cys Arg Trp Lys Met Val Leu Gly Phe Glu
            180                 185                 190

His Arg Trp Asp Leu Ala Arg Val Leu Pro Gly Ile His Ser Pro Phe
        195                 200                 205

Pro Ser Leu Cys Pro Ser Val Ser Leu Ser Pro Pro Lys Thr Lys
    210                 215                 220

Arg Ala Ile Ser Ala Pro Ala Leu Cys Ala Glu Ser Gln Gly Tyr Gly
225                 230                 235                 240

Lys His Glu Cys Asn Gly Val Glu Leu Cys Glu Thr Pro Ser Ile Glu
                245                 250                 255

Thr Asp Ser Glu Glu Met Val
            260
```

<210> SEQ ID NO 6
<211> LENGTH: 789
<212> TYPE: DNA
<213> ORGANISM: Homo sapiens
<220> FEATURE:
<221> NAME/KEY: CDS
<222> LOCATION: (1)..(789)

<400> SEQUENCE: 6

| | | | | | | | | | | | | | | | | |
|---|---|---|---|---|---|---|---|---|---|---|---|---|---|---|---|---|
| gtc | gac | cca | cgc | gtc | cgg | cgg | ctc | ctc | tac | aca | ggc | aag | aca | gcc | tgt | 48 |
| Val | Asp | Pro | Arg | Val | Arg | Arg | Leu | Leu | Tyr | Thr | Gly | Lys | Thr | Ala | Cys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aac | cat | gcc | gac | gag | gtc | tgg | cca | ggc | ctc | tat | ctc | gga | gac | cag | gac | 96 |
| Asn | His | Ala | Asp | Glu | Val | Trp | Pro | Gly | Leu | Tyr | Leu | Gly | Asp | Gln | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| atg | gct | aac | aac | cgc | cgg | gag | ctt | cgc | cgc | ctg | ggc | atc | acg | cac | gtc | 144 |
| Met | Ala | Asn | Asn | Arg | Arg | Glu | Leu | Arg | Arg | Leu | Gly | Ile | Thr | His | Val | |
| | | | 35 | | | | | 40 | | | | | 45 | | | |

| | | | | | | | | | | | | | | | | |
|---|---|---|---|---|---|---|---|---|---|---|---|---|---|---|---|---|
| ctc | aat | gcc | tca | cac | agc | cgg | tgg | cga | ggc | acg | ccc | gag | gcc | tat | gag | 192 |
| Leu | Asn | Ala | Ser | His | Ser | Arg | Trp | Arg | Gly | Thr | Pro | Glu | Ala | Tyr | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| ggg | ctg | ggc | atc | cgc | tac | ctg | ggt | gtt | gag | gcc | cac | gac | tcg | cca | gcc | 240 |
| Gly | Leu | Gly | Ile | Arg | Tyr | Leu | Gly | Val | Glu | Ala | His | Asp | Ser | Pro | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttt | gac | atg | agc | atc | cac | ttc | cag | acg | gct | gcc | gac | ttc | atc | cac | cgg | 288 |
| Phe | Asp | Met | Ser | Ile | His | Phe | Gln | Thr | Ala | Ala | Asp | Phe | Ile | His | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| gcg | ctg | agc | cag | cca | gga | ggg | aag | atc | ctg | gtg | cat | tgt | gct | gtg | ggc | 336 |
| Ala | Leu | Ser | Gln | Pro | Gly | Gly | Lys | Ile | Leu | Val | His | Cys | Ala | Val | Gly | |
| | | | | 100 | | | | | 105 | | | | | 110 | | |

| | | | | | | | | | | | | | | | | |
|---|---|---|---|---|---|---|---|---|---|---|---|---|---|---|---|---|
| gtg | agc | cga | tcc | gcc | acc | ctg | gta | ctg | gcc | tac | ctc | atg | ctg | tac | cac | 384 |
| Val | Ser | Arg | Ser | Ala | Thr | Leu | Val | Leu | Ala | Tyr | Leu | Met | Leu | Tyr | His | |
| | | | 115 | | | | | 120 | | | | | 125 | | | |

| | | | | | | | | | | | | | | | | |
|---|---|---|---|---|---|---|---|---|---|---|---|---|---|---|---|---|
| cac | ctt | acc | ctc | gtg | gag | gcc | atc | aag | aaa | gtc | aaa | gac | cac | cga | gga | 432 |
| His | Leu | Thr | Leu | Val | Glu | Ala | Ile | Lys | Lys | Val | Lys | Asp | His | Arg | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| gag | gcc | gag | ccc | cag | gcc | act | gtc | act | ctt | tgt | ggg | agg | gga | cgg | gga | 480 |
| Glu | Ala | Glu | Pro | Gln | Ala | Thr | Val | Thr | Leu | Cys | Gly | Arg | Gly | Arg | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtg | agg | ttg | ggc | agt | gtg | gtg | gat | ggg | cac | cca | gga | agg | gtt | gac | cag | 528 |
| Val | Arg | Leu | Gly | Ser | Val | Val | Asp | Gly | His | Pro | Gly | Arg | Val | Asp | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| gga | agg | agg | cag | cta | ggc | tgt | aga | tgg | aag | atg | gtc | ctg | gga | ttc | gaa | 576 |
| Gly | Arg | Arg | Gln | Leu | Gly | Cys | Arg | Trp | Lys | Met | Val | Leu | Gly | Phe | Glu | |
| | | | | 180 | | | | | 185 | | | | | 190 | | |

| | | | | | | | | | | | | | | | | |
|---|---|---|---|---|---|---|---|---|---|---|---|---|---|---|---|---|
| cac | cgc | tgg | gat | ctg | gcc | agg | gtg | ctc | cct | ggg | att | cac | agt | ccc | ttc | 624 |
| His | Arg | Trp | Asp | Leu | Ala | Arg | Val | Leu | Pro | Gly | Ile | His | Ser | Pro | Phe | |
| | | | 195 | | | | | 200 | | | | | 205 | | | |

| | | | | | | | | | | | | | | | | |
|---|---|---|---|---|---|---|---|---|---|---|---|---|---|---|---|---|
| ccc | tct | ttg | tgc | cca | agt | gtt | tcc | ctc | tct | ccc | tca | cca | aaa | aca | aaa | 672 |
| Pro | Ser | Leu | Cys | Pro | Ser | Val | Ser | Leu | Ser | Pro | Ser | Pro | Lys | Thr | Lys | |
| | | 210 | | | | | 215 | | | | | 220 | | | | |

| | | | | | | | | | | | | | | | | |
|---|---|---|---|---|---|---|---|---|---|---|---|---|---|---|---|---|
| agg | gcc | atc | tct | gcc | cct | gca | ctt | tgt | gca | gaa | agt | cag | gga | tac | ggc | 720 |
| Arg | Ala | Ile | Ser | Ala | Pro | Ala | Leu | Cys | Ala | Glu | Ser | Gln | Gly | Tyr | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | cat | gaa | tgc | aat | ggt | gta | gag | ttg | tgt | gaa | acc | cct | agc | ata | gag | 768 |
| Lys | His | Glu | Cys | Asn | Gly | Val | Glu | Leu | Cys | Glu | Thr | Pro | Ser | Ile | Glu | |
| | | | | 245 | | | | | 250 | | | | | 255 | | |

| | | | | | | |
|---|---|---|---|---|---|---|
| aca | gac | agc | gaa | gag | atg | gtg | 789 |
| Thr | Asp | Ser | Glu | Glu | Met | Val | |
| | | | 260 | | | | |

<210> SEQ ID NO 7
<211> LENGTH: 814
<212> TYPE: DNA
<213> ORGANISM: Homo sapiens
<220> FEATURE:
<221> NAME/KEY: CDS
<222> LOCATION: (1)..(627)
<223> OTHER INFORMATION: 'n' at postions
    2,12,496-498,786,803,804,806,808,810 and 811 may
    be any nucleotide
<221> NAME/KEY: misc_feature
<222> LOCATION: (1)..(3)
<223> OTHER INFORMATION: Xaa = any amino acid
<221> NAME/KEY: misc_feature
<222> LOCATION: (10)..(12)
<223> OTHER INFORMATION: Xaa = any amino acid
<221> NAME/KEY: misc_feature
<222> LOCATION: (13)..(15)
<223> OTHER INFORMATION: Xaa = any amino acid
<221> NAME/KEY: misc_feature
<222> LOCATION: (496)..(498)
<223> OTHER INFORMATION: Xaa = any amino acid
<221> NAME/KEY: misc_feature
<222> LOCATION: (589)..(591)
<223> OTHER INFORMATION: Xaa = any amino acid
<221> NAME/KEY: misc_feature
<222> LOCATION: (592)..(594)
<223> OTHER INFORMATION: Xaa = any amino acid
<221> NAME/KEY: misc_feature
<222> LOCATION: (613)..(615)
<223> OTHER INFORMATION: Xaa = any amino acid

<400> SEQUENCE: 7

```
tng gat cga mcn sgc gtc cgg gcg gcc ccg cgc tgc tgg agg ccg gcc    48
Xaa Asp Arg Xaa Xaa Val Arg Ala Ala Pro Arg Cys Trp Arg Pro Ala
 1               5                  10                  15 tgg cgc ggg tgc tct tct acc cga cgc tgc tct aca ccc tgt tcc gcg    96
Trp Arg Gly Cys Ser Ser Thr Arg Arg Cys Ser Thr Pro Cys Ser Ala
             20                  25                  30 gga agg tgc cgg gtc ggg cgc acc ggg act ggt acc acc gca tcg acc   144
Gly Arg Cys Arg Val Gly Arg Thr Gly Thr Gly Thr Thr Ala Ser Thr
         35                  40                  45 cca ccg tgc tgc tgg gcg cgc tgc cgt tgc gga agc ttg acg cgc cag   192
Pro Pro Cys Cys Trp Ala Arg Cys Arg Cys Gly Ser Leu Thr Arg Gln
     50                  55                  60 ctg gta cag gac gag aac gtg cgc ggg gtg atc acc atg aac gag gag   240
Leu Val Gln Asp Glu Asn Val Arg Gly Val Ile Thr Met Asn Glu Glu
 65                  70                  75                  80 tac gag acg agg ttc ctg tgc aac tct tca cag gag tgg aag aga cta   288
Tyr Glu Thr Arg Phe Leu Cys Asn Ser Ser Gln Glu Trp Lys Arg Leu
                 85                  90                  95 gga gtc gag cag ctg cgg ctc agc aca gta gac atg act ggg atc ccc   336
Gly Val Glu Gln Leu Arg Leu Ser Thr Val Asp Met Thr Gly Ile Pro
            100                 105                 110 acc ttg gac aac ctc cag aag gga gtc caa ttt gct ctc aag tac cag   384
Thr Leu Asp Asn Leu Gln Lys Gly Val Gln Phe Ala Leu Lys Tyr Gln
        115                 120                 125 tcg ctg ggc cag tgt gtt tac gtg cat tgt aag gct ggg cgc tcc agg   432
Ser Leu Gly Gln Cys Val Tyr Val His Cys Lys Ala Gly Arg Ser Arg
    130                 135                 140 agt gcc act atg gtg gca gca tac ctg att cag gtt gca caa atg gga   480
Ser Ala Thr Met Val Ala Ala Tyr Leu Ile Gln Val Ala Gln Met Gly
145                 150                 155                 160 gtc cag agg agg ctg nnn gag cca tcg ccc aag atc cgg gtc ata cat   528
Val Gln Arg Arg Leu Xaa Glu Pro Ser Pro Lys Ile Arg Val Ile His
                165                 170                 175
```

```
cca cat cag gcc tgg cca gct tgg atg ttc tta aag agt tcc aca aag    576
Pro His Gln Ala Trp Pro Ala Trp Met Phe Leu Lys Ser Ser Thr Lys
        180                 185                 190 cag att act gca csg gcm aca aag gat ggg act ttt gkc att tca aag    624
Gln Ile Thr Ala Xaa Xaa Thr Lys Asp Gly Thr Phe Xaa Ile Ser Lys
            195                 200                 205 aca tgatgtatgg ggattagaaa gaactcaaga cactcctgct tgatacagaa         677
Thr caaaagagc ttaacaggac caacagggct taagcccaga cttgacgtaa cagaaatgtg   737
ccaataggta ataggtaatt tttctttctc tgacttgttt tgttttctna aatggcactg  797
ttgaannant ntnnctc                                                 814
```

<210> SEQ ID NO 8
<211> LENGTH: 209
<212> TYPE: PRT
<213> ORGANISM: Homo sapiens
<220> FEATURE:
<221> NAME/KEY: misc_feature
<222> LOCATION: (1)..(3)
<223> OTHER INFORMATION: Xaa = any amino acid
<221> NAME/KEY: misc_feature
<222> LOCATION: (10)..(12)
<223> OTHER INFORMATION: Xaa = any amino acid
<221> NAME/KEY: misc_feature
<222> LOCATION: (13)..(15)
<223> OTHER INFORMATION: Xaa = any amino acid
<221> NAME/KEY: misc_feature
<222> LOCATION: (496)..(498)
<223> OTHER INFORMATION: Xaa = any amino acid
<221> NAME/KEY: misc_feature
<222> LOCATION: (589)..(591)
<223> OTHER INFORMATION: Xaa = any amino acid
<221> NAME/KEY: misc_feature
<222> LOCATION: (592)..(594)
<223> OTHER INFORMATION: Xaa = any amino acid
<221> NAME/KEY: misc_feature
<222> LOCATION: (613)..(615)
<223> OTHER INFORMATION: Xaa = any amino acid

<400> SEQUENCE: 8

```
Xaa Asp Arg Xaa Xaa Val Arg Ala Ala Pro Arg Cys Trp Arg Pro Ala
 1               5                  10                  15

Trp Arg Gly Cys Ser Ser Thr Arg Cys Ser Thr Pro Cys Ser Ala
             20                  25                  30

Gly Arg Cys Arg Val Gly Arg Thr Gly Thr Gly Thr Thr Ala Ser Thr
         35                  40                  45

Pro Pro Cys Cys Trp Ala Arg Cys Arg Cys Gly Ser Leu Thr Arg Gln
     50                  55                  60

Leu Val Gln Asp Glu Asn Val Arg Gly Val Ile Thr Met Asn Glu Glu
 65                  70                  75                  80

Tyr Glu Thr Arg Phe Leu Cys Asn Ser Ser Gln Glu Trp Lys Arg Leu
                 85                  90                  95

Gly Val Glu Gln Leu Arg Leu Ser Thr Val Asp Met Thr Gly Ile Pro
            100                 105                 110

Thr Leu Asp Asn Leu Gln Lys Gly Val Gln Phe Ala Leu Lys Tyr Gln
        115                 120                 125

Ser Leu Gly Gln Cys Val Tyr Val His Cys Lys Ala Gly Arg Ser Arg
    130                 135                 140

Ser Ala Thr Met Val Ala Ala Tyr Leu Ile Gln Val Ala Gln Met Gly
145                 150                 155                 160

Val Gln Arg Arg Leu Xaa Glu Pro Ser Pro Lys Ile Arg Val Ile His
```

```
                    165                 170                 175
Pro His Gln Ala Trp Pro Ala Trp Met Phe Leu Lys Ser Ser Thr Lys
                180                 185                 190

Gln Ile Thr Ala Xaa Xaa Thr Lys Asp Gly Thr Phe Xaa Ile Ser Lys
            195                 200                 205

Thr

<210> SEQ ID NO 9
<211> LENGTH: 627
<212> TYPE: DNA
<213> ORGANISM: Homo sapiens
<220> FEATURE:
<221> NAME/KEY: CDS
<222> LOCATION: (1)..(627)
<223> OTHER INFORMATION: 'n' at positions 2,12, and 496-498 may be any
      nucleotide
<221> NAME/KEY: misc_feature
<222> LOCATION: (1)..(3)
<223> OTHER INFORMATION: Xaa = any amino acid
<221> NAME/KEY: misc_feature
<222> LOCATION: (10)..(12)
<223> OTHER INFORMATION: Xaa = any amino acid
<221> NAME/KEY: misc_feature
<222> LOCATION: (13)..(15)
<223> OTHER INFORMATION: Xaa = any amino acid
<221> NAME/KEY: misc_feature
<222> LOCATION: (496)..(498)
<223> OTHER INFORMATION: Xaa = any amino acid
<221> NAME/KEY: misc_feature
<222> LOCATION: (589)..(591)
<223> OTHER INFORMATION: Xaa = any amino acid
<221> NAME/KEY: misc_feature
<222> LOCATION: (592)..(594)
<223> OTHER INFORMATION: Xaa = any amino acid

<400> SEQUENCE: 9 tng gat cga mcn sgc gtc cgg gcg gcc ccg cgc tgc tgg agg ccg gcc      48
Xaa Asp Arg Xaa Xaa Val Arg Ala Ala Pro Arg Cys Trp Arg Pro Ala
 1               5                  10                  15 tgg cgc ggg tgc tct tct acc cga cgc tgc tct aca ccc tgt tcc gcg      96
Trp Arg Gly Cys Ser Ser Thr Arg Arg Cys Ser Thr Pro Cys Ser Ala
                20                  25                  30 gga agg tgc cgg gtc ggg cgc acc ggg act ggt acc acc gca tcg acc     144
Gly Arg Cys Arg Val Gly Arg Thr Gly Thr Gly Thr Thr Ala Ser Thr
            35                  40                  45 cca ccg tgc tgc tgg gcg cgc tgc cgt tgc gga agc ttg acg cgc cag     192
Pro Pro Cys Cys Trp Ala Arg Cys Arg Cys Gly Ser Leu Thr Arg Gln
    50                  55                  60 ctg gta cag gac gag aac gtg cgc ggg gtg atc acc atg aac gag gag     240
Leu Val Gln Asp Glu Asn Val Arg Gly Val Ile Thr Met Asn Glu Glu
65                  70                  75                  80 tac gag acg agg ttc ctg tgc aac tct tca cag gag tgg aag aga cta     288
Tyr Glu Thr Arg Phe Leu Cys Asn Ser Ser Gln Glu Trp Lys Arg Leu
                85                  90                  95 gga gtc gag cag ctg cgg ctc agc aca gta gac atg act ggg atc ccc     336
Gly Val Glu Gln Leu Arg Leu Ser Thr Val Asp Met Thr Gly Ile Pro
            100                 105                 110 acc ttg gac aac ctc cag aag gga gtc caa ttt gct ctc aag tac cag     384
Thr Leu Asp Asn Leu Gln Lys Gly Val Gln Phe Ala Leu Lys Tyr Gln
        115                 120                 125 tcg ctg ggc cag tgt gtt tac gtg cat tgt aag gct ggg cgc tcc agg     432
Ser Leu Gly Gln Cys Val Tyr Val His Cys Lys Ala Gly Arg Ser Arg
    130                 135                 140 agt gcc act atg gtg gca gca tac ctg att cag gtt gca caa atg gga     480
Ser Ala Thr Met Val Ala Ala Tyr Leu Ile Gln Val Ala Gln Met Gly
145                 150                 155                 160
```

```
                 145                150                155                160
gtc cag agg agg ctg nnn gag cca tcg ccc aag atc cgg gtc ata cat    528
Val Gln Arg Arg Leu Xaa Glu Pro Ser Pro Lys Ile Arg Val Ile His
                    165                170                175 cca cat cag gcc tgg cca gct tgg atg ttc tta aag agt tcc aca aag    576
Pro His Gln Ala Trp Pro Ala Trp Met Phe Leu Lys Ser Ser Thr Lys
            180                185                190 cag att act gca csg gcm aca aag gat ggg act ttt gkc att tca aag    624
Gln Ile Thr Ala Xaa Xaa Thr Lys Asp Gly Thr Phe Xaa Ile Ser Lys
        195                200                205 aca                                                                 627
Thr

<210> SEQ ID NO 10
<211> LENGTH: 49
<212> TYPE: PRT
<213> ORGANISM: Artificial Sequence
<220> FEATURE:
<223> OTHER INFORMATION: Xaa at positions
      2,6,9,13,15,17,21,24,28,30,32,36,39,43, and 45 may
      be any amino acid
<223> OTHER INFORMATION: Description of Artificial Sequence: consensus
      sequence

<400> SEQUENCE: 10

Val Xaa Val His Cys Xaa Ala Gly Xaa Ser Arg Ser Xaa Thr Xaa Val
 1               5                  10                 15

Xaa Val His Cys Xaa Ala Gly Xaa Ser Arg Ser Xaa Thr Xaa Val Xaa
             20                  25                 30

Val His Cys Xaa Ala Gly Xaa Ser Arg Ser Xaa Thr Xaa Ala Tyr Leu
         35                  40                  45

Met

<210> SEQ ID NO 11
<211> LENGTH: 10
<212> TYPE: PRT
<213> ORGANISM: Artificial Sequence
<220> FEATURE:
<223> OTHER INFORMATION: Xaa at position 1 may be Ile or Val
<223> OTHER INFORMATION: Xaa at positions 4,7, and 8 may be any amino
      acid
<223> OTHER INFORMATION: Xaa at position 10 may be Ser or Thr
<223> OTHER INFORMATION: Description of Artificial Sequence: consensus
      sequence

<400> SEQUENCE: 11

Xaa His Cys Xaa Ala Gly Xaa Xaa Arg Xaa
 1               5                  10

<210> SEQ ID NO 12
<211> LENGTH: 9
<212> TYPE: PRT
<213> ORGANISM: Artificial Sequence
<220> FEATURE:
<223> OTHER INFORMATION: Xaa at position 1 may be His or Val
<223> OTHER INFORMATION: Xaa's at positions 3-7 may be any amino acid
<223> OTHER INFORMATION: Xaa at position 9 Ser or Thr
<223> OTHER INFORMATION: Description of Artificial Sequence: consensus
      sequence

<400> SEQUENCE: 12

Xaa Cys Xaa Xaa Xaa Xaa Xaa Arg Xaa
 1               5

<210> SEQ ID NO 13
```

```
<211> LENGTH: 7
<212> TYPE: PRT
<213> ORGANISM: Artificial Sequence
<220> FEATURE:
<223> OTHER INFORMATION: Xaa's at positions 2-6 may be any amino acid
<223> OTHER INFORMATION: Description of Artificial Sequence: consensus
      sequence

<400> SEQUENCE: 13

Cys Xaa Xaa Xaa Xaa Xaa Arg
 1               5

<210> SEQ ID NO 14
<211> LENGTH: 4
<212> TYPE: PRT
<213> ORGANISM: Artificial Sequence
<220> FEATURE:
<223> OTHER INFORMATION: Xaa at position 4 may be any amino acid
<223> OTHER INFORMATION: Description of Artificial Sequence: consensus
      sequence

<400> SEQUENCE: 14

Cys Ala Ala Xaa
 1

<210> SEQ ID NO 15
<211> LENGTH: 3
<212> TYPE: PRT
<213> ORGANISM: Artificial Sequence
<220> FEATURE:
<223> OTHER INFORMATION: Xaa at position 1 may be Ser or Thr
<223> OTHER INFORMATION: Xaa at position 2 may be any amino acid
<223> OTHER INFORMATION: Xaa at position 3 may be Arg or Lys
<223> OTHER INFORMATION: Description of Artificial Sequence: consensus
      sequence

<400> SEQUENCE: 15

Xaa Xaa Xaa
 1

<210> SEQ ID NO 16
<211> LENGTH: 8
<212> TYPE: PRT
<213> ORGANISM: Artificial Sequence
<220> FEATURE:
<223> OTHER INFORMATION: Xaa at position 1 may be Arg or Lys
<223> OTHER INFORMATION: Xaa's at positions 2,3, and 5-7 may be any
      amino acid
<223> OTHER INFORMATION: Xaa at position 4 may be Asp or Glu
<223> OTHER INFORMATION: Description of Artificial Sequence: consensus
      sequence

<400> SEQUENCE: 16

Xaa Xaa Xaa Xaa Xaa Xaa Xaa Tyr
 1               5

<210> SEQ ID NO 17
<211> LENGTH: 4
<212> TYPE: PRT
<213> ORGANISM: Artificial Sequence
<220> FEATURE:
<223> OTHER INFORMATION: Xaa at postion 3 may be Ser or Thr
<223> OTHER INFORMATION: Description of Artificial Sequence: consensus
      sequence

<400> SEQUENCE: 17

Asn Pro Xaa Pro
 1
```

```
<210> SEQ ID NO 18
<211> LENGTH: 19
<212> TYPE: PRT
<213> ORGANISM: Artificial Sequence
<220> FEATURE:
<223> OTHER INFORMATION: Xaa's at positions 11 and 12 may be any amino
      acid
<223> OTHER INFORMATION: Description of Artificial Sequence: consensus
      sequence

<400> SEQUENCE: 18

Gly Glu Asp Arg Lys His Pro Phe Tyr Trp Xaa Xaa Ser Thr Ala Gly
 1               5                  10                  15

Cys Asn Pro

<210> SEQ ID NO 19
<211> LENGTH: 4
<212> TYPE: PRT
<213> ORGANISM: Artificial Sequence
<220> FEATURE:
<223> OTHER INFORMATION: Xaa at position 1 Ser or Thr
<223> OTHER INFORMATION: Xaa's at positions 2 and 3 may be any amino
      acid
<223> OTHER INFORMATION: Xaa at position 4 may be Asp or Glu
<223> OTHER INFORMATION: Description of Artificial Sequence: consensus
      sequence

<400> SEQUENCE: 19

Xaa Xaa Xaa Xaa
 1

<210> SEQ ID NO 20
<211> LENGTH: 173
<212> TYPE: PRT
<213> ORGANISM: Homo sapiens

<400> SEQUENCE: 20

Met Ala Arg Met Asn Arg Pro Ala Pro Val Glu Val Thr Tyr Lys Asn
 1               5                  10                  15

Met Arg Phe Leu Ile Thr His Asn Pro Thr Asn Ala Thr Leu Asn Lys
                20                  25                  30

Phe Ile Glu Glu Leu Lys Lys Tyr Gly Val Thr Thr Ile Val Arg Val
            35                  40                  45

Cys Glu Ala Thr Tyr Asp Thr Thr Leu Val Glu Lys Glu Gly Ile His
        50                  55                  60

Val Leu Asp Trp Pro Phe Asp Asp Gly Ala Pro Pro Ser Asn Gln Ile
 65                 70                  75                  80

Val Asp Asp Trp Leu Ser Leu Val Lys Ile Lys Phe Arg Glu Glu Pro
                85                  90                  95

Gly Cys Cys Ile Ala Val His Cys Val Ala Gly Leu Gly Arg Ala Pro
            100                 105                 110

Val Leu Val Ala Leu Ala Leu Ile Glu Gly Gly Met Lys Tyr Glu Asp
        115                 120                 125

Ala Val Gln Phe Ile Arg Gln Lys Arg Arg Gly Ala Phe Asn Ser Lys
    130                 135                 140

Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170

<210> SEQ ID NO 21
<211> LENGTH: 185
```

-continued

```
<212> TYPE: PRT
<213> ORGANISM: Homo sapiens

<400> SEQUENCE: 21

Met Ser Gly Ser Phe Glu Leu Ser Val Gln Asp Leu Asn Asp Leu Leu
 1               5                  10                  15

Ser Asp Gly Ser Gly Cys Tyr Ser Leu Pro Ser Gln Pro Cys Asn Glu
            20                  25                  30

Val Thr Pro Arg Ile Tyr Val Gly Asn Ala Ser Val Ala Gln Asp Ile
        35                  40                  45

Pro Lys Leu Gln Lys Leu Gly Ile Thr His Val Leu Asn Ala Ala Glu
    50                  55                  60

Gly Arg Ser Phe Met His Val Asn Thr Asn Ala Asn Phe Tyr Lys Asp
65                  70                  75                  80

Ser Gly Ile Thr Tyr Leu Gly Ile Lys Ala Asn Asp Thr Gln Glu Phe
                85                  90                  95

Asn Leu Ser Ala Tyr Phe Glu Arg Ala Ala Asp Phe Ile Asp Gln Ala
            100                 105                 110

Leu Ala Gln Lys Asn Gly Arg Val Leu Val His Cys Arg Glu Gly Tyr
        115                 120                 125

Ser Arg Ser Pro Thr Leu Val Ile Ala Tyr Leu Met Met Arg Gln Lys
    130                 135                 140

Met Asp Val Lys Ser Ala Leu Ser Ile Val Arg Gln Asn Arg Glu Ile
145                 150                 155                 160

Gly Pro Asn Asp Gly Phe Leu Ala Gln Leu Cys Gln Leu Asn Asp Arg
                165                 170                 175

Leu Ala Lys Glu Gly Lys Leu Lys Pro
            180                 185

<210> SEQ ID NO 22
<211> LENGTH: 314
<212> TYPE: PRT
<213> ORGANISM: Mus musculus

<400> SEQUENCE: 22

Met Gly Leu Glu Thr Ala Cys Glu Leu Glu Cys Ala Ala Leu Gly Ala
 1               5                  10                  15

Leu Leu Arg Glu Pro Arg Glu Ala Glu Arg Thr Leu Leu Leu Asp Cys
            20                  25                  30

Arg Pro Phe Leu Ala Phe Cys Arg Ser His Val Arg Ala Ala Arg Pro
        35                  40                  45

Val Pro Trp Asn Ala Leu Leu Arg Arg Arg Ala Pro Gly Thr Pro Ala
    50                  55                  60

Ala Ala Leu Ala Cys Leu Leu Pro Asp Arg Ala Leu Arg Ala Arg Leu
65                  70                  75                  80

Gly Arg Gly Glu Leu Ala Arg Ala Val Val Leu Asp Glu Ser Ser Ala
                85                  90                  95

Ser Val Thr Glu Leu Pro Pro Asp Gly Pro Ala His Leu Leu Leu Ala
            100                 105                 110

Ala Leu Gln His Glu Met Arg Gly Gly Pro Thr Thr Val Cys Phe Leu
        115                 120                 125

Arg Gly Gly Phe Lys Ser Phe Gln Thr Tyr Cys Pro Asp Leu Cys Ser
    130                 135                 140

Glu Ala Pro Ala Gln Ala Leu Pro Ala Gly Ala Glu Asn Ser Asn
145                 150                 155                 160
```

```
Ser Asp Pro Arg Val Pro Ile Tyr Asp Gln Gly Gly Pro Val Glu Ile
            165                 170                 175

Leu Pro Tyr Leu Tyr Leu Gly Ser Cys Asn His Ser Ser Asp Leu Gln
            180                 185                 190

Gly Leu Gln Ala Cys Gly Ile Thr Ala Val Leu Asn Val Ser Ala Ser
            195                 200                 205

Cys Pro Asn His Phe Glu Gly Leu Phe His Tyr Lys Ser Ile Pro Val
            210                 215                 220

Glu Asp Asn Gln Met Val Glu Ile Ser Ala Trp Phe Gln Glu Ala Ile
225                 230                 235                 240

Ser Phe Ile Asp Ser Val Lys Asn Ser Gly Gly Arg Val Leu Val His
            245                 250                 255

Cys Gln Ala Gly Ile Ser Arg Ser Ala Thr Ile Cys Leu Ala Tyr Leu
            260                 265                 270

Ile Gln Ser His Arg Val Arg Leu Asp Glu Ala Phe Asp Phe Val Lys
            275                 280                 285

Gln Arg Arg Gly Val Ile Ser Pro Asn Phe Ser Phe Met Gly Gln Leu
            290                 295                 300

Leu Gln Leu Glu Thr Gln Val Leu Cys His
305                 310

<210> SEQ ID NO 23
<211> LENGTH: 150
<212> TYPE: PRT
<213> ORGANISM: Caenorhabditis elegans

<400> SEQUENCE: 23

Met Pro Phe Arg Ser Met Lys Asp Glu Leu Ile Gln Lys Glu Asn Val
  1               5                  10                  15

Gly Gly Val Val Cys Cys Thr Glu Glu Phe Glu Leu Lys Ala Ala Met
            20                  25                  30

Asn Ala Met Arg Glu Val Asp Trp Lys Asn Glu Gly Val Glu Phe Phe
            35                  40                  45

Ala Val Pro Met Lys Asp Phe Thr Gly Thr Ala Pro Arg Ala Glu Ile
 50                 55                  60

Asn Glu Ala Val Glu Phe Ile Glu Ser Val Ala Ser Lys Gly Lys Thr
 65                 70                  75                  80

Val Tyr Val His Cys Lys Ala Gly Arg Thr Arg Ser Ala Thr Val Ala
            85                  90                  95

Thr Cys Tyr Leu Met Lys Ser Arg Asn Trp Met Ser Asn Val Ala Trp
            100                 105                 110

Glu Phe Leu Lys Asp Lys Arg His Gln Val Leu Leu Arg Asn Ala His
            115                 120                 125

Trp Arg Thr Val Asn Glu Tyr Arg Arg Phe Leu Asp Ser Asn Ser Ser
            130                 135                 140

Ser Thr Gly Ser Ser Asn
145                 150
```

What is claimed is:

1. An isolated mammalian protein tyrosine phosphatase polypeptide comprising an amino acid sequence encoded by a nucleotide sequence which hybridizes to a full complement of a nucleotide sequence selected from the group consisting of: SEQ ID NO:4, and SEQ ID NO: 7, at 6×SSC at 45 °C., followed by one or more washes in 0.2×SSC, 0.1% SDS at 50–65° C.

2. An isolated mammalian protein tyrosine phosphatase polypeptide comprising an amino acid sequence which is at least 90% identical to an amino acid sequence selected from the group consisting of: SEQ ID NO: 5 and SEQ ID NO:8, wherein said percent identity is calculated using the ALIGN program for comparing amino acid sequence, a PAM120 weight residue table, a gap length penalty of 12, and a gap penalty of 4.

3. An isolated polypeptide comprising the amino acid sequence of SEQ ID NO:2.

4. An isolated polypeptide comprising the amino acid sequence of SEQ ID NO:5.

5. An isolated polypeptide comprising the amino acid sequence of SEQ ID NO:8.

6. An isolated polypeptide consisting of the amino acid sequence of SEQ ID NO:2.

7. An isolated polypeptide consisting of the amino acid sequence of SEQ ID NO:5.

8. An isolated polypeptide consisting of the amino acid sequence of SEQ ID NO:8.

9. An isolated mammalian protein tyrosine phosphatase polypeptide comprising at least 50 consecutive amino acid residues of the amino acid sequence of SEQ ID NO:8, wherein said polypeptide has a Cardiovascular System Associated Protein Tyrosine Phosphatase (CSAPTP) activity.

10. An isolated mammalian protein tyrosine phosphatase polypeptide consisting of an amino acid sequence which is at least 90% identical to an amino acid sequence selected from the group consisting of: SEQ ID NO: 5 and SEQ ID NO:8, wherein said percent identity is calculated using the ALIGN program for comparing amino acid sequence, using a PAM120 weight residue table, a gap length penalty of 12, and a gap penalty of 4.

11. An isolated mammalian protein tyrosine phosphatase polypeptide which is encoded by a nucleic acid molecule comprising a nucleotide sequence which is at least 90% identical to the nucleotide sequence of SEQ ID NO:1, SEQ ID NO:4, or SEQ ID NO:7, wherein said percent identity is calculated using the ALIGN program for comparing nucleic acid sequence, using a PAM120 weight residue table, a gap length penalty of 12, and a gap penalty of 4.

12. An isolated mammalian protein tyrosine phosphatase polypeptide which is encoded by a nucleic acid molecule consisting of a nucleotide sequence which is at least 90% identical to the nucleotide sequence of SEQ ID NO:1, SEQ ID NO:4, or SEQ ID NO:7, wherein said percent identity is calculated using the ALIGN program for comparing nucleic acid sequence, using a PAM120 weight residue table, a gap length penalty of 12, and a gap penalty of 4.

13. An isolated mammalian protein tyrosine phosphatase polypeptide consisting of an amino acid sequence encoded by a nucleotide sequence which hybridizes to a full complement of a nucleotide sequence selected from the group consisting of: SEQ ID NO:4, and SEQ ID NO: 7, at 6×SSC at 45 ° C., followed by one or more washes in 0.2×SSC, 0.1% SDS at 50–65° C.

14. An isolated mammalian protein tyrosine phosphatase polypeptide comprising at least 100 consecutive amino acid residues of the amino acid sequence of SEQ ID NO5, wherein said polypeptide has a Cardiovascular System Associated Protein Tyrosine Phosphatase (CSAPTP) activity.

15. An isolated fusion polypeptide comprising the polypeptide of any one of claims 1, 2, 3, 4, 5, 6, 7, 8, 9, 10, 11, 12, 13 or 14, operatively linked to a heterologous polypeptide.

* * * * *